(12) United States Patent
Kim et al.

(10) Patent No.: US 12,247,023 B2
(45) Date of Patent: Mar. 11, 2025

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Eun Min Kim, Cheonan-si (KR); Hye Jeong Kim, Cheonan-si (KR); Hyung Dong Lee, Cheonan-si (KR); Ki Hwan Yoon, Cheonan-si (KR); Jung Geun Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/814,915

(22) Filed: Aug. 26, 2024

(65) Prior Publication Data

US 2024/0425489 A1     Dec. 26, 2024

Related U.S. Application Data

(63) Continuation-in-part of application No. 18/568,709, filed as application No. PCT/KR2022/009846 on Jul. 7, 2022.

(30) Foreign Application Priority Data

Jul. 21, 2021   (KR) .................. 10-2021-0095920
Aug. 19, 2021  (KR) .................. 10-2021-0109156

(51) Int. Cl.
*C07D 407/12*   (2006.01)
*C07B 59/00*    (2006.01)
*C07D 307/91*   (2006.01)
*C07D 333/76*   (2006.01)
*C07D 409/12*   (2006.01)
*H10K 85/60*    (2023.01)

(52) U.S. Cl.
CPC .......... *C07D 407/12* (2013.01); *C07B 59/004* (2013.01); *C07D 307/91* (2013.01); *C07D 333/76* (2013.01); *C07D 409/12* (2013.01); *H10K 85/615* (2023.02); *H10K 85/633* (2023.02); *H10K 85/6574* (2023.02); *H10K 85/6576* (2023.02); *C07B 2200/05* (2013.01)

(58) Field of Classification Search
CPC .. C07D 407/12; C07D 409/12; H10K 85/633; H10K 85/636
See application file for complete search history.

(56) References Cited

FOREIGN PATENT DOCUMENTS

| CN | 111196822 A | 5/2020 |
| CN | 112266371 A | 1/2021 |
| CN | 114702432 A * | 7/2022 |
| KR | 10-2018-0041607 A | 4/2018 |
| KR | 10-2018-0118748 A | 10/2018 |
| KR | 10-2076958 B1 | 2/2020 |
| WO | 2021/141356 A1 | 7/2021 |
| WO | WO-2021136006 A1 * | 7/2021 ........... C07D 209/86 |

* cited by examiner

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound of Formula (1-10) capable of improving the light-emitting efficiency, stability, and lifespan of an organic electronic element, a composition comprising the same, an organic electronic element using the same, and an electronic device thereof.

14 Claims, 2 Drawing Sheets

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer and an electron injection layer, etc.

A material used as an organic material layer in an organic electronic element may be classified into a light emitting material and a charge transport material, such as a hole injection material, a hole transport material, an electron transport material, an electron injection material and the like depending on its function.

The most problematic issues with organic electroluminescent devices are lifespan and efficiency, and as displays become larger in area, these efficiency and lifespan issues must be resolved.

Efficiency, lifespan and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase.

However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Further, recently, in organic electroluminescent devices, in order to solve the emission problem in the hole transport layer, an emitting-auxiliary layer must be present between the hole transport layer and an emitting layer, and it is necessary to develop different emitting-auxiliary layers according to each of the emitting layers (R, G, B).

In general, electrons are transferred from the electron transport layer to the emitting layer, and holes are transferred from the hole transport layer to the emitting layer to generate excitons by recombination.

However, since the materials used in the hole transport layer must have a low HOMO value, most of them have a low T1 value, therefore the exciton generated in the emitting layer is transferred to the hole transport layer, resulting in charge unbalance in the emitting layer, and light is emitted at the interface of the hole transport layer.

When light is emitted at the interface of the hole transport layer, the color purity and efficiency of the organic electronic element are lowered and the life span is shortened. Therefore, it is urgently required to develop an emitting-auxiliary layer having a high T1 value and a HOMO level between the HOMO energy level of the hole transport layer and the HOMO energy level of the emitting layer.

Meanwhile, it is necessary to develop a hole injection layer material having stable characteristics, that is, a high glass transition temperature, against Joule heating generated when the device is driven, while delaying penetration of the metal oxide from the anode electrode (ITO), which is one of the causes of shortening the lifespan of the organic electronic element, into the organic layer. The low glass transition temperature of the hole transport layer material has a characteristic that when the device is driven, the uniformity of the surface of the thin film is lowered, which has been reported to have a great influence on the lifespan of the device. In addition, OLED devices are mainly formed by a deposition method, and it is necessary to develop a material that can withstand long time in deposition, that is, a material having high heat resistance characteristics.

That is, in order to sufficiently exhibit the excellent characteristics of the organic electronic element, a material for forming an organic material layer in an element such as a hole injection material, a hole transport material, a light emitting material, an electron transport material, an electron injection material, an emitting-auxiliary layer material should be supported by stable and efficient materials. However, such a stable and efficient organic material layer material for an organic electronic element has not been sufficiently developed yet. Therefore, the development of new materials continues to be required, and in particular, the development of materials for the emitting-auxiliary layer is urgently required.

BRIEF DESCRIPTION OF THE INVENTION

Summary

In order to solve the problems of the background art described above, the present invention has revealed a compound having a novel structure, and that when the compound is applied to an organic electronic element, the luminous efficiency, stability and lifespan of the element are greatly improved.

Accordingly, it is an object of the present invention to provide a novel compound, an organic electronic element using the same, and an electronic device thereof.

Technical Solution

The present invention provides a compound represented by Formula (1-10).

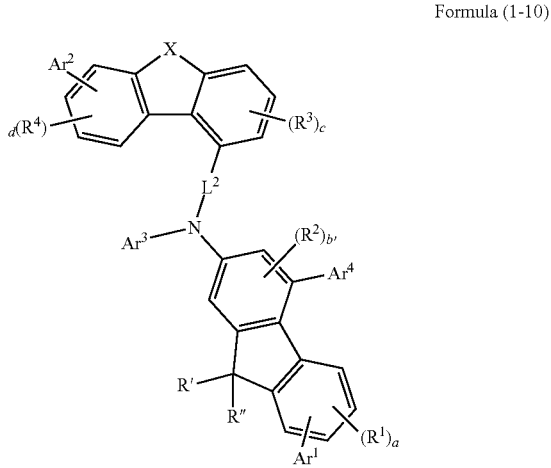

Formula (1-10)

In another aspect, the present invention provides an organic electronic element comprising a compound represented by Formula (1-10) and an electronic device thereof.

Effects of the Invention

By using the compound according to the present invention, it is possible to achieve a high luminous efficiency, a low driving voltage, and a high heat resistance of the element, and can greatly improve the color purity and lifespan of the element.

Figure 1:
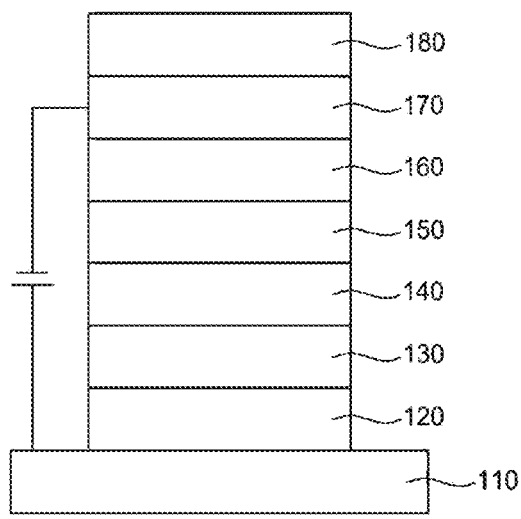
FIG. 1 to FIG. 3 illustrate an example of an organic electronic element according to the present invention.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting-auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, includes fluorine (F), bromine (Br), chlorine (Cl), or iodine (I).

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and may also be formed in conjunction with an adjacent group. Examples of "aryl group" may include a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of monocyclic and polycyclic rings, and may include heteroaliphatic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including SO₂ instead of carbon consisting of cycle. For example, "heterocyclic group" includes compound below.

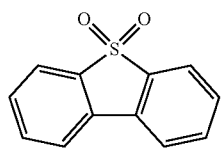 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

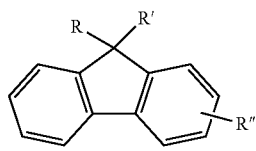

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include one or more heteroatoms, but are not limited thereto.

Unless otherwise stated, the term "substituted or unsubstituted", as used herein, means that substitution is substituted by at least one substituent selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiophen group, a $C_6$-$C_{20}$ arylthiophen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited thereto.

Unless otherwise expressly stated, the Formula used in the present invention, as used herein, is applied in the same manner as the substituent definition according to the definition of the exponent of the following Formula.

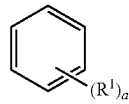

wherein, when a is an integer of 0, the substituent $R^1$ is absent, when a is an integer of 1, the sole substituent $R^1$ is linked to any one of the carbon constituting the benzene ring, when a is an integer of 2 or 3, each substituent $R^1$'s may be the same and different, when a is an integer of 4 to 6, and is linked to the benzene ring in a similar manner, whereas the indication of hydrogen bound to the carbon forming the benzene ring is omitted.

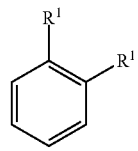
(a=2)

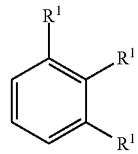
(a=3)

Hereinafter, a compound according to an aspect of the present invention and an organic electronic element comprising the same will be described.

The present invention provides a compound represented by Formula (1-10):

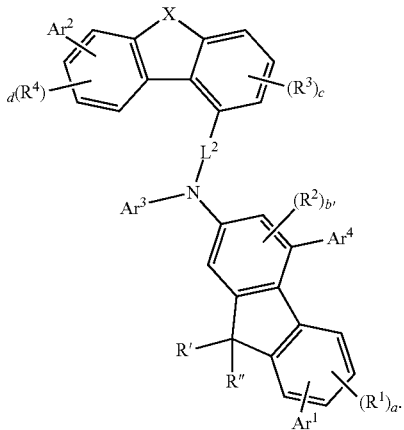

Formula (1-10)

In Formula (1-10), each symbol may be defined as follows:

$R^1$, $R^2$, $R^3$ and $R^4$ are each independently the same or different, and each independently selected from the group consisting of a hydrogen; deuterium; halogen; an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

wherein in case $R^1$, $R^2$, $R^3$ and $R^4$ are an aryl group, it is preferably an $C_6$-$C_{24}$ aryl group, more preferably an $C_6$-$C_{20}$ aryl group, $C_6$-$C_{18}$ aryl group, $C_6$-$C_{16}$ aryl group, $C_6$-$C_{14}$ aryl group, $C_6$-$C_{12}$ aryl group, $C_6$-$C_{10}$ aryl group, $C_6$ aryl group, for example, it may be phenyl, biphenyl, terphenyl, naphthalene, phenanthrene, etc., wherein in case $R^1$, $R^2$, $R^3$ and $R^4$ are a heterocyclic group, it may be preferably a $C_2$~$C_{30}$ heterocyclic group, more preferably a $C_2$~$C_{24}$ heterocyclic group, $C_2$-$C_{20}$ heterocyclic group, $C_2$-$C_{18}$ heterocyclic group, $C_2$-$C_{16}$ heterocyclic group, $C_2$-$C_{12}$ heterocyclic group, $C_{12}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc., wherein in case $R^1$, $R^2$, $R^3$ and $R^4$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, wherein in case $R^1$, $R^2$, $R^3$ and $R^4$ are an aliphatic ring group, it may be preferably a $C_3$-$C_{30}$ aliphatic ring, more preferably a $C_3$-$C_{25}$ aliphatic ring, $C_3$-$C_{18}$ aliphatic ring or $C_3$-$C_{12}$ aliphatic ring, and may specifically be cyclobutane, cyclopentane, cyclohexane, bicycloheptane, adamantyl, etc., wherein in case $R^1$, $R^2$, $R^3$ and $R^4$ are an alkyl group, it may be preferably a $C_1$-$C_{30}$ alkyl group, more preferably a $C_1$-$C_{25}$ alkyl group, $C_1$-$C_{18}$ alkyl group, or $C_1$-$C_{12}$ alkyl group. For example, it may be a methyl group, ethyl group, propyl group, isopropyl group, butyl group, t-butyl group, pentyl group, etc., wherein in case $R^1$, $R^2$, $R^3$ and $R^4$ are alkoxyl groups, it may be preferably $C_1$~$C_{25}$ alkoxyl group, $C_1$~$C_{18}$ alkoxyl group or $C_1$~$C_{12}$ alkoxyl group, wherein in case $R^1$, $R^2$, $R^3$ and $R^4$ are an aryloxy group, it may be preferably an $C_6$~$C_{25}$ aryloxy group, $C_6$~$C_{18}$ aryloxy group or $C_6$~$C_{12}$ aryloxy group, a, c and d are each independently an integer of 0 to 3, b' is an integer from 0 to 2, R' and R" are each independently selected from the group consisting of an $C_6$-$C_{60}$ aryl group; fluorenyl group; a $C_1$-$C_{50}$ alkyl group; and a $C_2$-$C_{20}$ alkenyl group; or R' and R" can be bonded to each other to form a ring, wherein in case R' and R" are an aryl group, it may be preferably a $C_6$-$C_{24}$ aryl group, more preferably a $C_6$-$C_{20}$ aryl group, $C_6$-$C_{18}$ aryl group, $C_6$-$C_{16}$ aryl group, $C_6$-$C_{14}$ aryl group, $C_6$-$C_{12}$ aryl group, $C_6$-$C_{10}$ aryl group, $C_6$ aryl group, for example, it may be phenyl, biphenyl, terphenyl, naphthalene, phenanthrene, etc., wherein in case R' and R" are an alkyl group, it may be preferably a $C_1$-$C_{30}$ alkyl group, more preferably a $C_1$-$C_{25}$ alkyl group, $C_1$-$C_{18}$ alkyl group, or $C_1$-$C_{12}$ alkyl group, for example, it may be a methyl group, ethyl group, propyl group, isopropyl group, butyl group, t-butyl group, pentyl group, etc., wherein in case R' and R" are an alkenyl group, it is preferably a $C_1$-$C_{25}$ alkenyl group, more preferably a $C_1$-$C_{18}$ alkenyl group, a $C_1$-$C_{15}$ alkenyl group, or a $C_1$-$C_{12}$ alkenyl group, $Ar^1$ is each independently selected from the group consisting of a hydrogen; deuterium; an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a $C_1$-$C_{50}$ alkyl group; and a fused ring group of a $C_3$-$C_{60}$ aliphatic ring and a $C_6$-$C_{60}$ aromatic ring, $Ar^2$ is each independently selected from the group consisting of an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; and a $C_1$-$C_{50}$ alkyl group, $Ar^3$ is each independently selected from the group consisting of an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring; a $C_1$-$C_{50}$ alkyl group; and a $C_2$-$C_{20}$ alkenyl group, $Ar^4$ is each independently selected from the group consisting of an $C_6$-$C_{60}$ aryl group; a $C_2$-$C_{60}$ heterocyclic group including at least one heteroatom of O, N, S, Si or P; a $C_3$-$C_{60}$ aliphatic ring; and a $C_1$-$C_{50}$ alkyl group, wherein in case $Ar^1$, $Ar^2$, $Ar^3$ and $Ar^4$ are an aryl group, it may be preferably a $C_6$-$C_{24}$ aryl group, more preferably a $C_6$-$C_{20}$ aryl group, a $C_6$-$C_{18}$ aryl group, a $C_6$-$C_{16}$ aryl group, a $C_6$-$C_{14}$ aryl group, a $C_6$-$C_{12}$ aryl group, a $C_6$-$C_{10}$ aryl group, a $C_6$ aryl group, for example, it may be phenyl, biphenyl, terphenyl, naphthalene, phenanthrene, etc., wherein in case $Ar^1$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, wherein in case $Ar^1$, $Ar^2$, $Ar^3$ and $Ar^4$ are a heterocyclic group, it may be preferably a $C_2$~$C_{30}$ heterocyclic group, more preferably a $C_2$~$C_{24}$ heterocyclic group, a $C_2$~$C_{20}$ heterocyclic group, a $C_2$~$C_{18}$ heterocyclic group, a $C_2$~$C_{16}$ heterocyclic group, a $C_2$~$C_{12}$ heterocyclic group, a $C_{12}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, naphthobenzofuran, naphthobenzothiophene, etc., wherein in case $Ar^1$, $Ar^2$, $Ar^3$ and $Ar^4$ are an alkyl group, it may be preferably a $C_1$-$C_{30}$ alkyl group, more preferably a $C_1$-$C_{25}$ alkyl group, $C_1$-$C_{18}$ alkyl group, or $C_1$-$C_{12}$ alkyl group, for example, it may be a methyl group, ethyl group, propyl group, isopropyl group, butyl group, t-butyl group, pentyl group, etc., wherein in case $Ar^1$, $Ar^2$, $Ar^3$ and $Ar^4$ are an aliphatic ring group, it may be preferably a $C_3$-$C_{30}$ aliphatic ring, more preferably a $C_3$-$C_{25}$ aliphatic ring, $C_3$-$C_{18}$ aliphatic ring or $C_3$-$C_{12}$ aliphatic ring, and may specifically be cyclobutane, cyclopentane, cyclohexane, bicycloheptane, adamantyl, etc., X is O or S, $L^2$ is a single bond; a $C_6$-$C_{60}$ arylene group, wherein in case $L^2$ is an arylene group, it may be preferably a $C_6$-$C_{24}$ arylene group, more preferably a $C_6$-$C_{20}$ arylene group, a $C_6$-$C_{18}$ arylene group, a $C_6$-$C_{16}$ arylene group, a $C_6$-$C_{14}$ arylene group, a $C_6$-$C_{12}$ arylene group, a $C_6$-$C_{10}$ arylene group, a $C_6$ arylene group, for example, phenyl, biphenyl, terphenyl, naphthalene, phenanthrene, etc., wherein the aryl group, arylene group, heterocyclic group, fluorenyl group, fluorenylene group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and also the hydrogen of these substituents may be further substituted with one or more deuterium, and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, the compound represented by Formula (1-10) is represented by any of the Formulas (1-11) to (1-13):

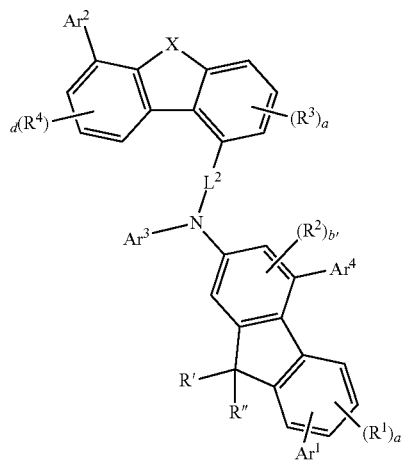

Formula (1-11)

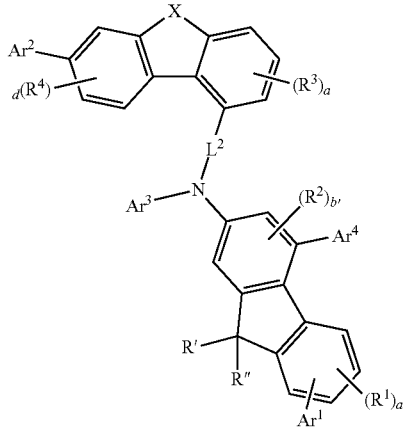

Formula (1-12)

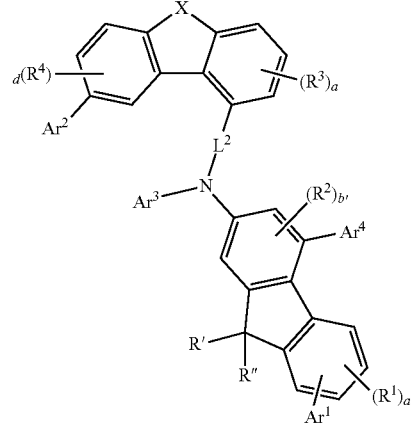

Formula (1-13)

Wherein X, $R^1$, $R^2$, $R^3$, $R^4$, R', R", $Ar^1$, $Ar^2$, $Ar^3$, $Ar^4$, $L^2$, a, b', c and d are the same as defined above.

As an example, the present invention provides a compound wherein at least one of $Ar^1$, $Ar^2$, $Ar^3$ and $Ar^4$ is represented by the following Formulae Ar-1 to Ar-6.

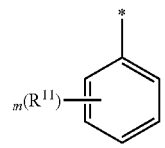

<Formula Ar-1>

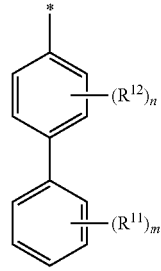

<Formula Ar-2>

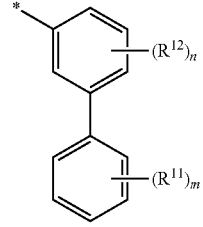

<Formula Ar-3>

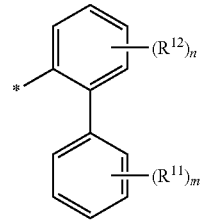

<Formula Ar-4>

-continued

<Formula Ar-5>

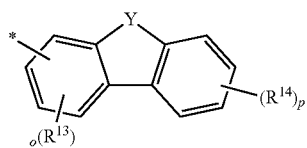

<Formula Ar-6>

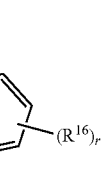

Wherein,
1) $R^{11}$, $R^{12}$, $R^{13}$, $R^{14}$, $R^{15}$ and $R^{16}$ are selected from the group consisting of a hydrogen; deuterium; halogen; cyano group; nitro group; a $C_1$-$C_{20}$ alkoxyl group; a $C_1$-$C_{20}$ alkyl group; a $C_2$-$C_{20}$ alkeynyl group; a $C_2$-$C_{20}$ alkynyl group; a $C_6$-$C_{20}$ aryl group; a $C_6$-$C_{20}$ aryl group substituted with deuterium; fluorenyl group; a $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group;
2) Y is O, S, $CR^xR^y$ or $NR^z$
3) $R^a$, $R^b$, $R^x$, $R^y$ and $R^z$ are the same as the definition of $R^{11}$, or $R^a$ and $R^b$ or $R^x$ and $R^y$ can be bonded to each other to form a ring,
4) m is an integer of 0 to 5, n, p, q and r are an integer of 0 to 4, o is an integer of 0 to 3,
5) * means a position to be bonded.

Also, $L^2$ is represented by any one of the following Formulas L-1 to L-3:

<Formula L-1>

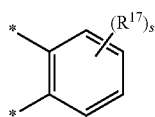

<Formula L-2>

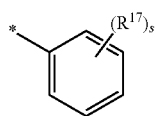

<Formula L-3>

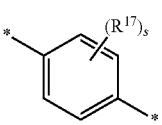

Wherein:
1) $R^{17}$ is each independently selected from the group consisting of a hydrogen; deuterium; halogen; cyano group; nitro group; a $C_1$-$C_{20}$ alkoxyl group; a $C_1$-$C_{20}$ alkyl group; a $C_2$-$C_{20}$ alkeynyl group; a $C_2$-$C_{20}$ alkynyl group; a $C_6$-$C_{20}$ aryl group; a $C_6$-$C_{20}$ aryl group substituted with deuterium; fluorenyl group; a $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group;
2) s is an integer of 0 to 4,
3) * means a position to be bonded.

Specifically, the compound represented by Formula (1-10) may be any one of the following compounds, but is not limited thereto.

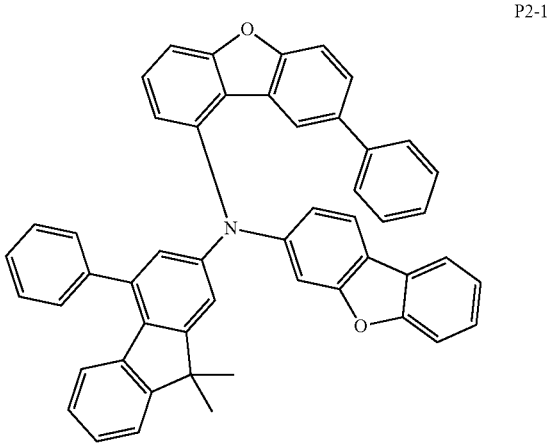

P2-1

P2-2

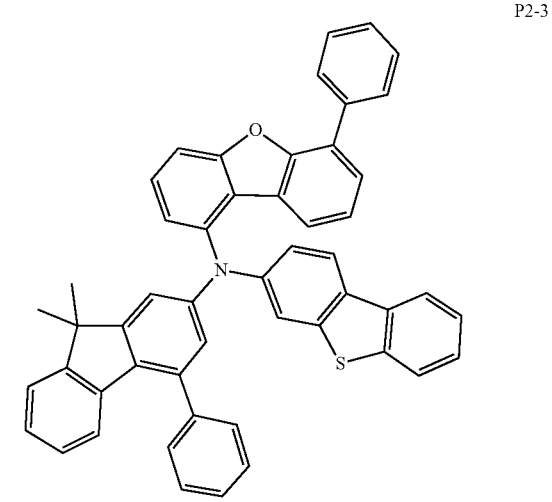

P2-3

P2-4
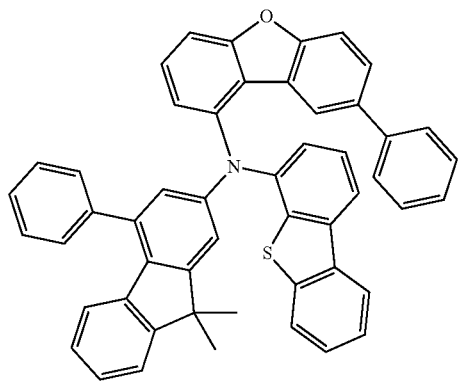
P2-5
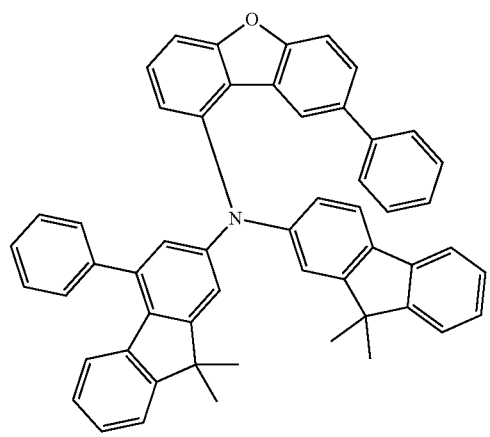
P2-6
P2-7
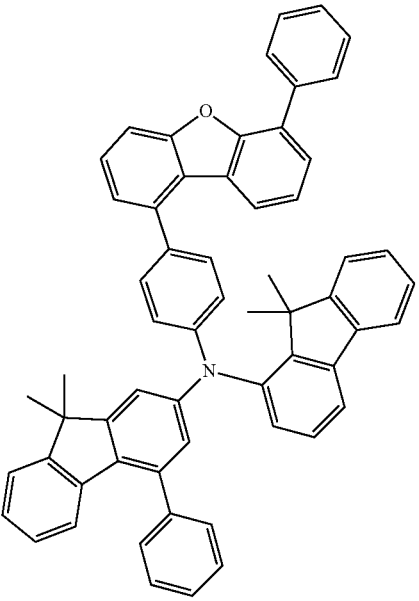
P2-8
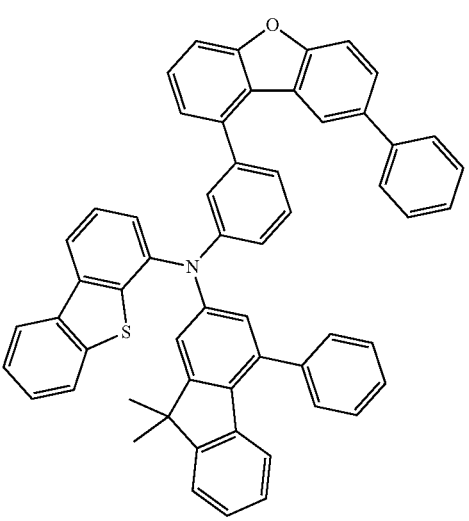
P2-9
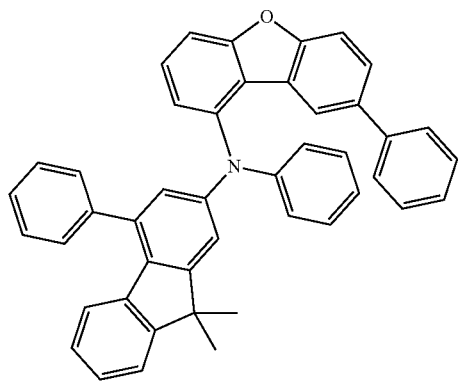

P2-10
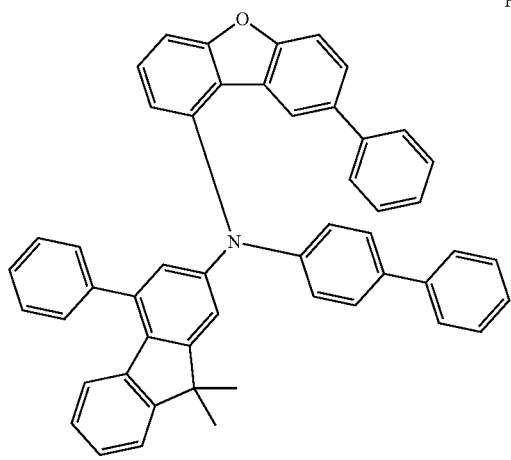
P2-11
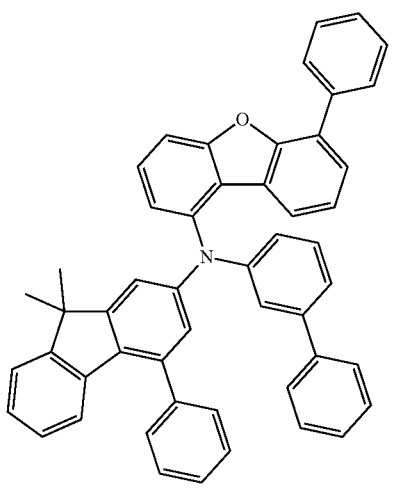
P2-12
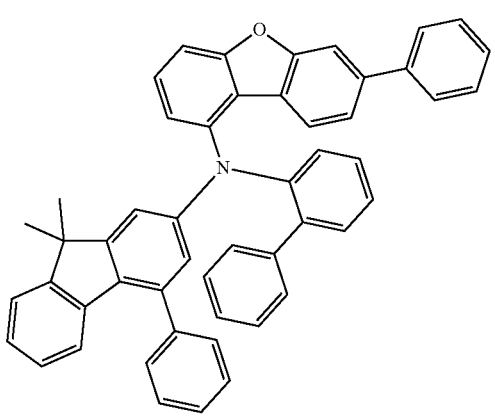
P2-13
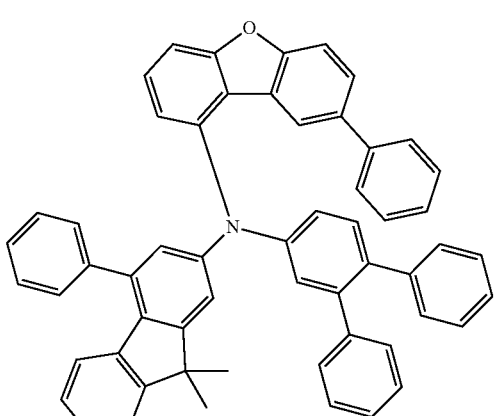
P2-14
P2-15
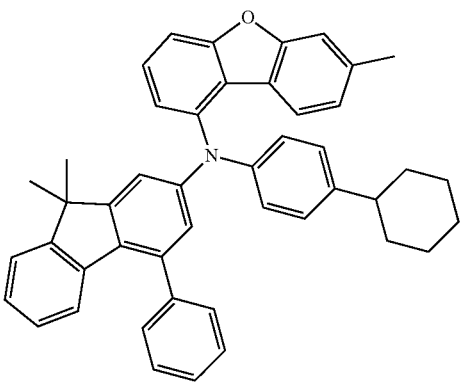

P2-16
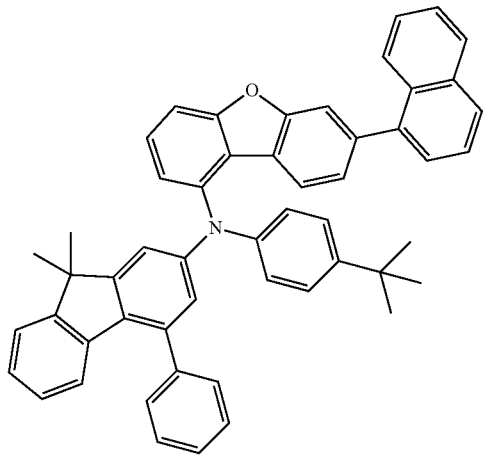
P2-17
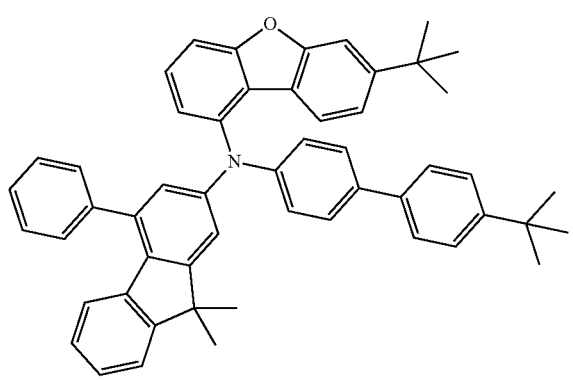
P2-18
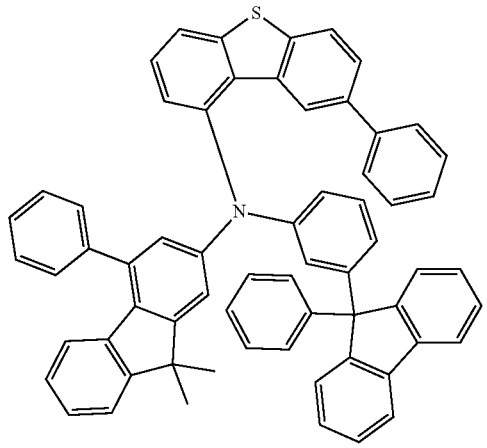
P2-19
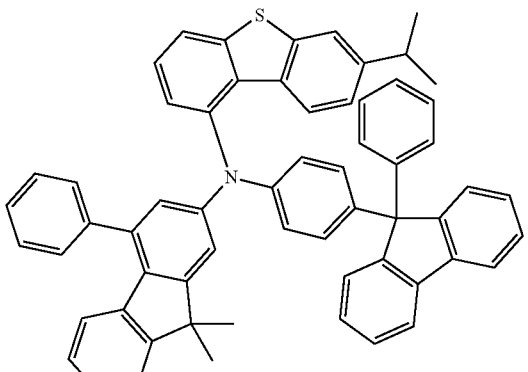
P2-20
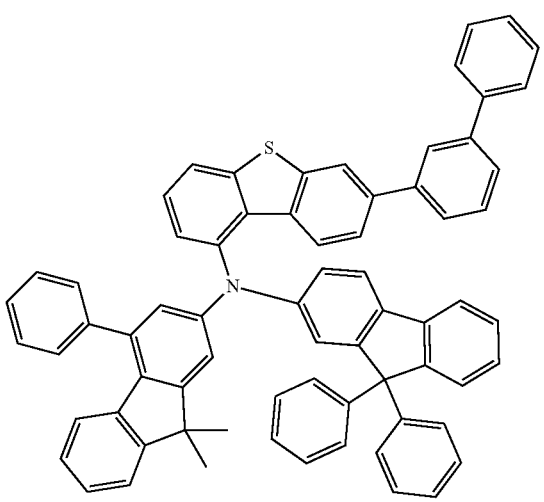
P2-21
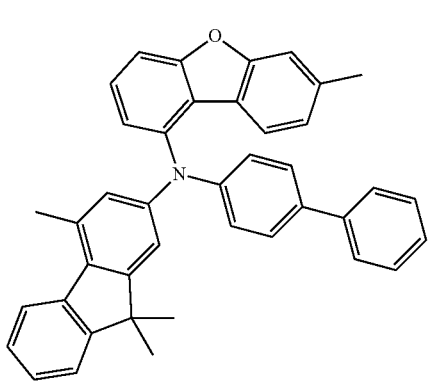

-continued
P2-22
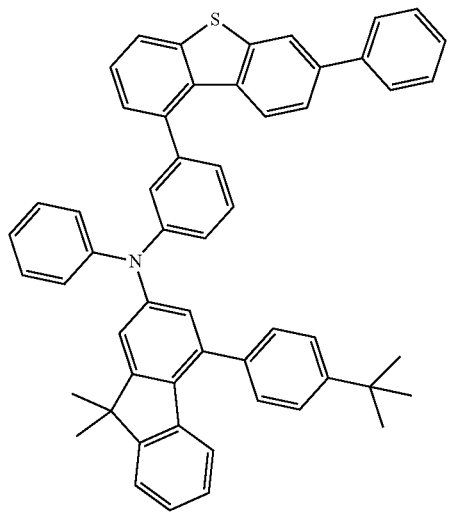
P2-23
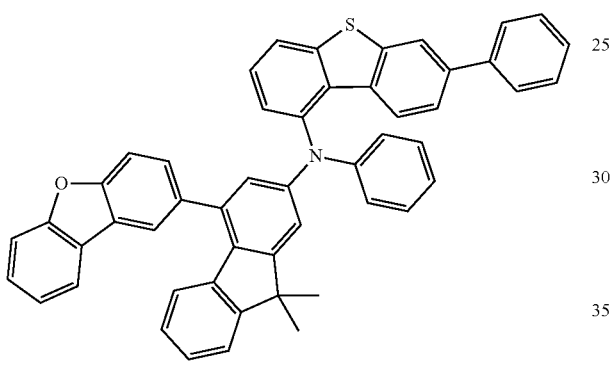
P2-24
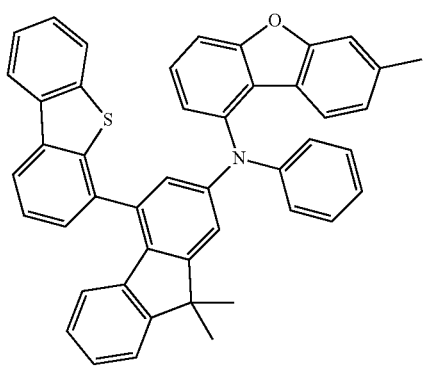
P2-25
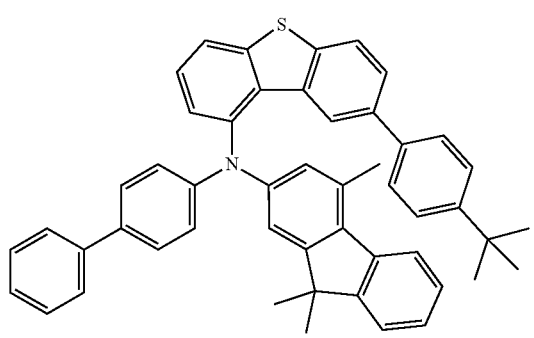
P2-26
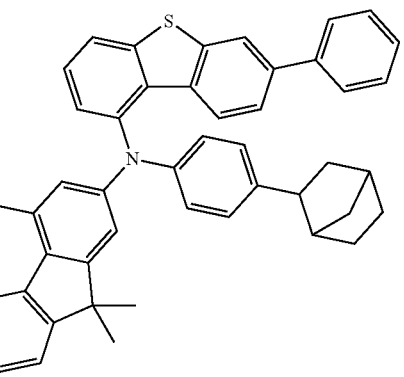
P2-27
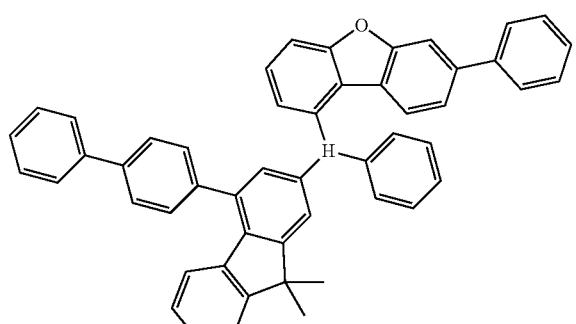
P2-28
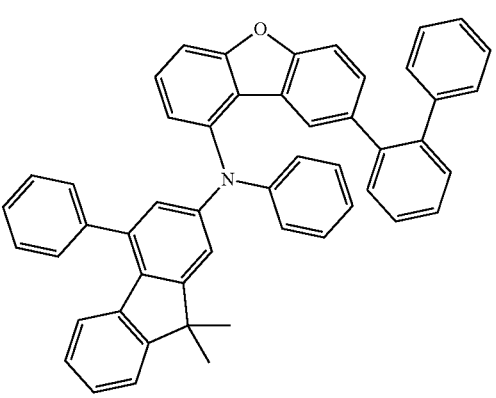

P2-29
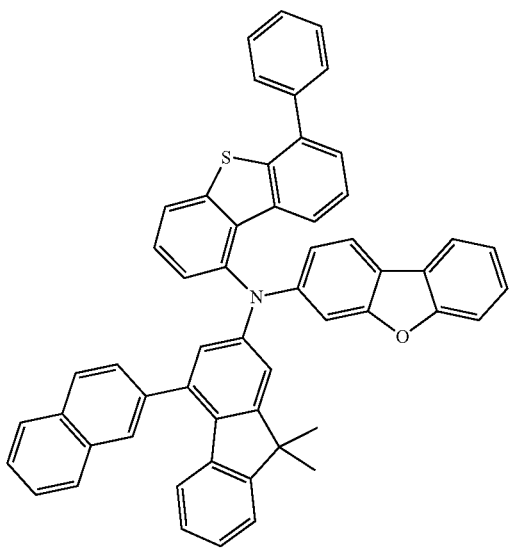
P2-30
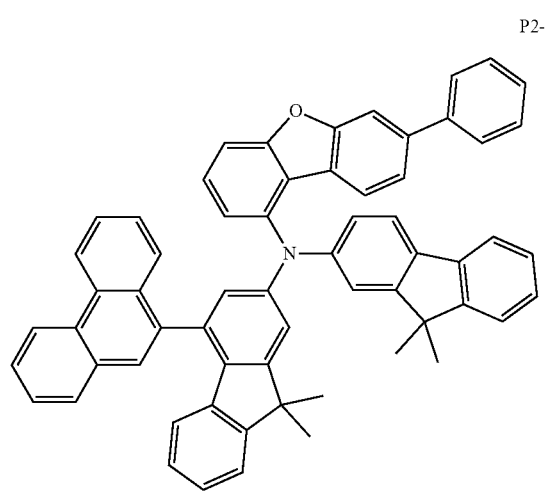
P2-31
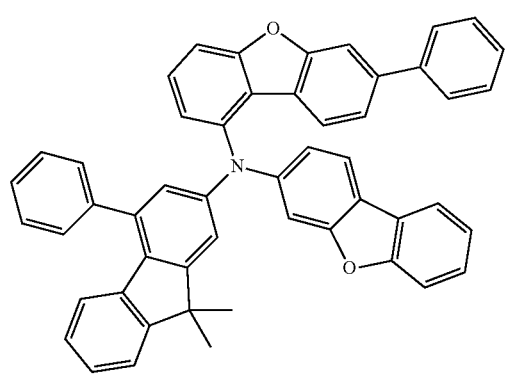
P2-32
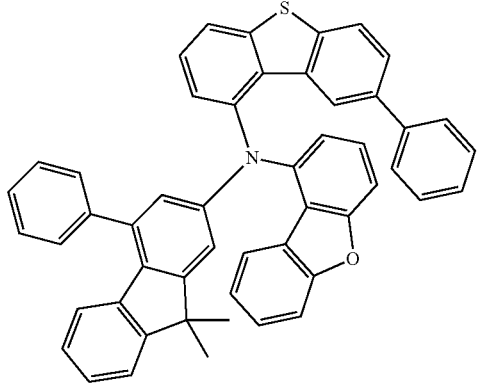
P2-33
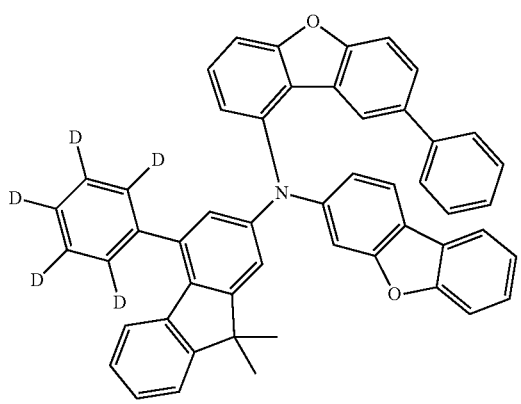
P2-34
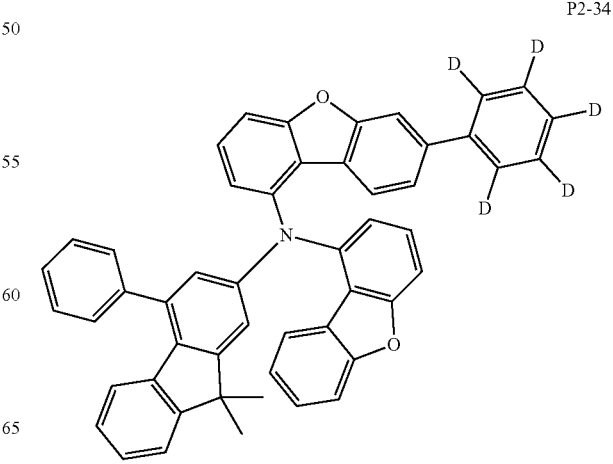

P2-35
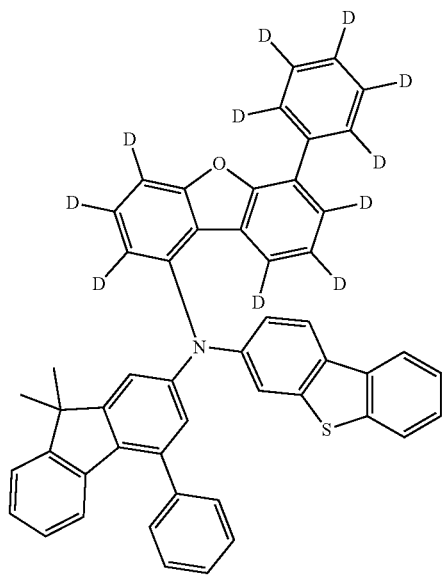
P2-36
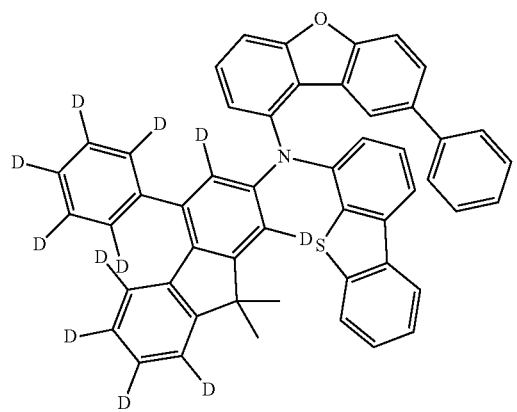
P2-37
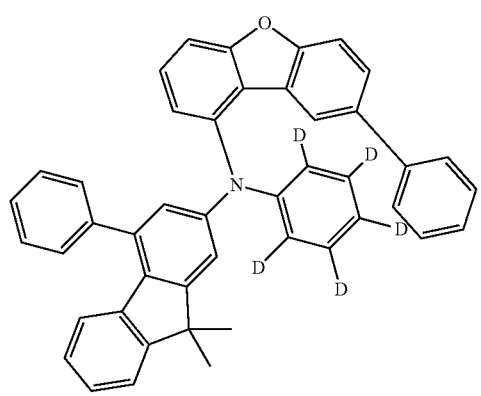
P2-38
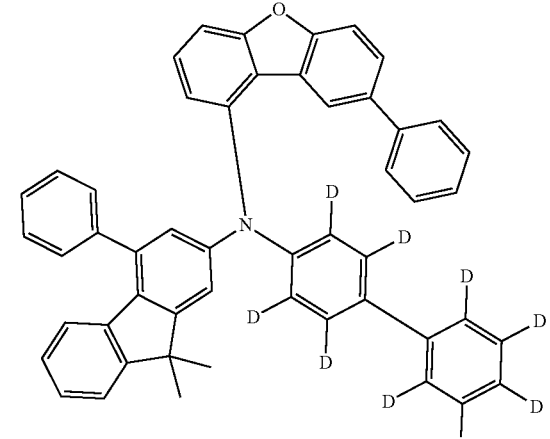
P2-39
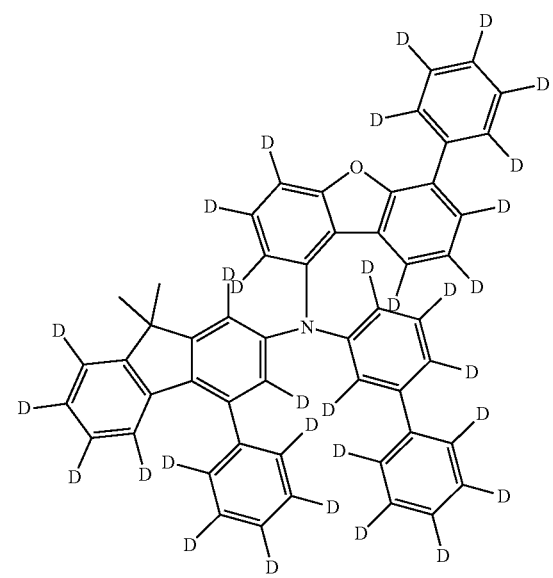
P2-40
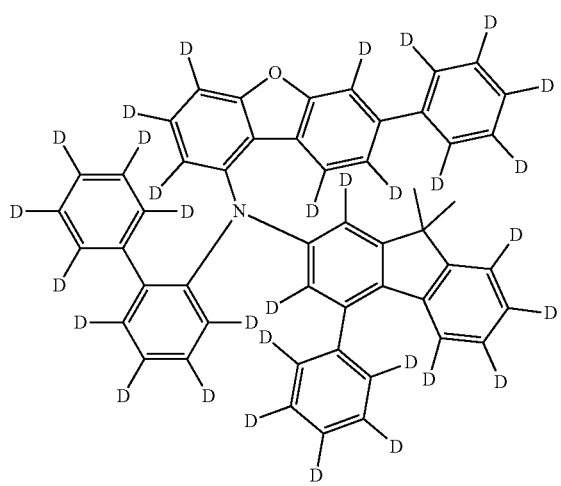

P2-41
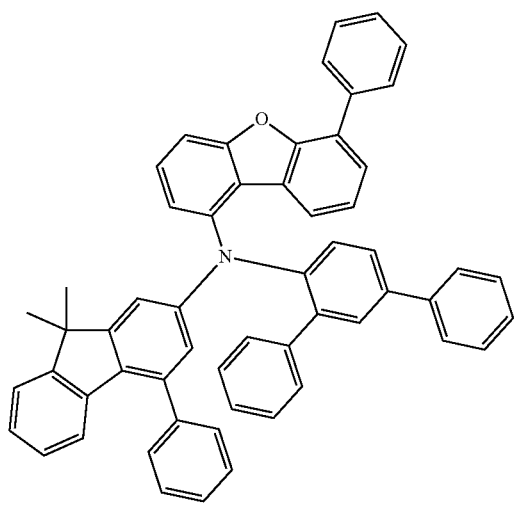
P2-42
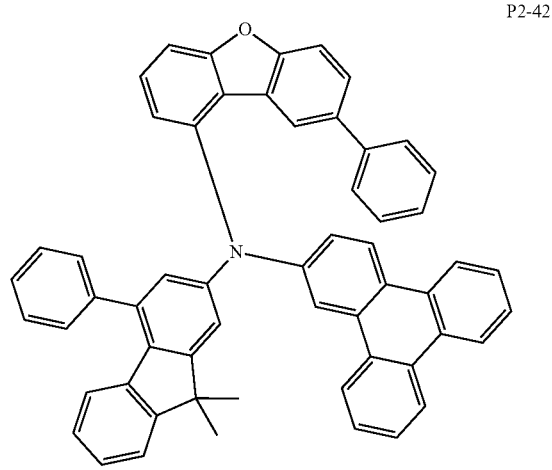
P2-43
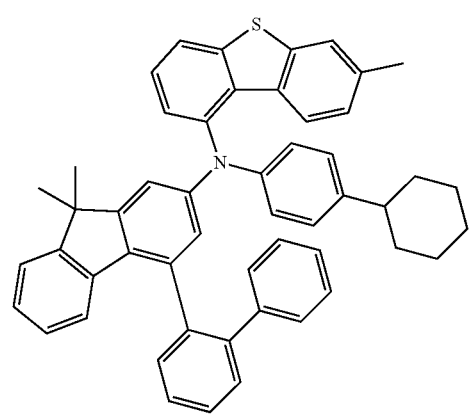
P2-44
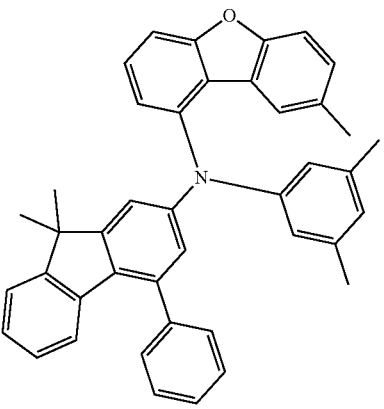
P2-45
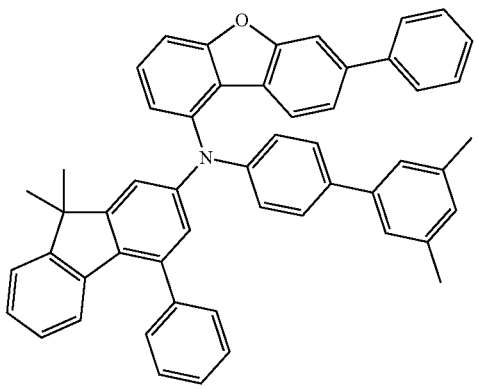
P2-46
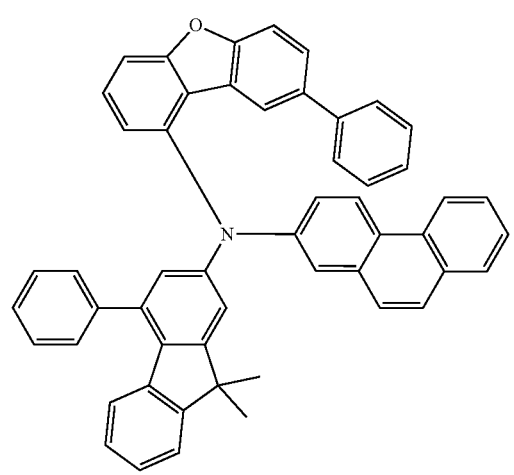

P2-47
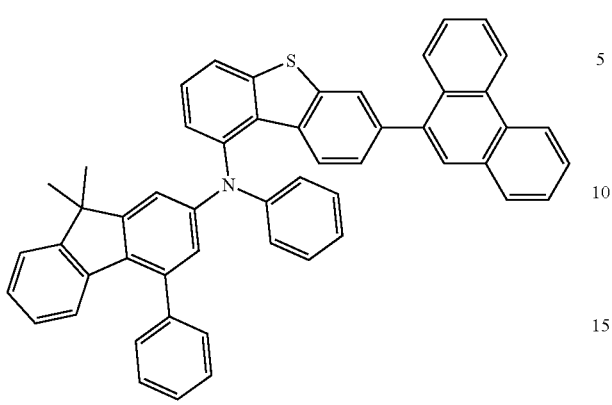
P2-48
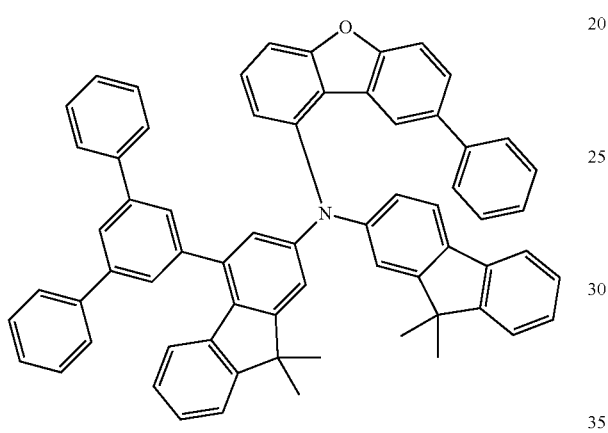
P2-49
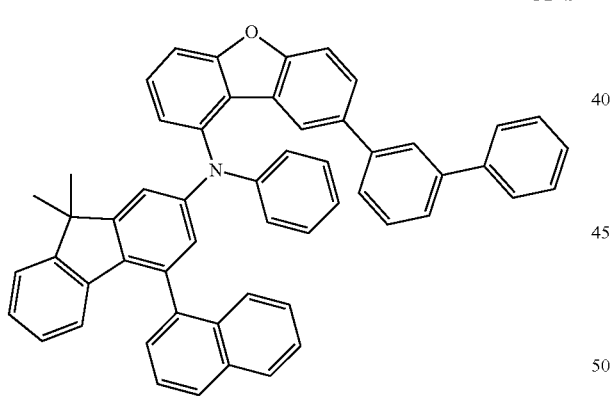
P2-50
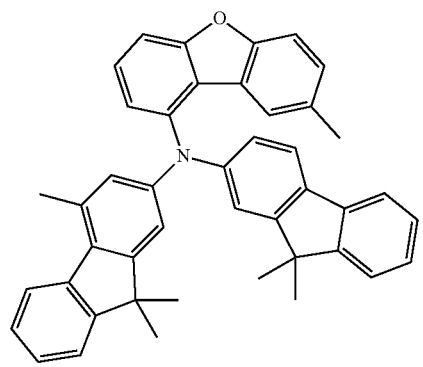
P2-51
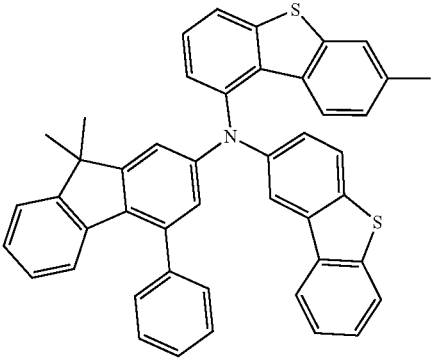
P2-52
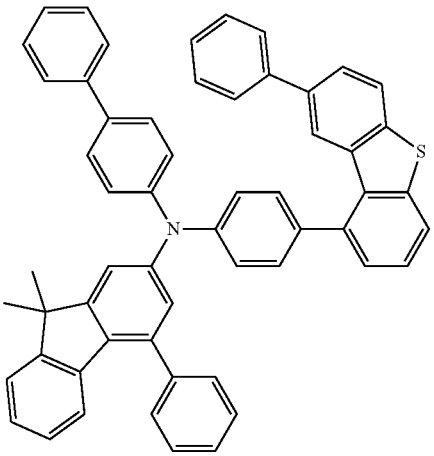
P2-53
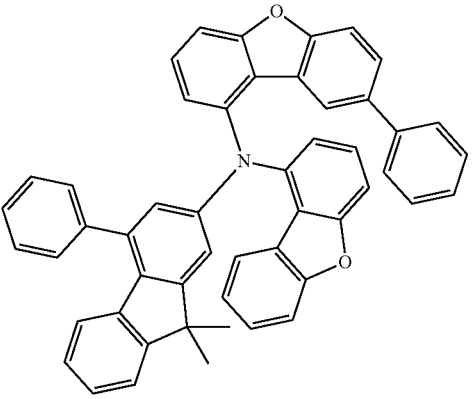
P2-54
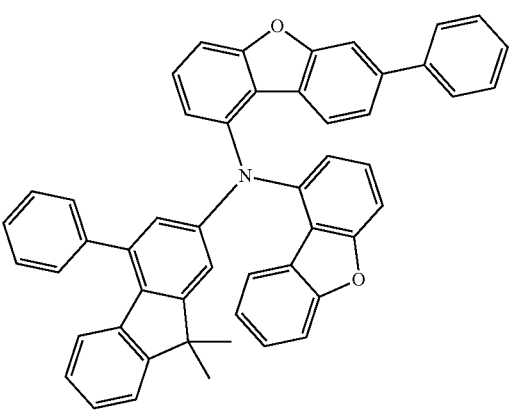

-continued

P2-55

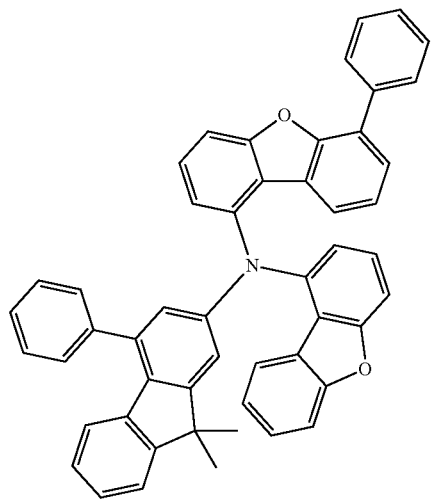

P2-56

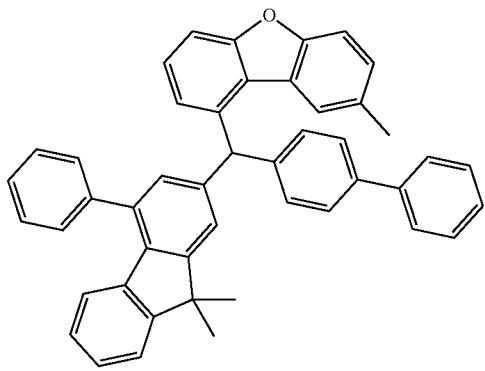

In another aspect, the present invention provides a method for reusing a compound by Formula (1-10) comprising:
recovering a crude organic light emitting material comprising the compound represented by Formula (1-10) from a deposition apparatus used in the process for depositing the organic emitting material to prepare an organic an organic light emitting device;
removing impurities from the crude organic light emitting material;
recovering the organic light emitting material after the impurities are removed; and
purifying the recovered organic light emitting material to have a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may preferably be used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N,N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification.

Referring to FIG. 1, the organic electronic element (100) according to the present invention comprises a first electrode (110), a second electrode (170), an organic material layer comprising single compound or 2 or more compounds represented by Formula (1) between the first electrode (110) and the second electrode (170). Here, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
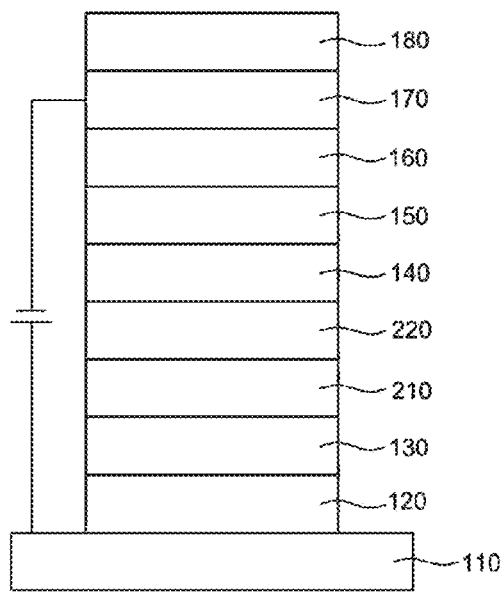

The organic material layer may sequentially comprise a hole injection layer (120), a hole transport layer (130), an emitting layer (140), an electron transport layer (150), and an electron injection layer (160) formed in sequence on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound or materials for organic electronic element according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), or the light efficiency enhancing layer. Preferably, for example, the compound according to Formula (1) of the present invention can be used as a material for the emitting-auxiliary layer.

Figure 3:
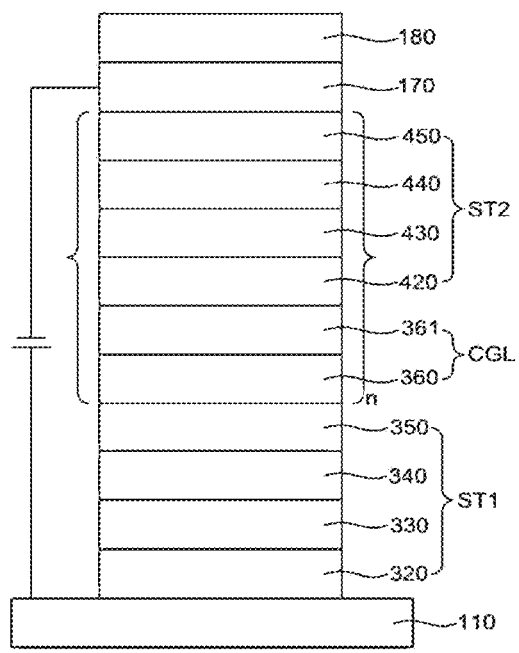
Figure 4:
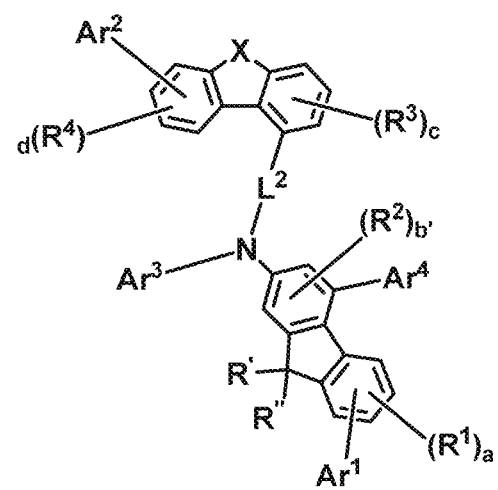
FIG. 4 shows a Formula according to one aspect of the present invention.

The organic material layer may include 2 or more stacks comprising a hole transport layer, an emitting layer, and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element that is used by mixing the same or different compounds of the compound represented by Formula (1-10) to the organic material layer.

Also, the present invention provides a composition for an emitting-auxiliary layer comprising the compound represented by Formula (1-10), and provides an organic electronic element comprising the emitting-auxiliary layer.

Also, the present invention also provides an electronic device comprising a display device comprising the organic electronic element; and a control unit for driving the display device.

According to another aspect, the present invention provides a display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Meanwhile, bond-dissociation energy is the calculated bond energy for acyclic bonds within a molecule. To this end, the electric potential energy of the target molecule is calculated, and the molecule is divided into 2 radical molecules based on the acyclic bond, and the electric potential energy for each is calculated, and the bond-dissociation energy can be expressed as follows.

$$E_{BD} = E_A^{rad} + E_B^{rad} - E_{AB}^{mol}$$

All calculations are conducted assuming electrical neutrality. Since solid-phase molecules extracted through molecular dynamics simulation do not have an optimized structure, unlike gas-phase molecules, all calculations are performed using single-point energy (SPE) calculations to calculate bond dissociation energy while maintaining the structure.

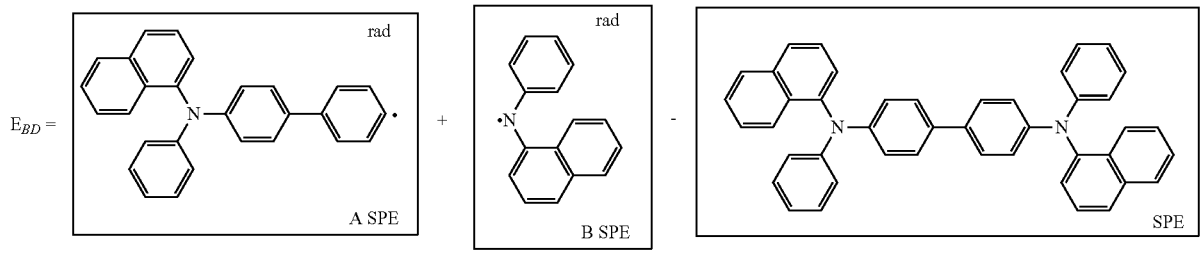

The term "Average bond-dissociation energy in solid state amorphous" used in this description refers to the Quantum-Mechanics-based Average Bond-dissociation Energy of Molecules in Molecular Dynamically simulated solid-state amorphous, unless otherwise specified.

Since the average bond-dissociation energy in solid state amorphous is a statistical data set (a set of multiple energy values), its value may be quantified differently depending on the data processing method. Therefore, in this description, for quantification, the value of Average bond-dissociation energy in solid state amorphous was used, which has high statistical reliability due to the large number of samples and clearly shows differences in properties between materials, and the value was obtained through the following process.

The average Bond-dissociation energy in solid-state amorphous is a value derived by placing a certain number of single molecules in a unit cell with periodic boundary conditions (PBC) and performing molecular dynamics simulation on them. Preferably, the number of single molecules in a unit cell may be tens to thousands.

The molecular dynamics simulation was conducted in 4 steps, and the first step was conducted at a temperature of 10 Kelvin under conditions of constant volume according to Brownian dynamics. The second step is similarly carried out according to Brownian dynamics, but at a temperature of 100 Kelvin under constant atmospheric pressure (1.01325 bar) conditions. In the third step, molecular dynamics according to the force field are calculated, and similarly, the process progresses for 0.1 nanosecond (ns) at constant pressure (atmospheric pressure) and temperature (room temperature). Finally, the molecular dynamics process is performed in units of 2 femtoseconds (fs) under the same conditions as the third step (atmospheric pressure, room temperature), and the simulation is performed until a certain amount of time is elapsed. Wherein, the certain amount of time refers to the time for the amorphous solid structure to reach an equilibrium state, preferably, it may be hundreds of nanoseconds to thousands of nanoseconds, more preferably 100 nanoseconds to 150 nanoseconds, and even more preferably 120 nanoseconds. Afterwards, the structural data at the final point is extracted and some single molecules are extracted (sampled) from the structure. Single-point energy calculation for single molecules extracted through Quantum Mechanics simulation was performed, and bond-dissociation energy (BDE) for acyclic bonds in the molecule was calculated. All the obtained values of the bond-dissociation energy are taken to form a bond-dissociation energy set $G=\{E_1 \ldots E_N\}$, and the average value E of the bond-dissociation energy set is used as an indicator of the bond-dissociation energy of the solid-state material.

In this description, the unit of value E of the average bond-dissociation energy in solid-state amorphous is eV, and the eV value can be multiplied by 23.061 to convert to kcal/mol.

As used herein, the term "Bulk density of solid-state amorphous" refers to the bulk density of molecular dynamically simulated solid-state amorphous obtained through molecular dynamics simulation, unless otherwise specified, and finding its value proceeds through the following process.

It is a value derived by placing a certain number of single molecules in a unit cell with periodic boundary conditions (PBC) and performing molecular dynamics simulation on them, preferably, the number of single molecules in a unit cell may be tens to thousands.

The molecular dynamics simulation was conducted in 4 steps, and the first step was conducted at a temperature of 10 Kelvin under conditions of constant volume according to Brownian dynamics. The second step is similarly carried out according to Brownian dynamics, but at a temperature of 100 Kelvin under constant atmospheric pressure (1.01325 bar) conditions. In the third step, molecular dynamics according to the force field are calculated, and similarly, the process progresses for 0.1 nanosecond (ns) at constant pressure (atmospheric pressure) and temperature (room temperature). Finally, the molecular dynamics process is performed in units of 2 femtoseconds (fs) under the same conditions as the third step (atmospheric pressure, room temperature), and the simulation is performed until a certain amount of time is elapsed. Wherein, the certain amount of time refers to the time for the amorphous solid structure to reach an equilibrium state, preferably, it may be hundreds of nanoseconds to thousands of nanoseconds, more preferably 100 nanoseconds to 150 nanoseconds, and even more preferably 120 nanoseconds. Afterwards, the average bulk density for the final 20% of the time was calculated, wherein the final 20% of the time may preferably be tens of nanoseconds to thousands of nanoseconds, more preferably 80 nanoseconds to 150 nanoseconds, and even more preferably 120 nanoseconds.

In this description, the unit of value of Bulk density of solid-state amorphous is $g/cm^3$.

The term "Radial Distribution Function (RDF) g(r)" used in the description refers to the probability of discovering another molecule that is a certain distance r away from one molecule. The radial distribution function is expressed as a function according to distance, and the equation is defined as follows.

$$g(r) = \frac{dn_r}{4\pi r^2 dr * \rho}$$

In the above formula, p is the bulk density, dr is the micro-thickness of a sphere with radius r, $dn_r$ is the number of molecules included in the shell of a sphere with a micro-thickness of dr. In order to quantify the radial distribution function, the distance at which the radial distribution function has the largest value in solid-state amorphous is used as an indicator, wherein the distance r between molecules was used as the center-of-mass distance of each molecule. The solid-state amorphous structure to obtain the radial distribution function is obtained through molecular dynamical simulation. Wherein, the distribution function was calculated using only the structure for the final 20% of the total simulation time, wherein the final 20% of time may preferably be tens of nanoseconds to thousands of nanoseconds, more preferably 80 nanoseconds to 150 nanoseconds, and even more preferably 120 nanoseconds.

In the description, the unit of value of the radial distribution function is A.

The values of the average bond-dissociation energy in solid-state amorphous and the bulk density of solid-state amorphous and radial distribution function described in the description were obtained through molecular simulation (Gaussian09 Rev. C.01, Schrodinger Materials Science Suite 4.1.161), and the Desmond package was used for the molecular dynamics simulation. A single molecule was extracted from the structure obtained through molecular dynamical simulation and quantum chemical properties were calculated based on first principles, and in this process, Gaussian and Jaguar packages were used.

Charge mobility can be obtained from the analytical solution of the Master equation according to the effective medium approximation for a uniform medium in the generalized effective medium model (GEMM), and the equation is expressed as follows.

$$\mu = \frac{e\beta M <H_{ab}>}{n\hbar\sqrt{\lambda}} \sqrt{\frac{\pi\beta}{1+\frac{\beta\sigma^2}{\lambda}}} \exp[-C((\beta\sigma)^2 - \beta\lambda)]$$

Wherein e is the charge, $\beta$ is the thermodynamic constant given by the Boltzmann constant and the reciprocal of temperature $(1/k_B T)$, M is the average number of nearest-neighbor molecules, $H_{ab}$ is a charge transfer matrix element, n is the charge transfer dimension (n=3 in 3D), $\hbar$ is Planck's constant, $\lambda$ is Reorganization energy, $\sigma$ is the disorder parameter, C is the correction constant. Therefore, charge mobility has the following proportional relationship.

$$\mu \propto \frac{<H_{ab}^2>}{\sqrt{\lambda + \beta\sigma^2}} \exp(-\beta\lambda)$$

Assuming that the molecules in solid-state amorphous are sufficiently uniformly distributed ($\sigma \ll 1$), since the charge transfer matrix element ($H_{ab}$) between each dimer is constant, the above proportional equation can be expressed as follows.

$$\mu \propto \frac{H_{ab}^2}{\sqrt{\lambda}} \exp(-\beta \lambda)$$

Here, it is known a priori that the charge transfer matrix elements have the following proportional relationship with the intermolecular distance.

$$H_{ab} \propto \exp\left(-\frac{\eta}{2}r\right)$$

wherein, $\eta$ is the decay constant and r is the distance between molecules. Therefore, for a uniform medium, charge mobility has an exponential attenuation proportional relationship with the distance between molecules, and as the distance between molecules becomes shorter, charge mobility tends to increase.

Additionally, since the volume density is inversely proportional to the volume ($\rho \propto 1/V$), the average intermolecular distance ($\sqrt[3]{1/V}$) can be derived using this, and the smaller the volume density, the shorter the distance between molecules, which means that materials with a low volume density can have high charge mobility.

Therefore, by examining the radial distribution function of structure in Molecular Dynamically simulated solid-state amorphous, the distribution section where the intermolecular distance is maximally dense can be confirmed, the location of the peak value of the radial distribution function can be used as an indicator of the distance between molecules to compare charge mobility.

For the above charge mobility, reference is made to document [Friederich, Pascal, et al. "Ab initio treatment of disorder effects in amorphous organic materials: Toward parameterfree materials simulation", Journal of chemical theory and computation 10.9 (2014): 3720-3725], [Friederich, Pascal, et al. "Molecular origin of the charge carrier mobility in small molecule organic semiconductors", Advanced Functional Materials 26.31 (2016): 5757-5763], [Oberhofer, Harald, and Jochen Blumberger. "Electronic coupling matrix elements from charge constrained density functional theory calculations using a plane wave basis set", The Journal of Chemical Physics 133.24 (2010): 244105], [Albinsson, Bo, et al. "Electron and energy transfer in donor-acceptor systems with conjugated molecular bridges", Physical Chemistry Chemical Physics 9.44 (2007): 5847-5864] and [Cave, Robert J., and Marshall D. Newton. "Calculation of electronic coupling matrix elements for ground and excited state electron transfer reactions: comparison of the generalized Mulliken-Hush and block diagonalization methods", The Journal of chemical physics 106.22 (1997): 9213-9226], which is hereby incorporated by reference in its entirety.

Hereinafter, Synthesis examples of the compound represented by Formula (1-10) and preparation examples of the organic electronic element of the present invention will be described in detail by way of example, but are not limited to the following examples.

EXAMPLES

Synthesis Example

The compound (final products) represented by Formula (1-10) according to the present invention is synthesized by reacting Sub1 and Sub 2 as shown in Reaction Scheme 1, but is not limited thereto.

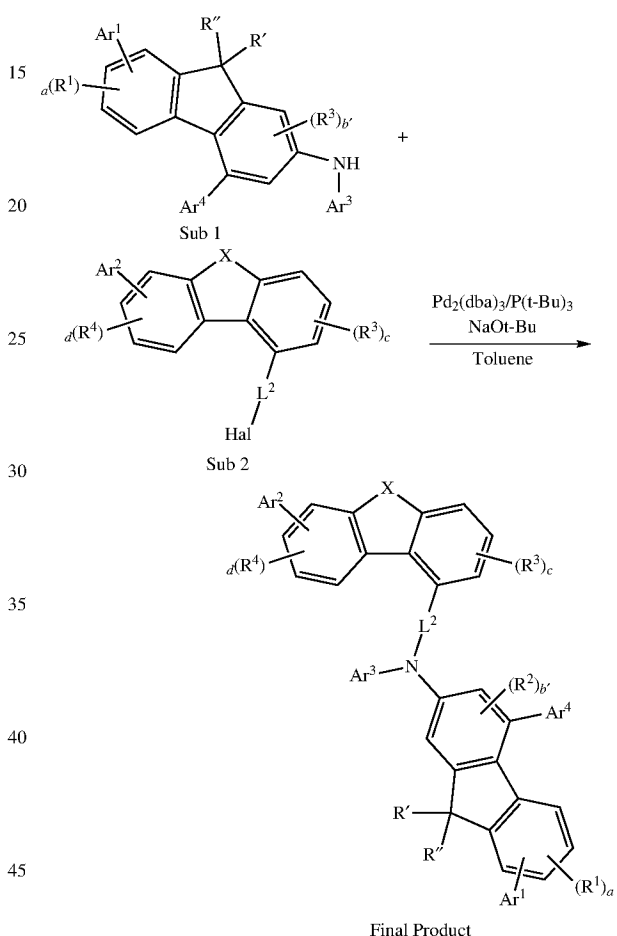

It is the same as defined in Formula (1-10).

I. Synthesis of Sub 1

Sub 1 of Reaction Scheme 1 may be synthesized through the reaction route of Reaction Scheme 2, but is not limited thereto.

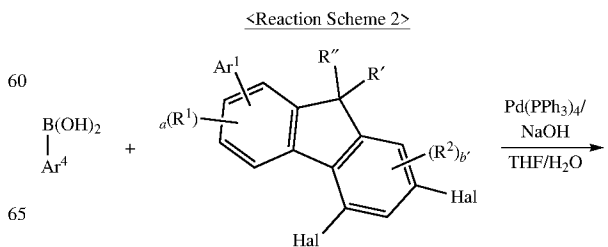

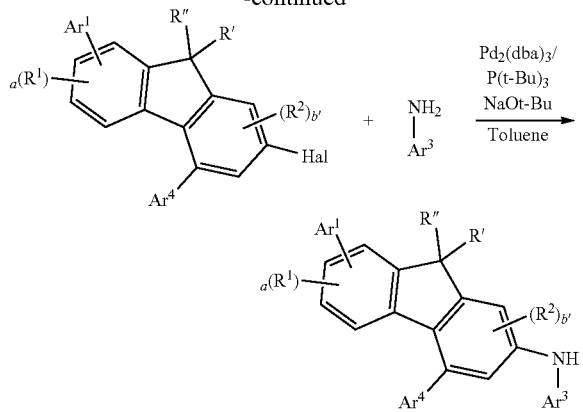

Synthesis examples of specific compounds belonging to Sub 1 are as follows.

Synthesis Example of Sub 1-140

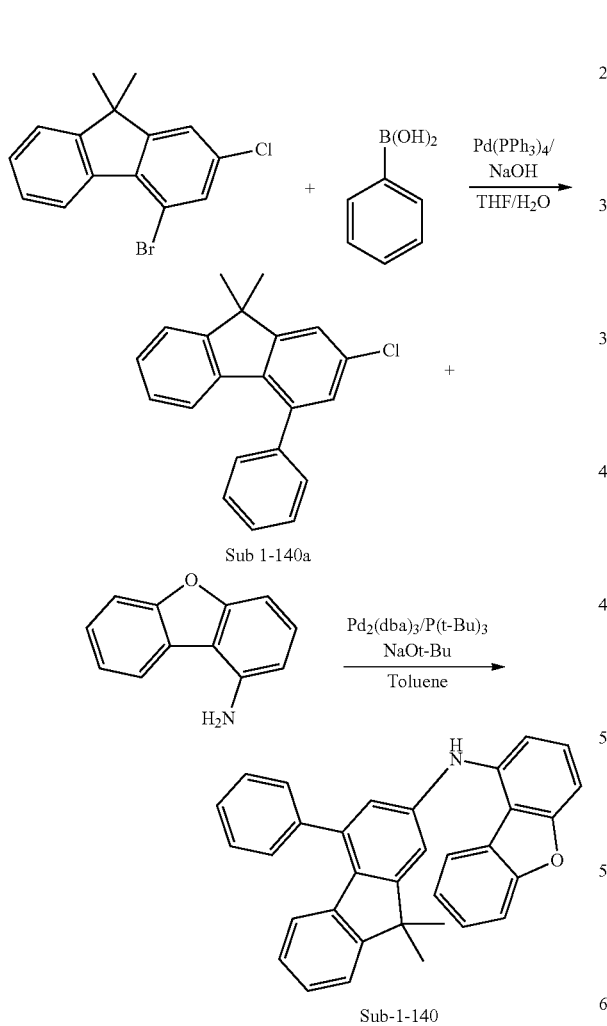

Sub-1-140

(1) Synthesis of Sub 1-140a

After dissolving 4-bromo-2-chloro-9,9-dimethyl-9H-fluorene (30.0 g, 97.53 mmol) in THF (240 mL) in a round bottom flask, phenylboronic acid (11.89 g, 97.53 mmol), Pd(PPh$_3$)$_4$ (3.38 g, 2.93 mmol), NaOH (7.8 g, 195.05 mmol), and 80 mL of water were added and stirred at 80° C. When the reaction was completed, extracted with CH$_2$Cl$_2$ and water, the organic layer was dried over MgSO$_4$ and concentrated, and the resulting compound was recrystallized using a silica gel column to obtain 22 g of product (yield: 74%).

(2) Synthesis of Sub 1-140

The obtained Sub 1-140a (22 g, 72.17 mmol) was placed in a round bottom flask and dissolved in 240 mL of Toluene, then dibenzo[b,d]furan-1-amine (13.22 g, 72.17 mmol)와 Pd$_2$(dba)$_3$ (1.98 g, 2.17 mmol), P(t-Bu)$_3$ (0.88 g, 4.33 mmol), NaOt-Bu (13.87 g, 144.35 mmol) were added and stirred at room temperature. When the reaction was completed, extracted with Toluene and water, the organic layer was dried over MgSO$_4$ and concentrated, and the resulting compound was recrystallized using a silica gel column to obtain 25.5 g of product (yield: 78%).

Synthesis Example of Sub 1-151

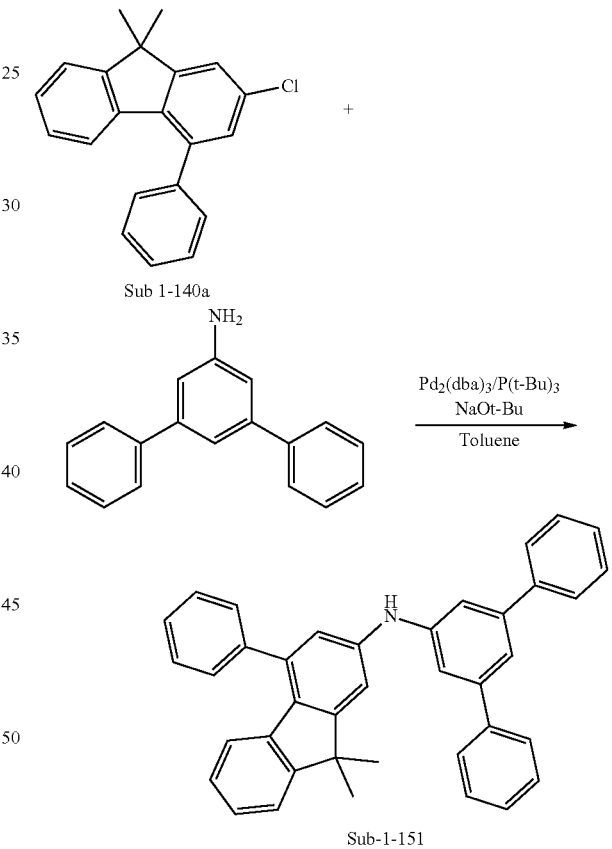

Sub-1-151

(1) Synthesis of Sub 1-151

Sub 1-140a (20.0 g, 65.61 mmol) was placed in a round bottom flask and dissolved in 220 mL of Toluene, then [1,1':3',1''-terphenyl]-5'-amine (16.10 g, 65.61 mmol)와 Pd$_2$(dba)$_3$ (1.80 g, 1.97 mmol), P(t-Bu)$_3$ (0.80 g, 3.94 mmol), NaOt-Bu (12.61 g, 131.22 mmol) were added and stirred at room temperature. When the reaction was completed, extracted with Toluene and water, the organic layer was dried over MgSO$_4$ and concentrated, and the resulting compound was recrystallized using a silica gel column to obtain 25.5 g of product (yield: 75%).

Synthesis Example of Sub 1-164

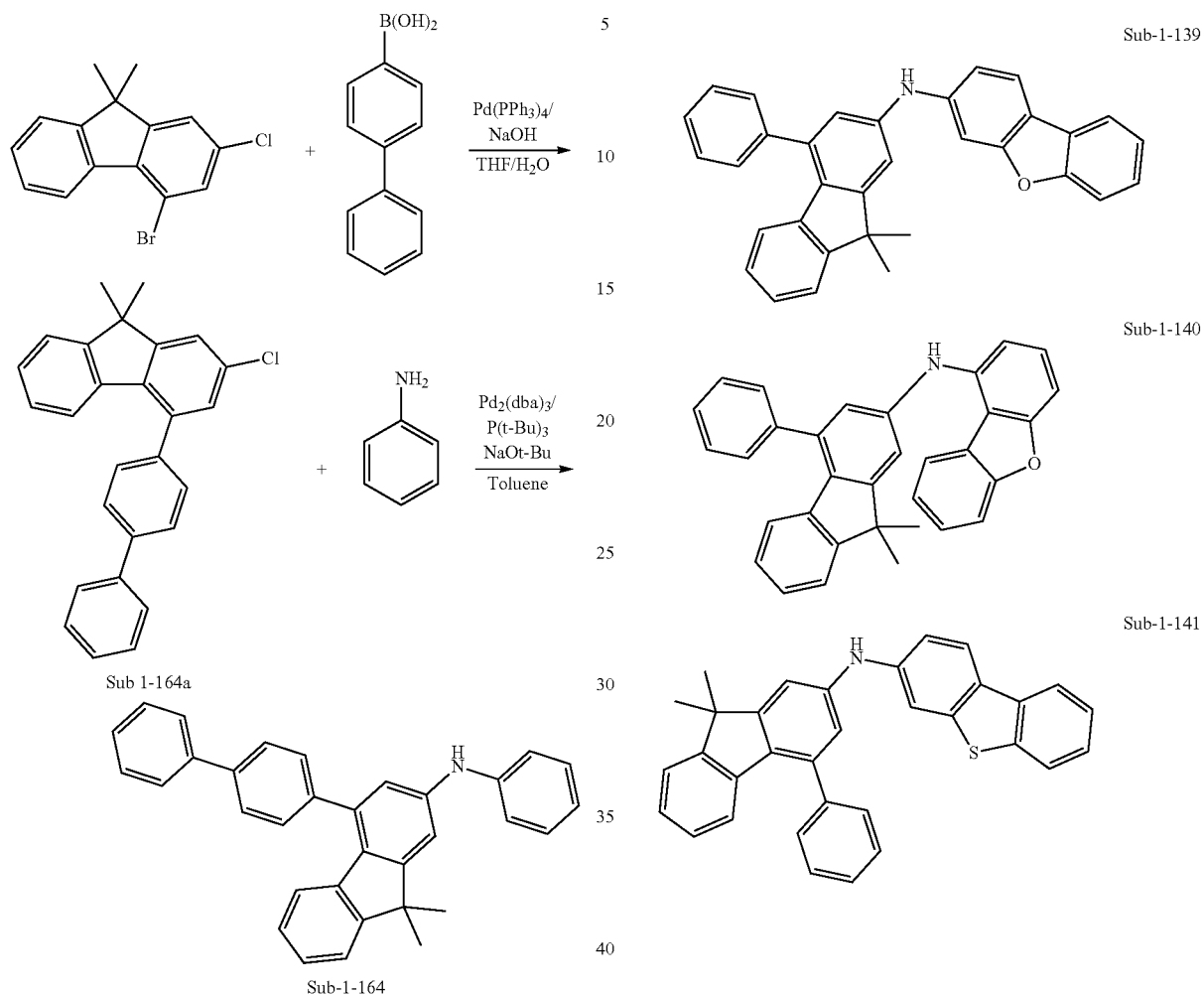

Examples of Sub 1 are as follows, but are not limited thereto.

(1) Synthesis of Sub 1-164a

After dissolving 4-bromo-2-chloro-9,9-dimethyl-9H-fluorene (30.0 g, 97.53 mmol) in THE (325 mL) in a round bottom flask, [1,1'-biphenyl]-4-ylboronic acid (19.31 g, 97.53 mmol), Pd(PPh$_3$)$_4$ (3.38 g, 2.93 mmol), NaOH (7.8 g, 195.05 mmol), and 80 mL of water were added and stirred at 80° C. When the reaction was completed, extracted with CH$_2$C$_{12}$ and water, the organic layer was dried over MgSO$_4$ and concentrated, and the resulting compound was recrystallized using a silica gel column to obtain 29.8 f product (yield: 80%).

(2) Synthesis of Sub 1-164

Sub 1-164a (29.8 g, 78.23 mmol) was placed in a round bottom flask and dissolved in 261 mL of Toluene, then aniline (7.29 g, 78.23 mmol)과 Pd$_2$(dba)$_3$ (2.15 g, 2.35 mmol), P(t-Bu)$_3$ (0.95 g, 4.69 mmol), NaOt-Bu (15.04 g, 156.47 mmol) were added and stirred at room temperature. When the reaction was completed, extracted with Toluene and water, the organic layer was dried over MgSO$_4$ and concentrated, and the resulting compound was recrystallized using a silica gel column to obtain 29 g of product (yield: 84%).

Sub-1-144
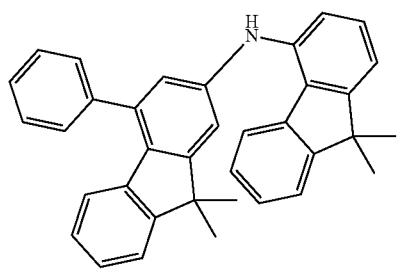
Sub-1-145
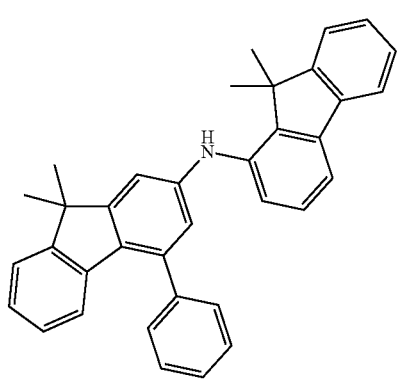
Sub-1-146
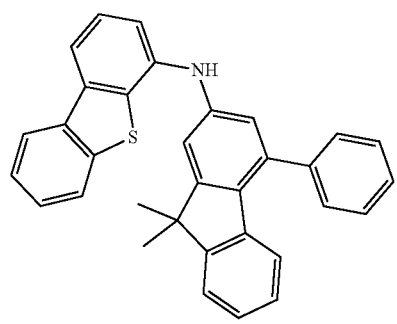
Sub-1-147
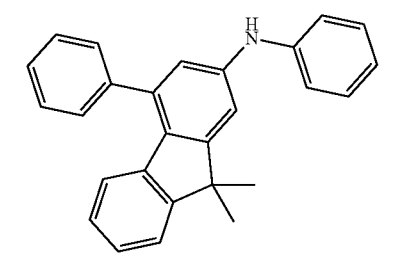
Sub-1-148
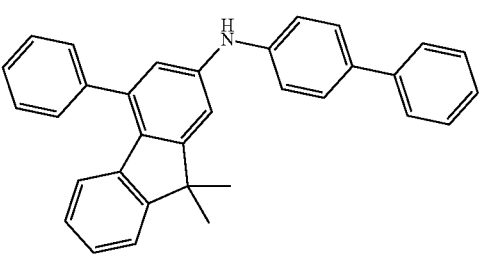
Sub-1-149
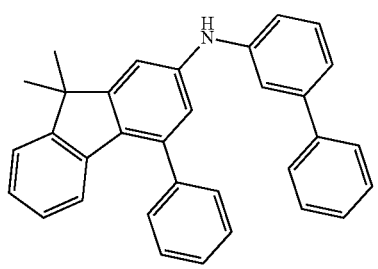
Sub-1-150
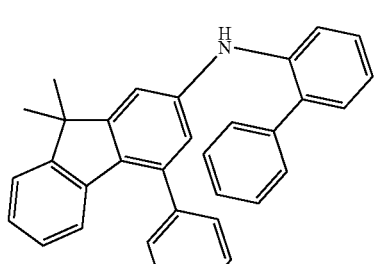
Sub-1-151
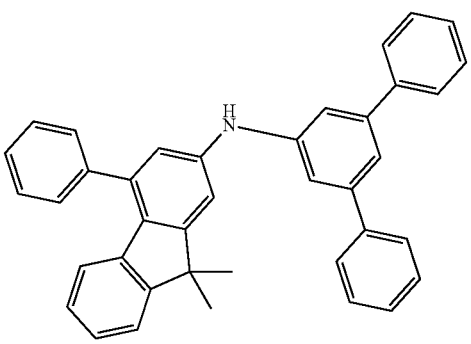
Sub-1-152
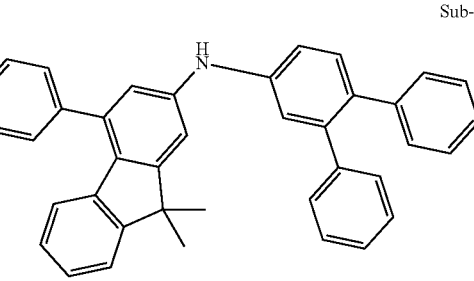
Sub-1-153
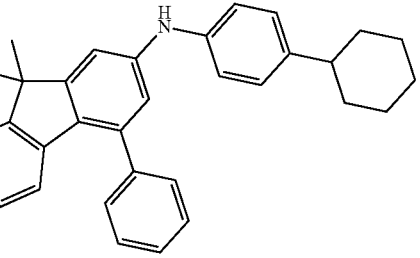

Sub-1-154
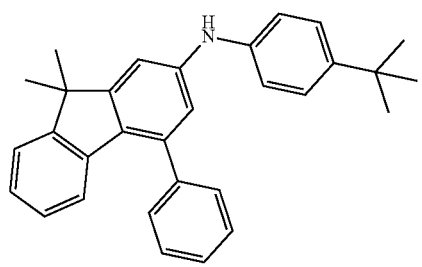
Sub-1-159
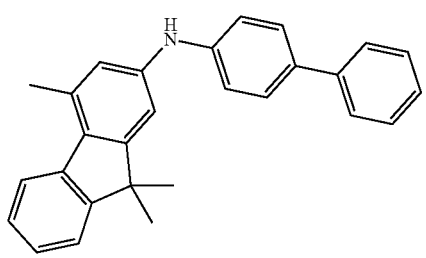
Sub-1-155
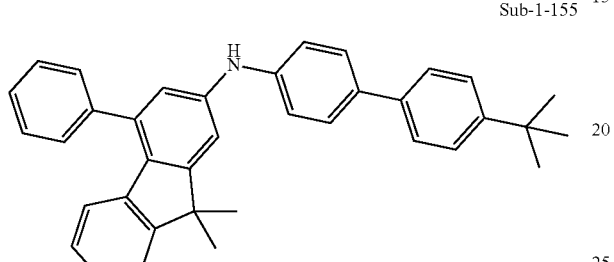
Sub-1-160
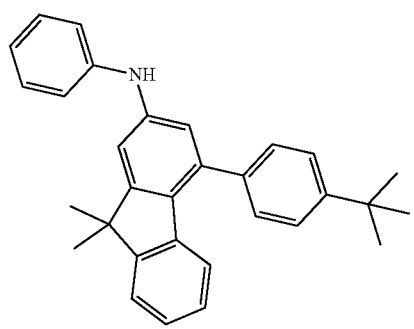
Sub-1-156
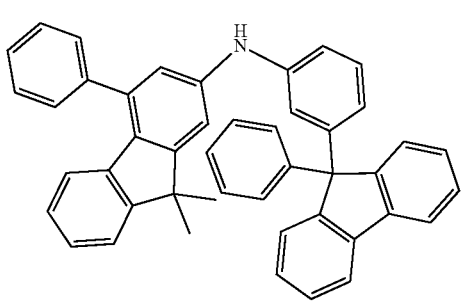
Sub-1-161
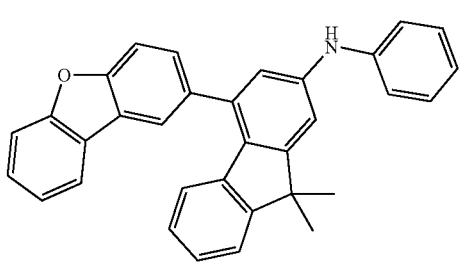
Sub-1-157
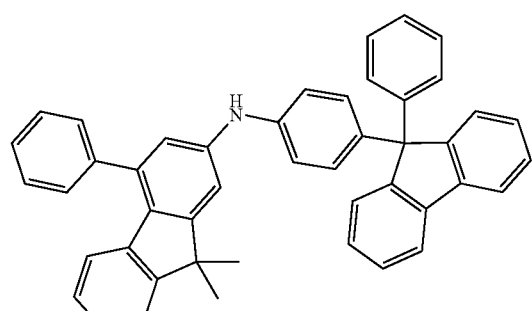
Sub-1-162
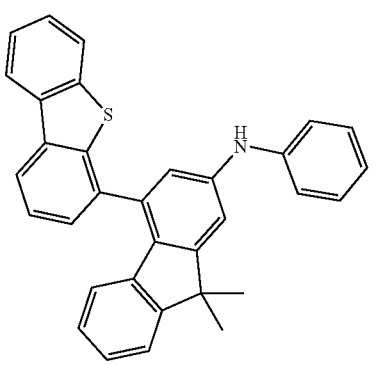
Sub-1-158
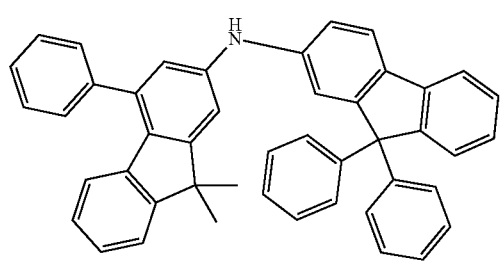
Sub-1-163
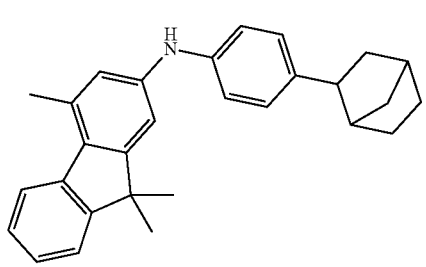

-continued
Sub-1-164
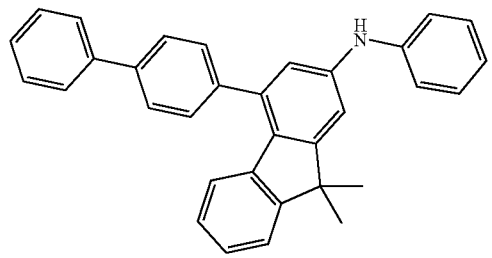
Sub-1-165
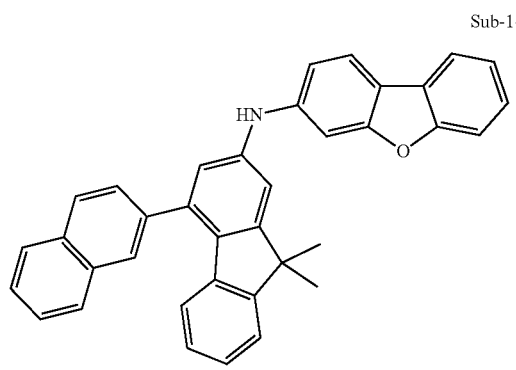
Sub-1-166
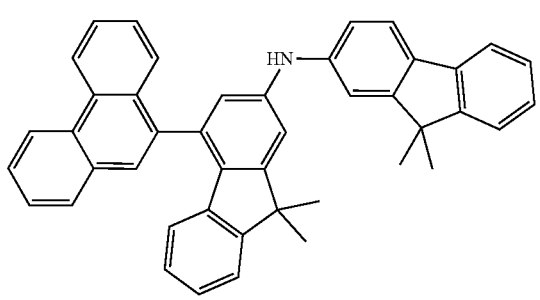
Sub-1-167
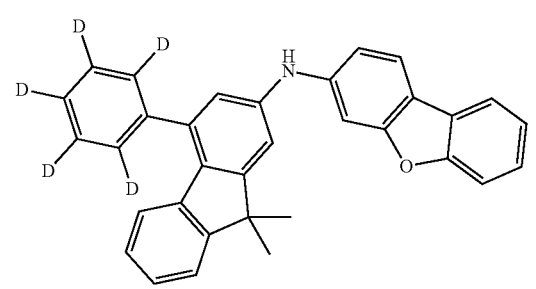
Sub-1-168
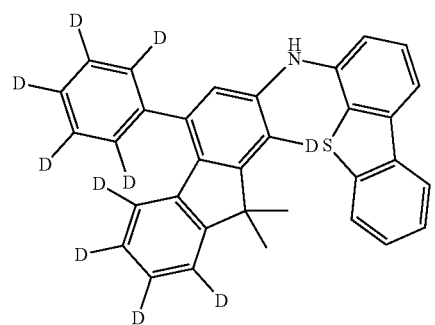
-continued
Sub-1-169
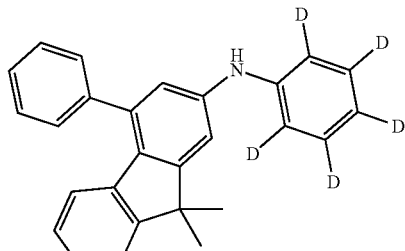
Sub-1-170
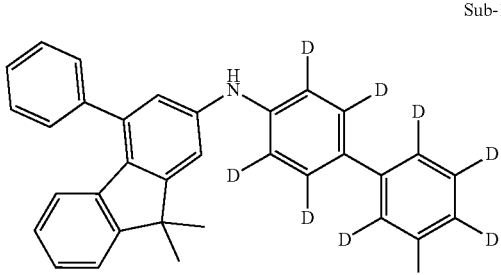
Sub-1-171
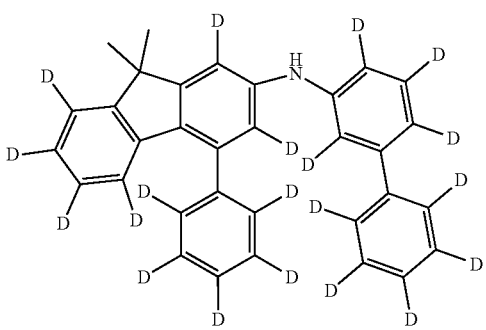
Sub-1-172
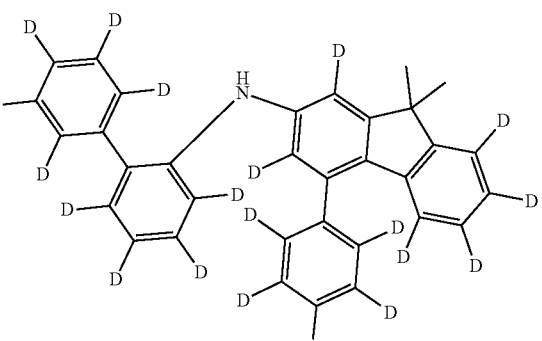
Sub-1-173
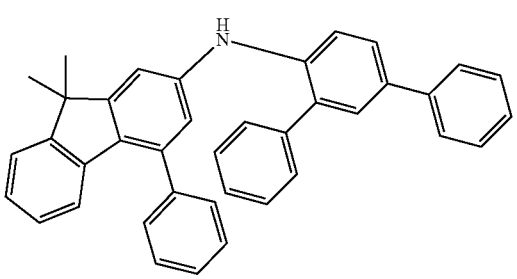

Sub-1-174
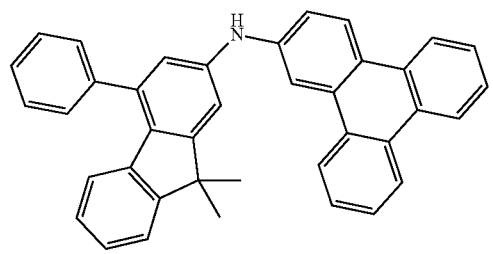
Sub-1-179
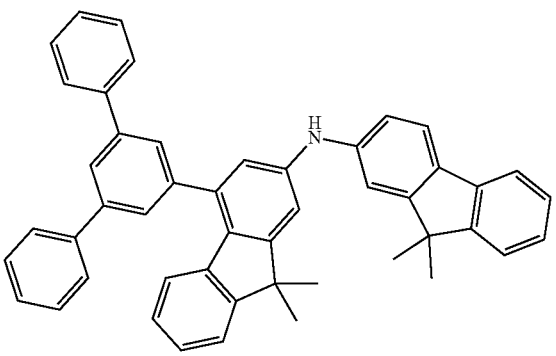
Sub-1-175
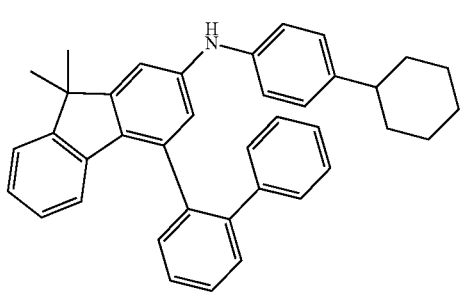
Sub-1-180
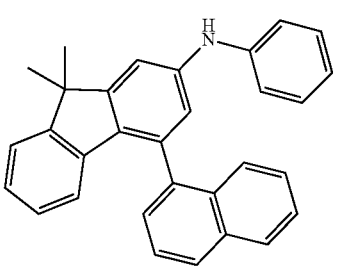
Sub-1-176
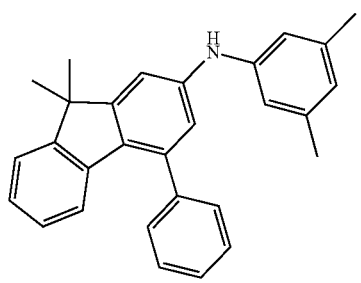
Sub-1-181
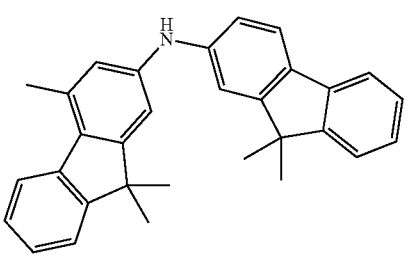
Sub-1-177
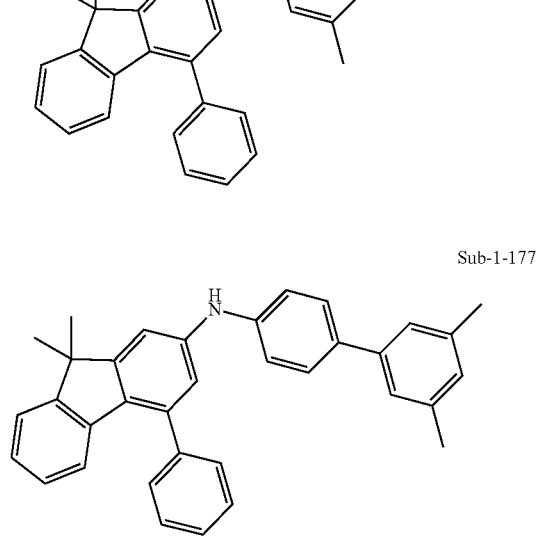
Sub-1-182
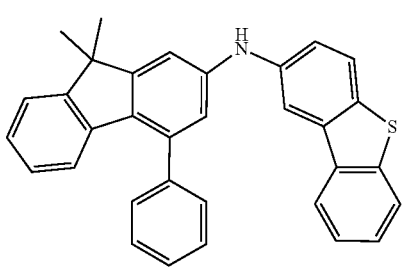
Sub-1-178
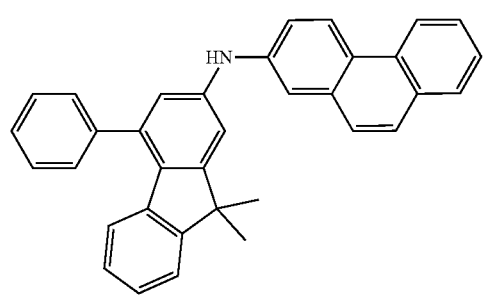
Sub-1-183
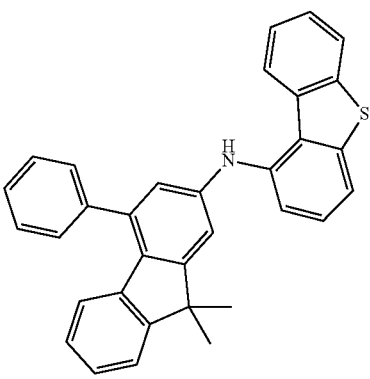

TABLE 1

| compound | FD-MS | compound | FD-MS |
|---|---|---|---|
| Sub 1-139 | m/z = 451.19 ($C_{33}H_{25}NO$ = 451.57) | Sub 1-140 | m/z = 451.19 ($C_{33}H_{25}NO$ = 451.57) |
| Sub 1-141 | m/z = 467.17 ($C_{33}H_{25}NS$ = 467.63) | Sub 1-142 | m/z = 467.17 ($C_{33}H_{25}NS$ = 467.63) |
| Sub 1-143 | m/z = 477.25 ($C_{36}H_{31}N$ = 477.65) | Sub 1-144 | m/z = 477.25 ($C_{36}H_{31}N$ = 477.65) |
| Sub 1-145 | m/z = 477.25 ($C_{36}H_{31}N$ = 477.65) | Sub 1-146 | m/z = 467.17 ($C_{33}H_{25}NS$ = 467.63) |
| Sub 1-147 | m/z = 361.18 ($C_{27}H_{23}N$ = 361.49) | Sub 1-148 | m/z = 437.21 ($C_{33}H_{27}N$ = 437.59) |
| Sub 1-149 | m/z = 437.21 ($C_{33}H_{27}N$ = 437.59) | Sub 1-150 | m/z = 437.21 ($C_{33}H_{27}N$ = 437.59) |
| Sub 1-151 | m/z = 513.25 ($C_{39}H_{31}N$ = 513.68) | Sub 1-152 | m/z = 513.25 ($C_{39}H_{31}N$ = 513.68) |
| Sub 1-153 | m/z = 443.26 ($C_{33}H_{33}N$ = 443.63) | Sub 1-154 | m/z = 417.25 ($C_{31}H_{31}N$ = 417.60) |
| Sub 1-155 | m/z = 493.28 ($C_{37}H_{35}N$ = 493.69) | Sub 1-156 | m/z = 601.28 ($C_{46}H_{35}N$ = 601.79) |
| Sub 1-157 | m/z = 601.28 ($C_{46}H_{35}N$ = 601.79) | Sub 1-158 | m/z = 601.28 ($C_{46}H_{35}N$ = 601.79) |
| Sub 1-159 | m/z = 375.20 ($C_{28}H_{25}N$ = 375.51) | Sub 1-160 | m/z = 417.25 ($C_{31}H_{31}N$ = 417.60) |
| Sub 1-161 | m/z = 451.19 ($C_{33}H_{25}NO$ = 451.57) | Sub 1-162 | m/z = 467.17 ($C_{33}H_{25}NS$ = 467.63) |
| Sub 1-163 | m/z = 393.25 ($C_{29}H_{31}N$ = 393.57) | Sub 1-164 | m/z = 437.21 ($C_{33}H_{27}N$ = 437.59) |
| Sub 1-165 | m/z = 501.21 ($C_{37}H_{27}NO$ = 501.63) | Sub 1-166 | m/z = 577.28 ($C_{44}H_{35}N$ = 577.77) |
| Sub 1-167 | m/z = 456.22 ($C_{33}H_{20}D_5NO$ = 456.60) | Sub 1-168 | m/z = 478.24 ($C_{33}H_{14}D_{11}NS$ = 478.70) |
| Sub 1-169 | m/z = 366.21 ($C_{27}H_{18}D_5N$ = 366.52) | Sub 1-170 | m/z = 446.27 ($C_{33}H_{18}D_9N$ = 446.64) |
| Sub 1-171 | m/z = 457.34 ($C_{33}H_7D_{20}N$ = 457.71) | Sub 1-172 | m/z = 457.34 ($C_{33}H_7D_{20}N$ = 457.71) |
| Sub 1-173 | m/z = 513.25 ($C_{39}H_{31}N$ = 513.68) | Sub 1-174 | m/z = 511.23 ($C_{39}H_{29}N$ = 511.67) |
| Sub 1-175 | m/z = 519.29 ($C_{39}H_{37}N$ = 519.73) | Sub 1-176 | m/z = 389.21 ($C_{29}H_{27}N$ = 389.54) |
| Sub 1-177 | m/z = 465.25 ($C_{35}H_{31}N$ = 465.64) | Sub 1-178 | m/z = 461.21 ($C_{35}H_{27}N$ = 461.61) |
| Sub 1-179 | m/z = 629.31 ($C_{48}H_{39}N$ = 629.85) | Sub 1-180 | m/z = 411.20 ($C_{31}H_{25}N$ = 411.55) |
| Sub 1-181 | m/z = 451.23 ($C_{31}H_{29}N$ = 415.58) | Sub 1-182 | m/z = 467.17 ($C_{33}H_{25}NS$ = 467.63) |
| Sub 1-183 | m/z = 467.17 ($C_{33}H_{25}NS$ = 467.63) | | |

II. Synthesis of Sub 2

Sub 2 of Reaction Scheme 1 may be synthesized by Reaction Scheme 3, but is not limited thereto.

<Reaction Scheme 3>

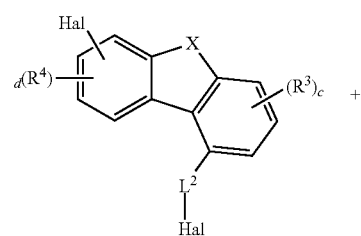
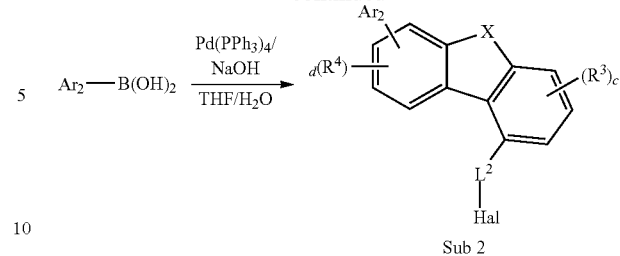

Examples of synthesis of specific compounds belonging to Sub 2 are as follows.

Synthesis Example of Sub 2-105

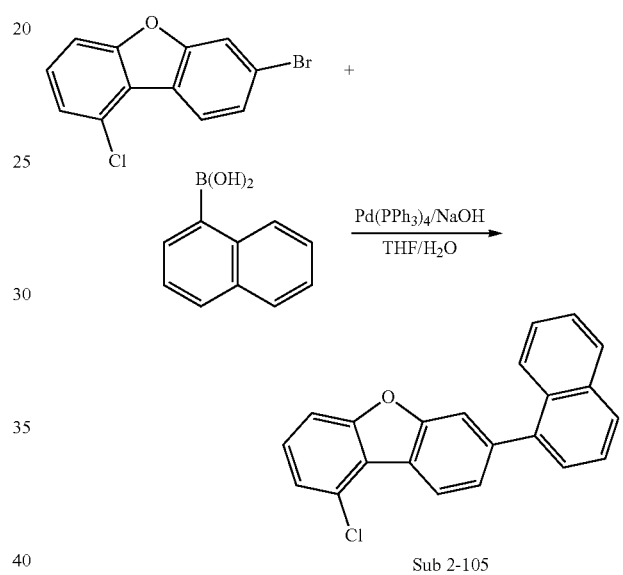

(1) Synthesis of Sub 2-105

After dissolving 7-bromo-1-chlorodibenzo[b,d]furan (35.0 g, 124.32 mmol) in 414 mL of THF in a round bottom flask, naphthalen-1-ylboronic acid (21.38 g, 124.32 mmol), Pd(PPh₃)₄ (4.31 g, 3.73 mmol), NaOH (9.94 g, 248.64 mmol), and 103.5 mL of water were added and stirred at 80° C. When the reaction was completed, extracted with $CH_2Cl_2$ and water, the organic layer was dried over $MgSO_4$ and concentrated, and the resulting compound was recrystallized using a silica gel column to obtain 32.3 g of product (yield: 79%).

Synthesis Example of Sub 2-109

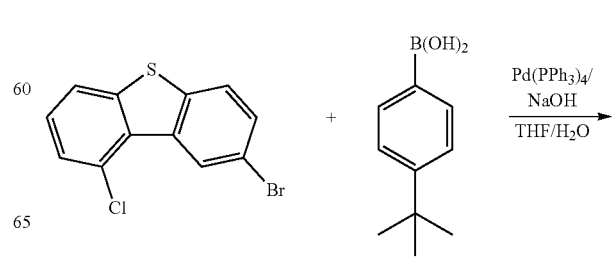

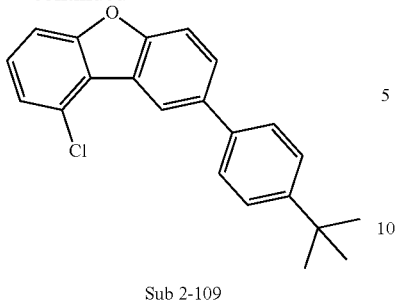

Sub 2-109

(1) Synthesis of Sub 2-109

After dissolving 8-bromo-1-chlorodibenzo[b,d]thiophene (30.0 g, 100.81 mmol) in 336 mL of THF in a round bottom flask, (4-(tert-butyl)phenyl)boronic acid (17.95 g, 100.81 mmol), Pd(PPh$_3$)$_4$ (3.02 g, 3.49 mmol), NaOH (8.06 g, 201.62 mmol), and 84 mL of water were added and stirred at 80° C. When the reaction was completed, extracted with CH$_2$Cl$_2$ and water, the organic layer was dried over MgSO$_4$ and concentrated, and the resulting compound was recrystallized using a silica gel column to obtain 26.7 g of product (yield: 75%).

Examples of Sub 2 are as follows, but are not limited thereto.

Sub 2-13

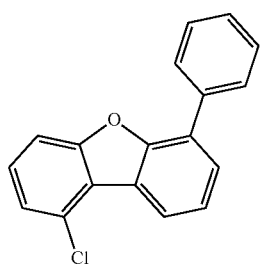

Sub 2-14

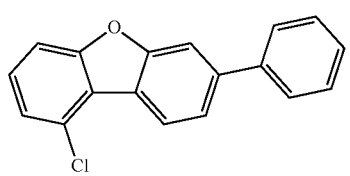

Sub 2-15

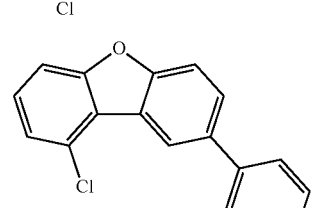

Sub 2-16

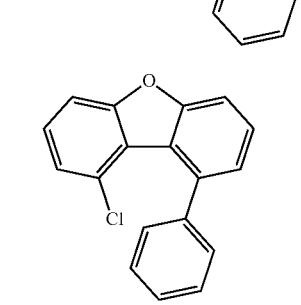

Sub 2-29

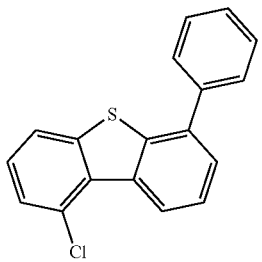

Sub 2-30

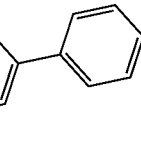

Sub 2-31

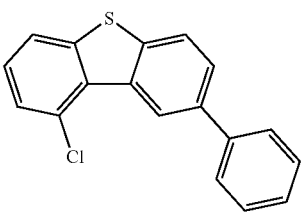

Sub 2-32

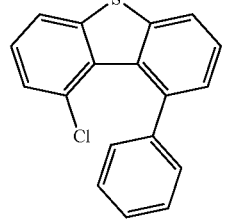

Sub 2-36

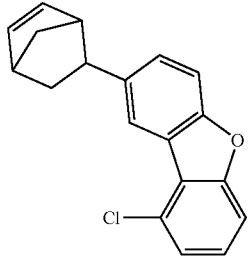

Sub 2-39

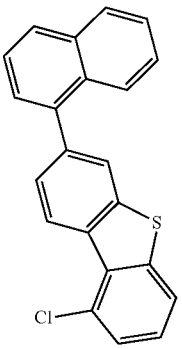

Sub 2-41
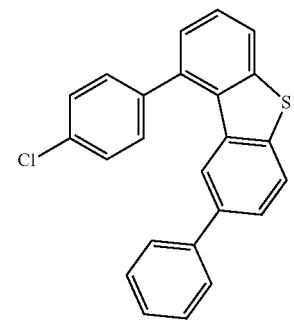
Sub 2-44
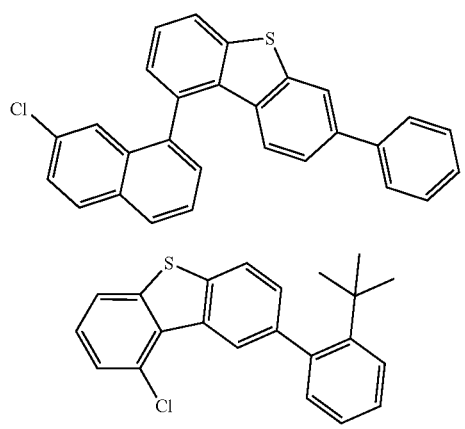
Sub 2-45
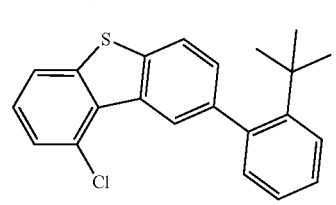
Sub 2-52
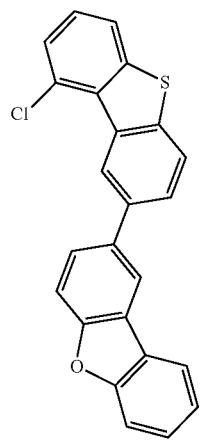
Sub 2-54
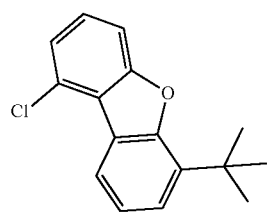
Sub 2-57
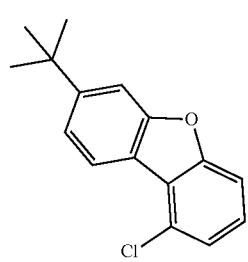
Sub 2-59
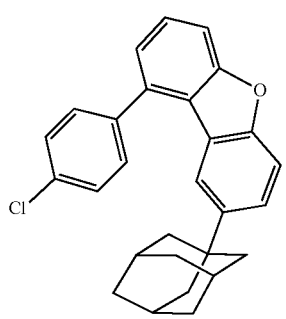
Sub 2-60
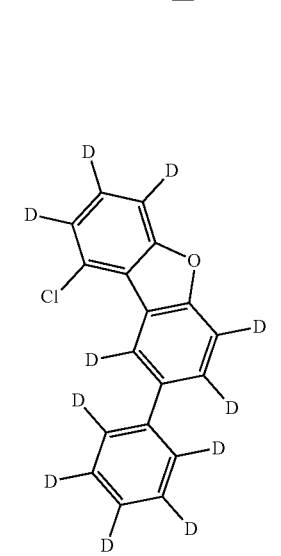
Sub 2-68
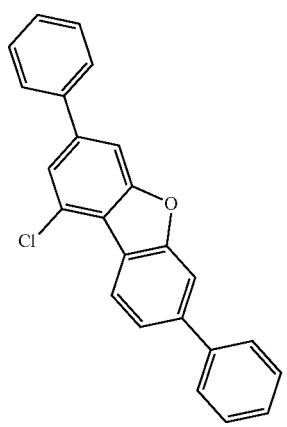
Sub 2-69
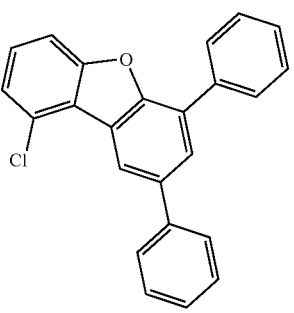

Sub 2-72
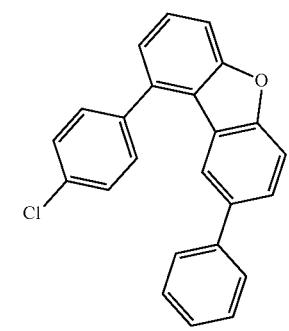
Sub 2-73
Sub 2-75
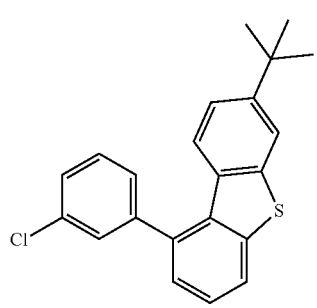
Sub 2-81
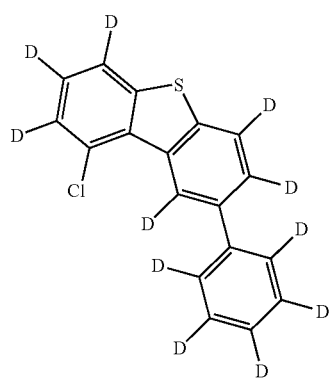
Sub 2-103
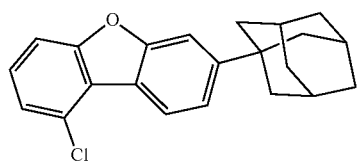
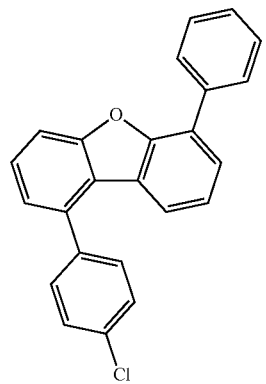
Sub 2-104
Sub 2-105
Sub 2-106
Sub 2-107
Sub 2-108
Sub 2-109

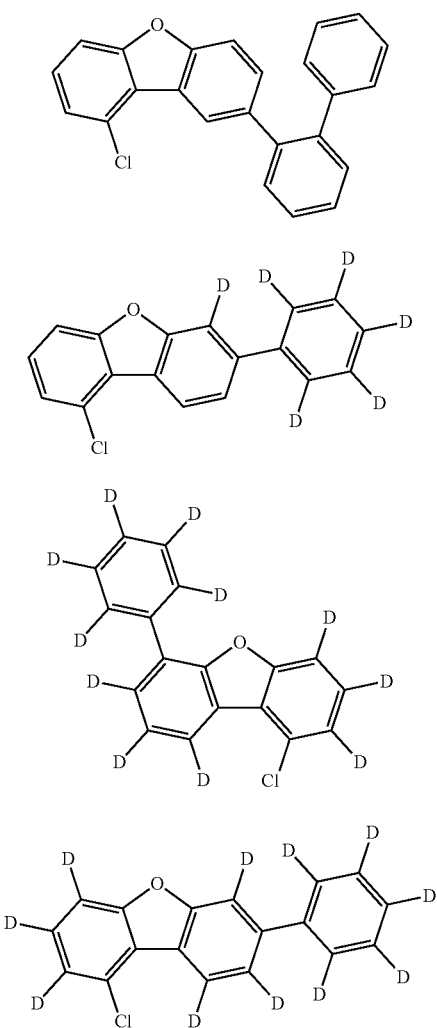
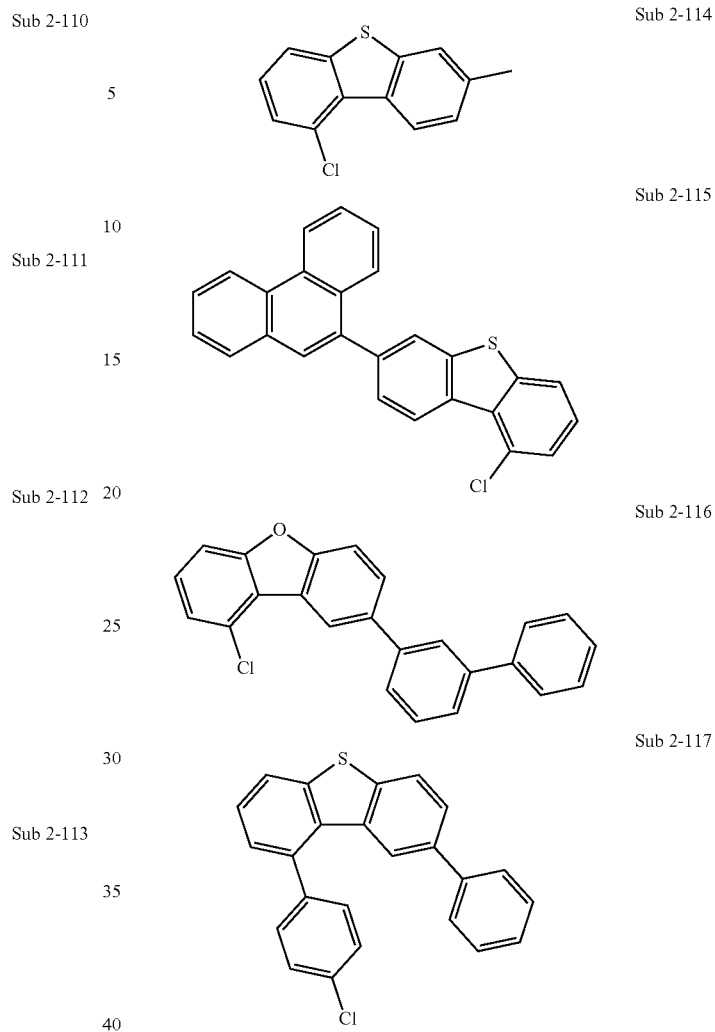

| compound | FD-MS | compound | FD-MS |
|---|---|---|---|
| Sub 2-13 | m/z = 278.05<br>.(C$_{18}$H$_{11}$ClO = 27874) | Sub 2-14 | m/z = 278.05<br>(C$_{18}$H$_{11}$ClO = 278.74) |
| Sub 2-15 | m/z = 278.05<br>(C$_{18}$H$_{11}$ClO-278.74) | Sub 2-16 | m/z = 278.05<br>(C$_{18}$H$_{11}$ClO = 278.74) |
| Sub 2-29 | m/z = 294.03<br>(C$_{18}$H$_{11}$ClS = 294.80) | Sub 2-30 | m/z = 294.03<br>(C$_{18}$H$_{11}$ClS = 294.80) |
| Sub 2-31 | m/z = 294.03<br>8(C$_{18}$H$_{11}$ClS = 294.0) | Sub 2-32 | m/z = 294.03<br>(C$_{18}$H$_{11}$ClS = 294.80) |
| Sub 2-36 | m/z = 294.08<br>(C$_{19}$H$_{15}$ClO = 294.78) | Sub 2-39 | m/z = 344.04<br>(C$_{22}$H$_{13}$ClS = 344.86) |
| Sub 2-41 | m/z = 370.06<br>(C$_{24}$H$_{15}$ClS = 370.89) | Sub 2-44 | m/z = 420.07<br>(C$_{28}$H$_{17}$ClS = 420.95) |
| Sub 2-45 | m/z = 350.09<br>(C$_{22}$H$_{19}$ClS-350.90) | Sub 2-52 | m/z = 384.04<br>(C$_{24}$H$_{13}$ClOS = 384.88) |
| Sub 2-54 | m/z = 258.08<br>(C$_{16}$H$_{15}$ClO = 258.75) | Sub 2-57 | m/z = 258.08<br>(C$_{16}$H$_{15}$ClO = 258.75) |
| Sub 2-59 | m/z = 412.16<br>(C$_{28}$H$_{25}$ClO = 412.96) | Sub 2-60 | m/z = 289.12<br>(C$_{18}$D$_{11}$ClO = 289.80) |
| Sub 2-68 | m/z = 354.08<br>(C$_{24}$H$_{15}$ClO = 354.83) | Sub 2-69 | m/z = 354.08<br>(C$_{24}$H$_{15}$ClO = 354.83) |
| Sub 2-72 | m/z = 354.08<br>(C$_{24}$H$_{15}$ClO = 354.83) | Sub 2-73 | m/z = 350.09<br>(C$_{22}$H$_{19}$ClS = 350.9) |
| Sub 2-75 | m/z = 305.10<br>(C$_{18}$D$_{11}$ClS = 305.86) | Sub 2-81 | m/z = 336.13<br>(C$_{22}$H$_{21}$ClO = 336.86) |

TABLE 2-continued

| compound | FD-MS | compound | FD-MS |
| --- | --- | --- | --- |
| Sub 2-103 | m/z = 354.08 ($C_{24}H_{15}ClO$ = 354.83) | Sub 2-104 | m/z = 354.08 ($C_{24}H_{15}ClO$ = 354.83) |
| Sub 2-105 | m/z = 328.07 ($C_{22}H_{13}ClO$ = 328.79) | Sub 2-106 | m/z = 260.04 ($C_{15}H_{13}ClS$ = 260.78) |
| Sub 2-107 | m/z = 370.06 ($C_{24}H_{15}ClS$ = 370.89) | Sub 2-108 | m/z = 370.06 ($C_{24}H_{15}ClS$ = 370.89) |
| Sub 2-109 | m/z = 350.09 ($C_{22}H_{19}ClS$ = 350.90) | Sub 2-110 | m/z = 354.08 ($C_{24}H_{15}ClO$ = 354.83) |
| Sub 2-111 | m/z = 283.08 ($C_{18}H_6D_5ClO$ = 283.77) | Sub 2-112 | m/z = 289.12 ($C_{18}D_{11}ClO$ = 289.80) |
| Sub 2-113 | m/z = 289.12 ($C_{18}D_{11}ClO$ = 289.80) | Sub 2-114 | m/z = 232.01 ($C_{13}H_9ClS$ = 232.73) |
| Sub 2-115 | m/z = 394.06 ($C_{26}H_{15}ClS$ = 394.92) | Sub 2-116 | m/z = 354.08 ($C_{24}H_{15}ClO$ = 354.83) |
| Sub 2-117 | m/z = 370.06 ($C_{24}H_{15}ClS$ = 370.89) | | |

Synthesis Example of Final Product

Synthesis Example of P2-5

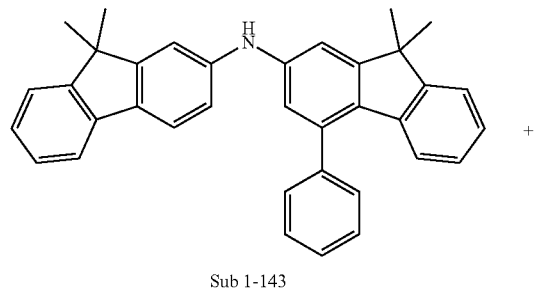

(1) Synthesis of P2-5

Sub 1-143 (25.0 g, 52.34 mmol) was placed in a round bottom flask and dissolved in 174 mL of Toluene, then Sub 2-15 (14.59 g, 52.34 mmol), $Pd_2(dba)_3$ (1.44 g, 1.57 mmol), $P(t-Bu)_3$ (0.64 g, 3.14 mmol), NaOt-Bu (10.06 g, 104.68 mmol) were added and stirred at 110° C. When the reaction was completed, extracted with Toluene and water, the organic layer was dried over $MgSO_4$ and concentrated, and the resulting compound was recrystallized using a silica gel column to obtain 29 g of product (yield: 76%).

Synthesis Example of P2-18

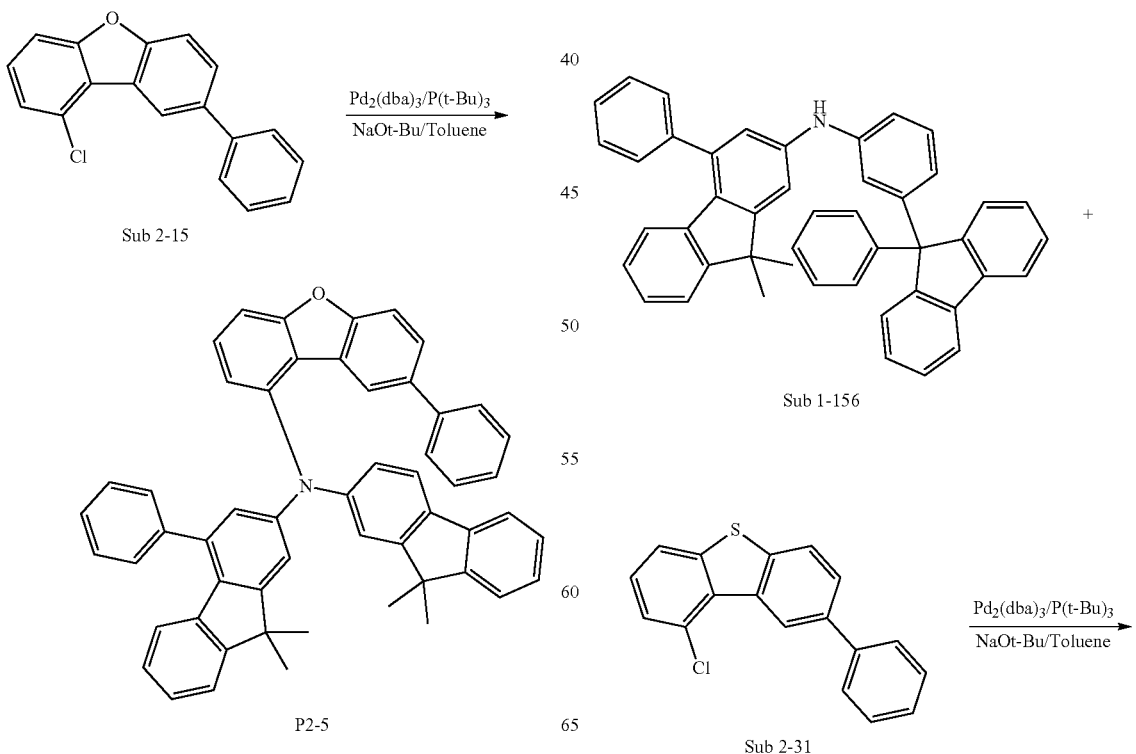

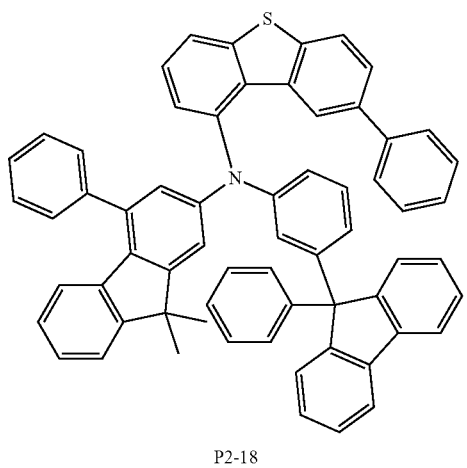

P2-18

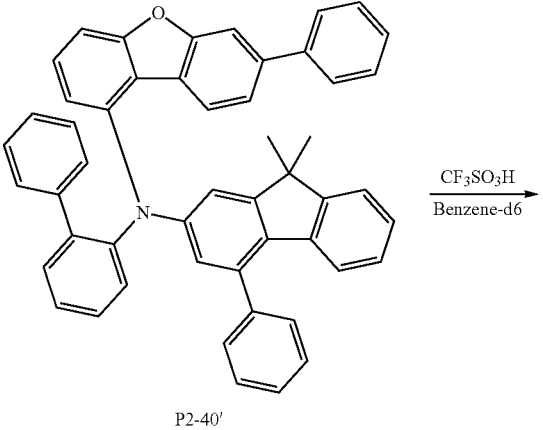

P2-40'

(1) Synthesis of P2-18

Sub 1-156 (27.0 g, 44.87 mmol) was placed in a round bottom flask and dissolved in 150 mL of Toluene, then Sub 2-31 (13.23 g, 44.87 mmol), $Pd_2(dba)_3$ (1.23 g, 1.35 mmol), $P(t-Bu)_3$ (0.54 g, 2.69 mmol), NaOt-Bu (8.62 g, 89.73 mmol) were added and stirred at 110° C. When the reaction was completed, extracted with Toluene and water, the organic layer was dried over $MgSO_4$ and concentrated, and the resulting compound was recrystallized using a silica gel column to obtain 32.8 g of product (yield: 84%).

Synthesis Example of P2-40

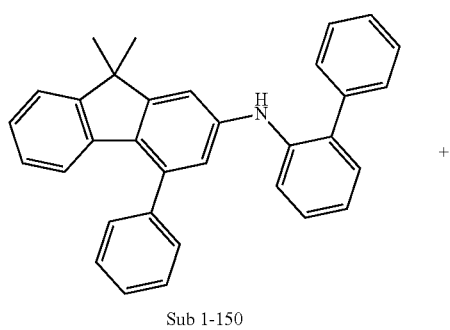

Sub 1-150

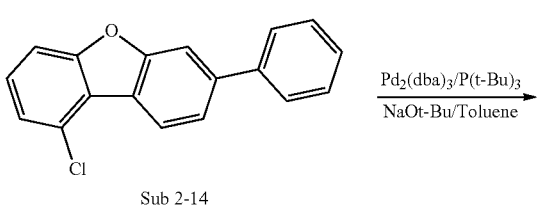

Sub 2-14

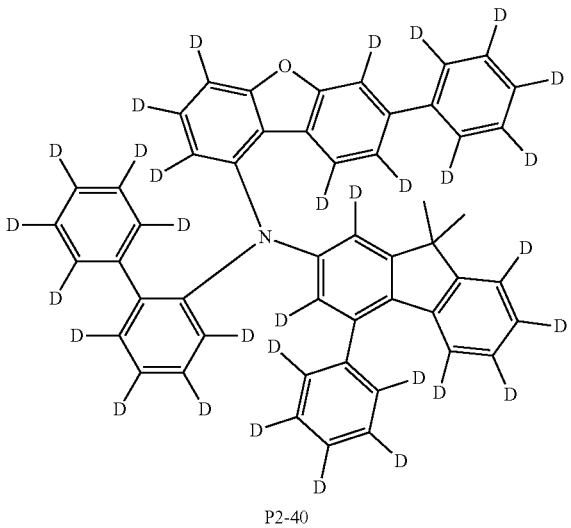

P2-40

(1) Synthesis of P2-40'

Sub 1-150 (30.0 g, 68.56 mmol) was placed in a round bottom flask and dissolved in 229 mL of Toluene, then Sub 2-85 (68.56 g, 68.56 mmol), $Pd_2(dba)_3$ (1.88 g, 2.06 mmol), $P(t-Bu)_3$ (0.83 g, 4.11 mmol), NaOt-Bu (13.18 g, 137.11 mmol) were added and stirred at 110° C. When the reaction was completed, extracted with Toluene and water, the organic layer was dried over $MgSO_4$ and concentrated, and the resulting compound was recrystallized using a silica gel column to obtain 34.5 g of product (yield: 74%).

(2) Synthesis of P2-40

The obtained P2-40' (32.80 g, 48.25 mmol) was dissolved in Benzene-$D_6$ (1054 mL) in a round-bottom flask, then $CF_3SO_3H$ (8.58 mL, 96.49 mmol) was slowly added and stirred at room temperature for 16 hours. When the reaction is complete, neutralize by adding $Na_2CO_3$ (15.34 g, 144.74 mmol) dissolved in $D_2O$. After extraction with toluene and $D_2O$, the organic layer was dried over $MgSO_4$ and concentrated, and the resulting compound was purified by silica gel column and recrystallized to obtain 26.5 g of the product (yield: 77%).

Synthesis Example of P2-49

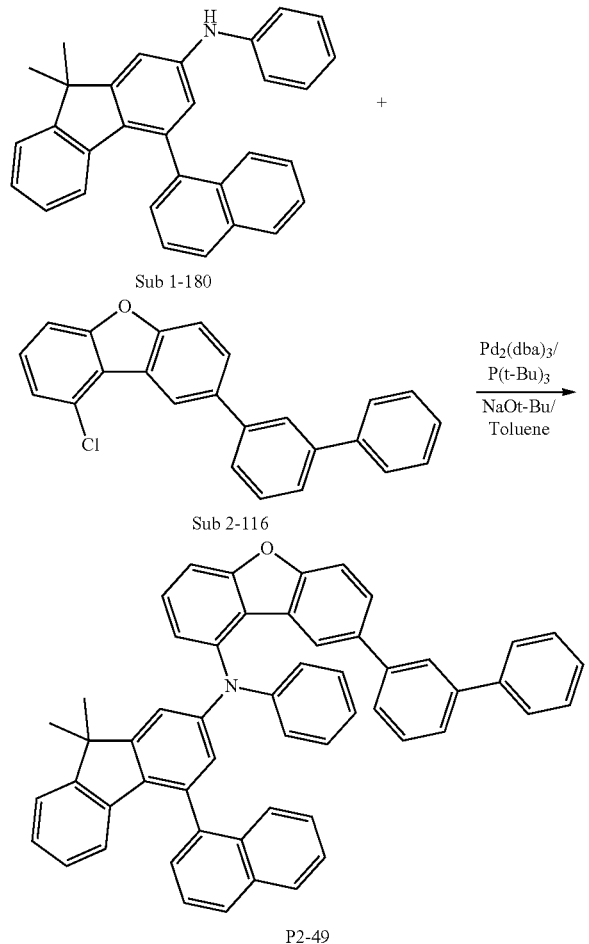

(1) Synthesis of P2-49

Sub 1-180 (32.5 g, 78.97 mmol) was placed in a round bottom flask and dissolved with toluene (263 mL), and Sub 2-116 (28.02 g, 78.97 mmol), Pd$_2$(dba)$_3$ (2.17 g, 2.37 mmol), P(t-Bu)$_3$ (0.96 g, 4.74 mmol), NaOt-Bu (15.18 g, 157.94 mmol) were added and 48.2 g of the product (yield: 83%) was obtained using the synthetic method of P1-2.

Meanwhile, the FD-MS values of compounds P2-1 to P2-56 of the present invention are as shown in Table 3.

TABLE 3

| compound | FD-MS | compound | FD-MS |
|---|---|---|---|
| P2-1 | m/z = 693.27 ($C_{51}H_{35}$ = 693.85) | P2-2 | m/z = 709.24 ($C_{51}H_{35}NOS$ = 709.91) |
| P2-3 | m/z = 709.24 ($C_{51}H_{35}NOS$ = 709.91) | P2-4 | m/z = 709.24 ($C_{51}H_{35}NOS$ = 709.91) |
| P2-5 | m/z = 719.32 ($C_{54}H_{41}NO$ = 719.93) | P2-6 | m/z = 719.32 ($C_{54}H_{41}NO$ = 719.93) |
| P2-7 | m/z = 795.35 ($C_{60}H_{45}NO$ = 796.03) | P2-8 | m/z = 785.28 ($C_{57}H_{35}NOS$ = 786.00) |
| P2-9 | m/z = 603.26 ($C_{45}H_{33}NO_2$ = 603.76) | P2-10 | m/z = 679.29 ($C_{51}H_{37}NO$ = 679.86) |
| P2-11 | m/z = 679.29 ($C_{51}H_{37}NO$ = 679.86) | P2-12 | m/z = 679.29 ($C_{51}H_{37}NO$ = 679.86) |
| P2-13 | m/z = 755.32 ($C_{57}H_{41}NO$ = 755.96) | P2-14 | m/z = 755.32 ($C_{57}H_{41}NO$ = 755.96) |
| P2-15 | m/z = 623.32 ($C_{46}H_{41}NO$ = 623.84) | P2-16 | m/z = 709.33 ($C_{53}H_{43}NO$ = 709.93) |
| P2-17 | m/z = 715.38 ($C_{53}D_{49}NO$ = 715.98) | P2-18 | m/z = 859.33 ($C_{64}H_{45}NS$ = 860.13) |
| P2-19 | m/z = 825.34 ($C_{61}H_{47}NS$ = 826.11) | P2-20 | m/z = 935.36 ($C_{70}H_{49}NS$ = 936.23) |
| P2-21 | m/z = 555.26 ($C_{41}H_{33}NO$ = 555.72) | P2-22 | m/z = 751.33 ($C_{55}H_{45}NS$ = 752.03) |
| P2-23 | m/z = 709.24 ($C_{51}H_{35}NOS$ = 709.91) | P2-24 | m/z = 647.23 ($C_{46}H_{33}NOS$ = 647.84) |
| P2-25 | m/z = 689.31 ($C_{50}H_{43}NS$ = 689.96) | P2-26 | m/z = 651.30 ($C_{47}H_{41}NS$ = 651.91) |
| P2-27 | m/z = 679.29 ($C_{51}H_{37}NO$ = 679.86) | P2-28 | m/z = 679.29 ($C_{51}H_{37}NO$ = 679.86) |
| P2-29 | m/z = 759.26 ($C_{55}H_{37}NOS$ = 759.97) | P2-30 | m/z = 819.35 ($C_{62}H_{45}NO$ = 820.05) |
| P2-31 | m/z = 693.27 ($C_{51}H_{35}NO_2$ = 693.85) | P2-32 | m/z = 709.24 ($C_{51}H_{35}NOS$ = 709.91) |
| P2-33 | m/z = 698.30 ($C_{51}H_{30}D_5NO_2$ = 698.88) | P2-34 | m/z = 698.30 ($C_{51}H_{30}D_5NO_2$ = 698.88) |
| P2-35 | m/z = 720.31 ($C_{51}H_{24}D_{11}NOS$ = 720.97) | P2-36 | m/z = 720.31 ($C_{51}H_{24}D_{11}NOS$ = 720.97) |
| P2-37 | m/z = 608.29 ($C_{45}H_{28}D_5NO$ = 608.80) | P2-38 | m/z = 688.34 ($C_{51}H_{28}D_9NO$ = 688.92) |
| P2-39 | m/z = 710.48 ($C_{51}H_6D_{31}NO$ = 711.05) | P2-40 | m/z = 710.48 ($C_{51}H_6D_{31}NO$ = 711.05) |
| P2-41 | m/z = 755.32 ($C_{57}H_{41}NO$ = 755.96) | P2-42 | m/z = 753.30 ($C_{57}H_{39}NO$ = 753.94) |
| P2-43 | m/z = 715.33 ($C_{52}H_{45}NS$ = 716.00) | P2-44 | m/z = 569.27 ($C_{42}H_{35}NO$ = 569.75) |
| P2-45 | m/z = 707.32 ($C_{53}H_{41}NO$ = 707.92) | P2-46 | m/z = 703.29 ($C_{53}H_{37}NO$ = 703.88) |
| P2-47 | m/z = 719.26 ($C_{53}H_{37}NS$ = 719.95) | P2-48 | m/z = 871.38 ($C_{66}H_{49}NO$ = 872.12) |
| P2-49 | m/z = 729.30 ($C_{55}H_{39}NO$ = 729.92) | P2-50 | m/z = 595.29 ($C_{44}H_{37}NO$ = 595.79) |
| P2-51 | m/z = 663.21 ($C_{46}H_{33}NS_2$ = 663.90) | P2-52 | m/z = 771.30 ($C_{57}H_{41}NS$ = 772.02) |
| P2-53 | m/z = 693.27 ($C_{51}H_{35}NO_2$ = 693.85) | P2-54 | m/z = 693.27 ($C_{51}H_{35}NO_2$ = 693.85) |
| P2-55 | m/z = 693.27 ($C_{51}H_{35}NO_2$ = 693.85) | P2-56 | m/z = 709.24 ($C_{51}H_{35}NOS$ = 709.91) |

[Example 1] Green Organic Light Emitting Device (Emitting-Auxiliary Layer)

Compound A and Compound B were used on the ITO layer (anode) formed on the glass substrate, and a hole injection layer with a thickness of 10 nm was formed by doping Compound B at a weight ratio of 98:2, and Compound A was vacuum deposited to a thickness of 110 nm on the hole injection layer to form a hole transport layer.

Next, compound P2-1 of the present invention was vacuum deposited to a thickness of 10 nm on the hole transport layer to form an emitting-auxiliary layer. Afterwards, compound D-G was used as the host material of the emitting layer and tris(2-phenylpyridine)-iridium (hereinafter, 'Ir(ppy)$_3$') was used as the dopant material, and the dopants were doped in a 90:10 weight ratio to form an emitting layer with a thickness of 30 nm.

Next, Compound E is vacuum deposited on the emitting layer to form a hole blocking layer with a thickness of 10 nm, and an electron transport layer with a thickness of 30 nm was formed on the hole blocking layer using a mixture of Compound F and Compound G at a weight ratio of 5:5. Afterwards, Compound G was deposited on the electron transport layer to form an electron injection layer with a thickness of 0.2 nm, and then Al was deposited to form a cathode with a thickness of 150 nm.

compound A: N-([1,1'-biphenyl]-4-yl)-9,9-dimethyl-N-(4-(9-phenyl-9H-carbazol-3-yl)phenyl)-9H-fluoren-2-amine compound B: 4,4',4''-((1E,1'E,1''E)-cyclopropane-1,2,3-triylidenetris(cyanomethaneylylidene))tris(2,3,5,6-tetrafluorobenzonitrile)

compound D-G: 5-(3-(4,6-diphenyl-1,3,5-triazin-2-yl)phenyl)-7,7-dimethyl-5,7-dihydroindeno[2,1-b]carbazole compound E: 2-(4'-(9,9-dimethyl-9H-fluoren-2-yl)-[1,1'-biphenyl]-3-yl)-4,6-diphenyl-1,3,5-triazine compound F: 2,7-bis(4-(4,6-diphenyl-1,3,5-triazin-2-yl)phenyl)naphthalene compound G: (8-quinolinolato)lithium

[Example 2] to [Example 10]

An organic light emitting device was manufactured in the same manner as in Example 1, except that the compound of the present invention shown in Table 4 was used as the emitting-auxiliary layer material instead of the compound P2-1 of the present invention.

[Comparative Example 1] or [Comparative Example 2]

An organic electroluminescent device was manufactured in the same manner as in Example 1, except that Comparative Compound A or Comparative Compound B were used instead of Compound P2-1 of the present invention as the emitting-auxiliary layer material.

[Comparative Compound A]

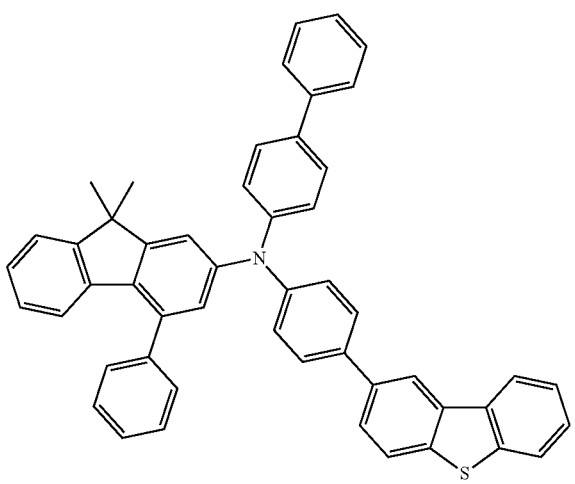

[Comparative Compound B]

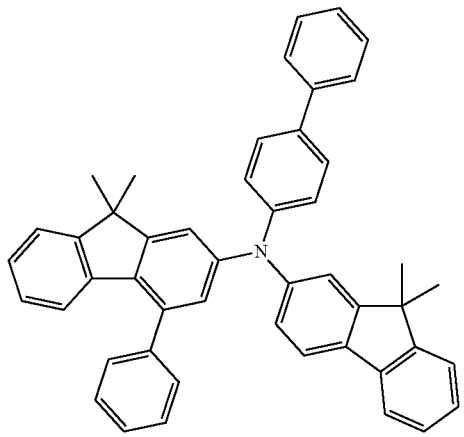

A forward bias direct current voltage was applied to the organic electroluminescent devices of Examples and Comparative Examples manufactured in this way, and the electroluminescence (EL) characteristics were measured using PR-650 from Photoresearch. As a result of the measurement, T95 life was measured at a standard luminance of 5000 cd/m² through life measuring apparatus manufactured by McScience. Table 4 shows the results of device fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 4

| | compound | Voltage | Current Density (mA/cm²) | Efficiency (cd/A) | T(95) |
|---|---|---|---|---|---|
| comparative example1 | comparative compound A | 5.3 | 18.7 | 26.8 | 91.1 |
| comparative example2 | comparative compound B | 5.1 | 19.3 | 25.9 | 86.9 |
| example1 | compound(P2-1) | 4.6 | 11.5 | 43.3 | 135.6 |
| example2 | compound(P2-5) | 4.7 | 11.8 | 42.4 | 134.0 |
| example3 | compound(P2-10) | 4.7 | 11.2 | 44.6 | 140.2 |
| example4 | compound(P2-18) | 4.8 | 11.9 | 42.0 | 132.1 |
| example5 | compound(P2-22) | 4.9 | 14.2 | 35.3 | 111.0 |
| example6 | compound(P2-23) | 4.9 | 12.6 | 39.7 | 124.9 |
| example7 | compound(P2-25) | 4.9 | 12.2 | 41.1 | 129.5 |
| example8 | compound(P2-33) | 4.6 | 11.5 | 43.4 | 141.9 |
| example9 | compound(P2-38) | 4.7 | 11.2 | 44.7 | 146.5 |
| example10 | compound(P2-53) | 4.8 | 11.4 | 43.8 | 147.6 |

As can be seen from the results in Table 4, when a green organic electroluminescent device is manufactured using the material for an organic electroluminescent device of the present invention as a material for the emitting auxiliary layer, the compound of the present invention exhibits remarkable characteristics in device performance compared to when comparative compound A or comparative compound B is used.

As can be seen from the above, when comparing the comparative compound A and the compound of the present invention, Comparative Compound A differs in that the amino group is bonded to the 2nd position of dibenzothiophene, whereas the compound of the present invention has the amino group bonded to the 1st position of dibenzofuran or dibenzothiophene. Also, when comparing the comparative compound B and the compound of the present invention, Comparative compound B differs in that it has 2 substituted fluorenes, whereas the compound of the present invention has dibenzofuran or dibenzothiophene bonded instead of one fluorene. These differences can be confirmed through Table 5.

Table 5 shows data measured for Comparative Compound A or Comparative Compound B and Compound P2-10 of the present invention using the DFT Method (B3LYP/6-31g(D)) of the Gaussian program.

TABLE 5

|  | comparative compound A | comparative compound B | P2-10 |
|---|---|---|---|
| HOMO (eV) | −4.819 | −4.734 | −4.938 |

If Table 5 is described in detail, compared to comparative compound A or comparative compound B, compound P2-10 of the present invention has a deeper HOMO value. That is, the deep HOMO results in excellent hole injection characteristics moving into the host, which in turn results in increased efficiency. As can be seen from the above results, it can be confirmed that the characteristics are very different depending on the type and substituent position even within the same skeleton.

[Example 11] Red Organic Light Emitting Device (Emitting-Auxiliary Layer)

Compound A and Compound B were used on the ITO layer (anode) formed on the glass substrate, and a hole injection layer with a thickness of 10 nm was formed by doping Compound B at a weight ratio of 98:2, and Compound A was vacuum deposited to a thickness of 110 nm on the hole injection layer to form a hole transport layer.

Next, compound P2-1 of the present invention was vacuum deposited to a thickness of 10 nm on the hole transport layer to form an emitting-auxiliary layer. Afterwards, compound D-R was used as the host material of the emitting layer, and bis-(1-phenylisoquinolyl)iridium(III) acetylacetonate (hereinafter '(piq)$_2$Ir(acac)') was used as the dopant material, and the dopant was doped so that the weight ratio of the host and dopant was 95:5 to form an emitting layer with a thickness of 30 nm.

Next, Compound E is vacuum deposited on the emitting layer to form a hole blocking layer with a thickness of 10 nm, and an electron transport layer with a thickness of 30 nm was formed on the hole blocking layer using a mixture of Compound F and Compound G at a weight ratio of 5:5. Afterwards, Compound G was deposited on the electron transport layer to form an electron injection layer with a thickness of 0.2 nm, and then Al was deposited to form a cathode with a thickness of 150 nm.

compound D-R: 14-(4-phenylquinazolin-2-yl)-14H-benzo[c]benzo[4,5]thieno[2,3-a]carbazole

[Example 12] to [Example 21]

An organic light emitting device was manufactured in the same manner as in Example 1, except that the compound of the present invention shown in Table 6 was used as the emitting-auxiliary layer material instead of the compound P2-1 of the present invention.

[Comparative Example 3] to [Comparative Example 6]

An organic electroluminescent device was manufactured in the same manner as in Example 1, except that Comparative Compounds C to Comparative Compound F were used instead of Compound P2-1 of the present invention as the emitting-auxiliary layer material.

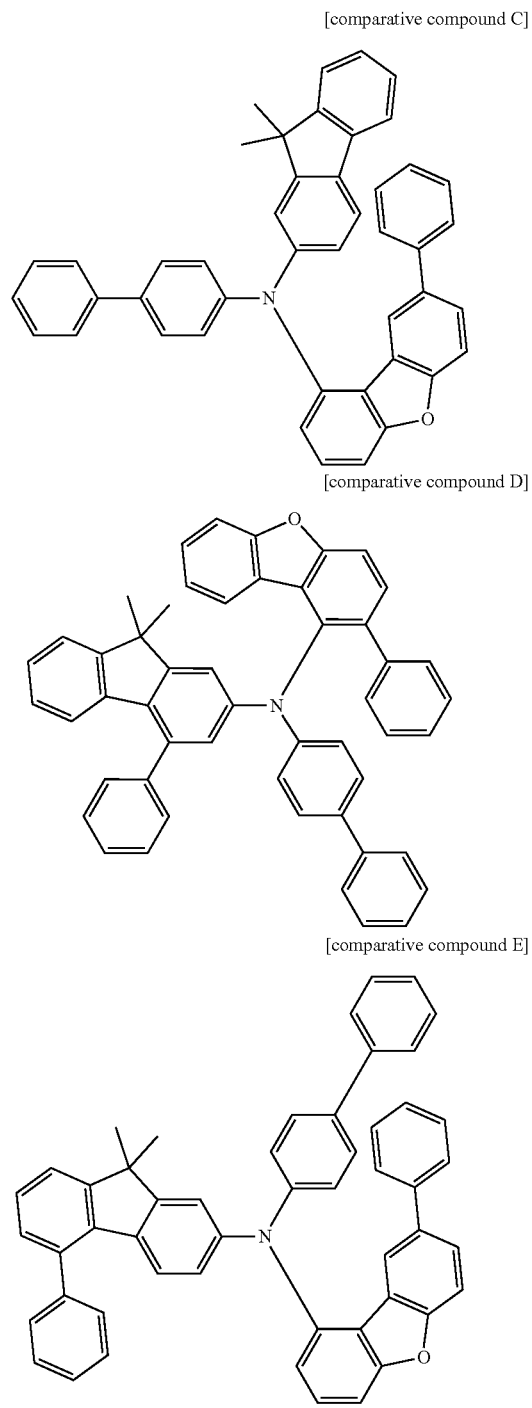

[comparative compound C]

[comparative compound D]

[comparative compound E]

-continued

[comparative compound F]

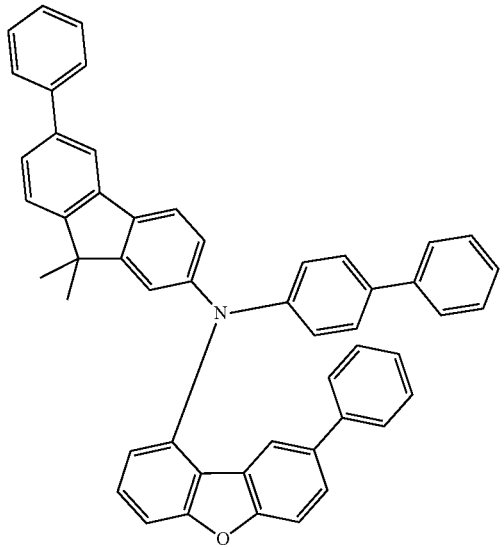

A forward bias direct current voltage was applied to the organic electroluminescent devices of Examples and Comparative Examples manufactured in this way, and the electroluminescence (EL) characteristics were measured using PR-650 from Photoresearch. As a result of the measurement, T95 life was measured at a standard luminance of 2500 cd/m$^2$ through life measuring apparatus manufactured by McScience. Table 6 shows the results of device fabrication and evaluation.

The measuring apparatus can evaluate the performance of new materials compared to comparative compounds under identical conditions, without being affected by possible daily fluctuations in deposition rate, vacuum quality or other parameters.

During the evaluation, one batch contains 4 identically prepared OLEDs including a comparative compound, and the performance of a total of 12 OLEDs is evaluated in 3 batches, so the value of the experimental results obtained in this way indicates statistical significance.

TABLE 6

| | compound | Voltage | Current Density (mA/cm$^2$) | Efficiency (cd/A) | T(95) |
|---|---|---|---|---|---|
| comparative example3 | comparative compound C | 5.0 | 9.2 | 27.1 | 95.0 |
| comparative example4 | comparative compound D | 4.9 | 8.7 | 28.6 | 92.4 |
| comparative example5 | comparative compound E | 5.0 | 9.1 | 27.5 | 96.3 |
| comparative example6 | comparative compound F | 4.8 | 8.6 | 29.0 | 89.9 |
| example11 | compound(P2-1) | 4.4 | 6.7 | 37.6 | 124.2 |
| example12 | compound(P2-5) | 4.5 | 6.8 | 36.8 | 122.8 |
| example13 | compound(P2-10) | 4.5 | 6.5 | 38.7 | 128.4 |
| example14 | compound(P2-25) | 4.7 | 7.0 | 35.6 | 118.6 |
| example15 | compound(P2-33) | 4.4 | 6.6 | 37.7 | 129.9 |
| example16 | compound(P2-34) | 4.7 | 7.1 | 35.1 | 128.9 |
| example17 | compound(P2-38) | 4.5 | 6.4 | 38.8 | 134.2 |
| example18 | compound(P2-53) | 4.6 | 6.6 | 38.0 | 135.2 |
| example19 | compound(P2-54) | 4.7 | 7.1 | 35.0 | 123.1 |
| example20 | compound(P2-55) | 4.7 | 7.4 | 33.7 | 109.5 |
| example21 | compound(P2-56) | 4.6 | 6.4 | 39.1 | 124.7 |

As can be seen in Table 6, when a red organic electroluminescent device is produced using the material for an organic electroluminescent device of the present invention as an emitting auxiliary layer material, the compound of the present invention exhibits remarkable characteristics in device performance compared to when comparative compounds C to F are used. In particular, it shows remarkable characteristics in lifespan.

As you can see from the above, when comparing the comparative compound C with the compound of the present invention, Comparative compound C has a structure in which no substituent is substituted on fluorene, whereas the compound of the present invention has a structure in which a substituent is further substituted on the 4th position of fluorene, which is a difference. In addition, when comparing comparative compound D with the compound of the present invention, Comparative compound D has a structure in which a substituent is further substituted at the 2nd position of dibenzofuran, whereas the compound of the present invention has a structure in which a substituent is further substituted at positions 6 to 9 of dibenzofuran, which is a difference. Additionally, when Comparative compound E and Comparative compound F are compared with the compound of the present invention, Comparative compound E or Comparative compound F has a structure in which a substituent is bonded to the 5th or 6th position of fluorene, whereas the compound of the present invention has a structure in which a substituent is further substituted at the 4th position of fluorene, which is a difference.

That is, there is a difference in that the presence or absence of a substituent on fluorene and the bonding position of the substituent are different. These differences can be confirmed through Table 7.

Table 7 shows the data for the weakest bond dissociation energies (hereinafter BDE) of comparative compounds C to F and compound P2-10 of the present invention, measured using molecular simulation (Gaussian09 Rev. C.01, Schrodinger Materials Science Suite 2024-2).

The BDE presented in Table 7 is the average value of BDE in the anion, cation, and neutral states of the molecule, and the higher the BDE value, the higher the structural stability of the molecule is considered to be.

TABLE 7

| | BDE (eV) |
|---|---|
| comparative compound C | 2.34 |
| comparative compound D | 2.32 |
| comparative compound E | 2.34 |
| comparative compound F | 2.26 |
| P2-10 | 2.35 |

As you can see in Table 7, it can be confirmed that the BDE value of compound P2-10 of the present invention is higher than that of comparative compounds C to F. In organic electronic devices, the lower the crystallinity of the thin film, the more likely it is that an amorphous state will be created, and the amorphous state can reduce grain boundaries and accelerate the mobility of charges and holes through isotropic and homogeneous characteristics. However, even if they are in the same amorphous state depending on the structure of the molecule, the quantum mechanical BDE of the solid-state molecule in the amorphous state can differ due to the intermolecular interaction when in the solid state, and the higher the value, the more stable the compound itself is.

Therefore, it is expected that when compound P2-10 of the present invention is used as an emitting-auxiliary layer of an organic electroluminescent device, the structural stability increases compared to when comparative compounds C to F are used, thereby maximizing the lifespan of the device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment.

The scope of the present invention shall be construed on the basis of the accompanying claims, and it shall be construed that all of the technical ideas included within the scope equivalent to the claims belong to the present invention.

What is claimed is:
1. A compound of Formula (1-10):

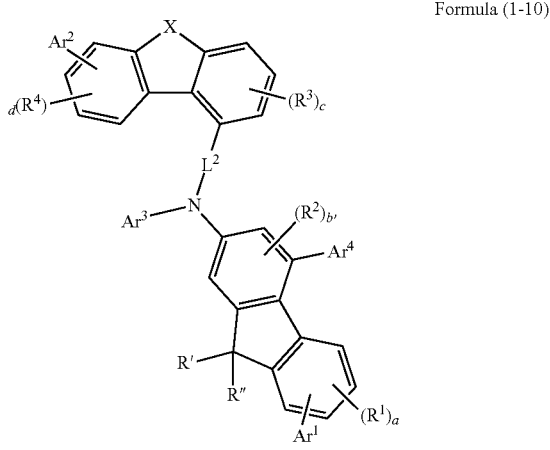

Formula (1-10)

wherein:
$R^1$, $R^2$, $R^3$ and $R^4$ are each independently the same or different, and each independently selected from the group consisting of hydrogen; deuterium; halogen; a $C_6$-$C_{60}$ aryl group; a fluorenyl group; a $C_2$-$C_{60}$ heterocyclic group including at least one heteroatom of O, N, S, Si and P; a fused ring group of a $C_3$-$C_{60}$ aliphatic ring and a $C_6$-$C_{60}$ aromatic ring; a $C_3$-$C_{60}$ aliphatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group;

a, c and d are each independently an integer of 0 to 3, b' is an integer of 0 to 2, R' and R" are each independently selected from the group consisting of a $C_6$-$C_{60}$ aryl group; a fluorenyl group; a $C_1$-$C_{50}$ alkyl group; and a $C_2$-$C_{20}$ alkenyl group, or R' and R" can be bonded to each other to form a ring, $Ar^1$ is selected from the group consisting of hydrogen; deuterium; a $C_6$-$C_{60}$ aryl group; a fluorenyl group; a $C_2$-$C_{60}$ heterocyclic group including at least one heteroatom of O, N, S, Si and P; a $C_3$-$C_{60}$ aliphatic ring; a fused ring group of a $C_3$-$C_{60}$ aliphatic ring and a $C_6$-$C_{60}$ aromatic ring; and a $C_1$-$C_{50}$ alkyl group;

$Ar^2$ is selected from the group consisting of a $C_6$-$C_{60}$ aryl group; a fluorenyl group; a $C_2$-$C_{60}$ heterocyclic group including at least one heteroatom of O, N, S, Si and P; a $C_3$-$C_{60}$ aliphatic ring; and a $C_1$-$C_{50}$ alkyl group;

$Ar^3$ is selected from the group consisting of a $C_6$-$C_{60}$ aryl group; a fluorenyl group; a $C_2$-$C_{60}$ heterocyclic group including at least one heteroatom of O, N, S, Si and P; a $C_3$-$C_{60}$ aliphatic ring; a $C_1$-$C_{50}$ alkyl group; and a $C_2$-$C_{20}$ alkenyl group;

$Ar^4$ is selected from the group consisting of a $C_6$-$C_{60}$ aryl group; a $C_2$-$C_{60}$ heterocyclic group including at least one heteroatom of O, N, S, Si and P; a $C_3$-$C_{60}$ aliphatic ring; and a $C_1$-$C_{50}$ alkyl group;

X is O or S, $L^2$ is a single bond or a $C_6$-$C_{60}$ arylene group;

wherein the aryl group, arylene group, heterocyclic group, fluorenyl group, fused ring group, aliphatic ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group, and the hydrogen of the substituents may be further substituted with one or more deuterium, and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

2. The compound of claim 1, wherein Formula (1-10) is represented by any of Formulas (1-11) to (1-13):

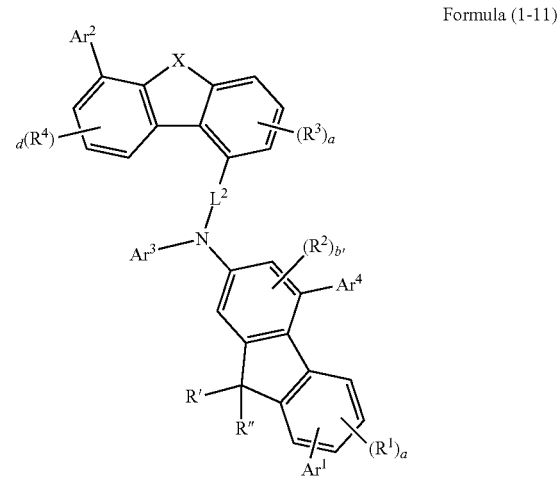

Formula (1-11)

Formula (1-12)

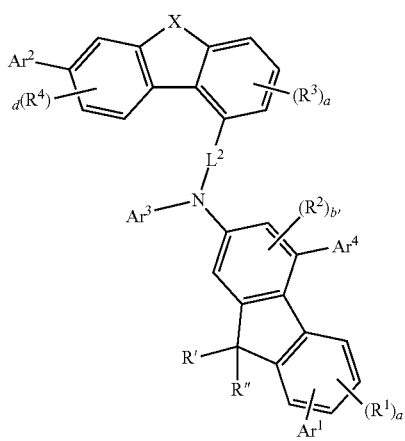

Formula (1-13)

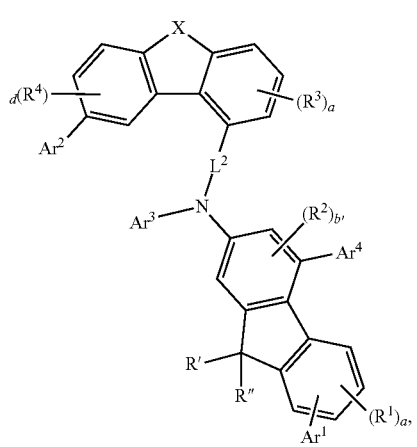

wherein X, R¹, R², R³, R⁴, R', R", Ar¹, Ar², Ar³, Ar⁴, L², a, b', c and d are the same as defined in claim 1.

3. The compound of claim 1, wherein at least one of Ar¹, Ar², Ar³ and Ar⁴ is represented by Formulae Ar-1 to Ar-6:

<Formula Ar-1>

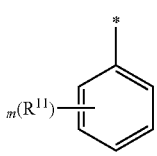

<Formula Ar-2>

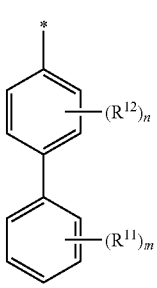

<Formula Ar-3>

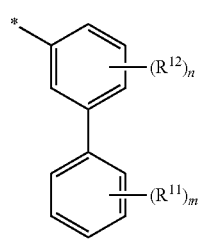

<Formula Ar-4>

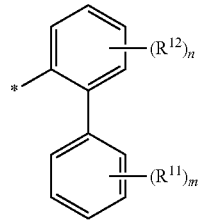

<Formula Ar-5>

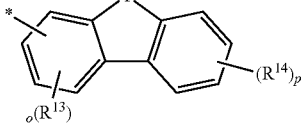

<Formula Ar-6>

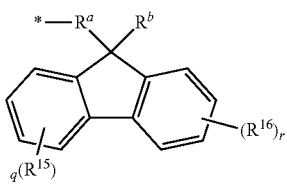

wherein:
1) $R^{11}$, $R^{12}$, $R^{13}$, $R^{14}$, $R^{15}$ and $R^{16}$ are selected from the group consisting of hydrogen; deuterium; halogen; a cyano group; a nitro group; a $C_1$-$C_{20}$ alkoxyl group; a $C_1$-$C_{20}$ alkyl group; a $C_2$-$C_{20}$ alkynyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group,
2) Y is O, S, $CR^xR^y$ or $NR^z$,
3) $R^a$, $R^b$, $R^x$, $R^y$ and $R^z$ are the same as the definition of $R^{11}$ above, or $R^a$ and $R^b$ or $R^x$ and $R^y$ can be bonded to each other to form a ring,
4) m is an integer of 0 to 5, n, p, q and r are an integer of 0 to 4, o is an integer of 0 to 3, and
5) * means a position to be bonded.

4. The compound of claim 1, wherein $L^2$ is represented by any of Formulas L-1 to L-3:

<Formula L-1>

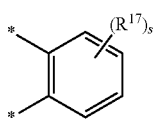

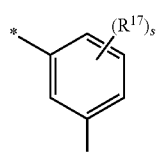
<Formula L-2>

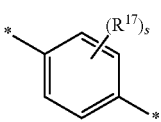
<Formula L-3> wherein:

1) $R^{17}$ is selected from the group consisting of hydrogen; deuterium; halogen; a cyano group; a nitro group; a $C_1$-$C_{20}$ alkoxyl group; a $C_1$-$C_{20}$ alkyl group; a $C_2$-$C_{20}$ alkeynyl group; a $C_2$-$C_{20}$ alkynyl group; a $C_6$-$C_{20}$ aryl group; a $C_6$-$C_{20}$ aryl group substituted with deuterium; a fluorenyl group; a $C_2$-$C_{20}$ heterocyclic group; a $C_3$-$C_{20}$ cycloalkyl group; a $C_7$-$C_{20}$ arylalkyl group; and a $C_8$-$C_{20}$ arylalkenyl group;

2) s is an integer of 0 to 4,

3) * means a position to be bonded.

5. The compound of claim 1, selected from the group consisting of the following compounds:

P2-1
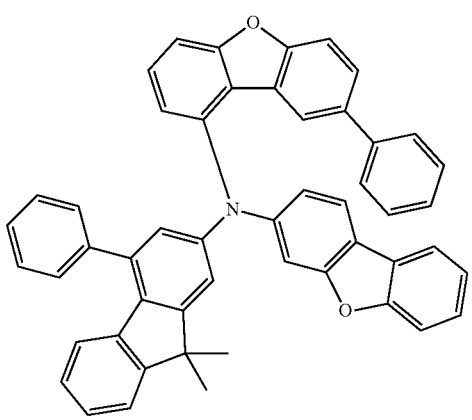

P2-2
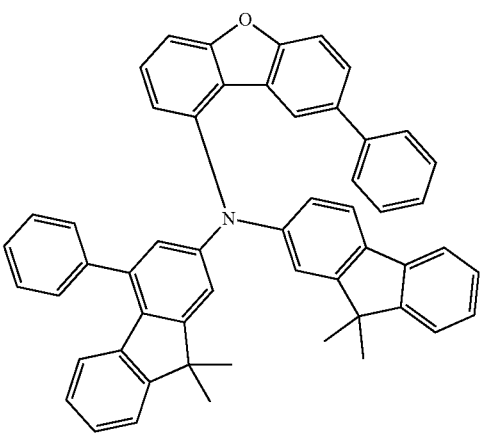

P2-3
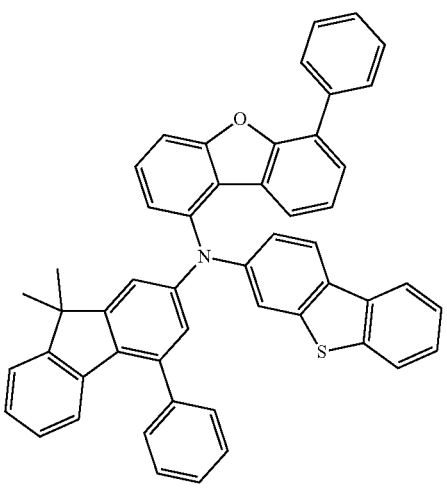

P2-4
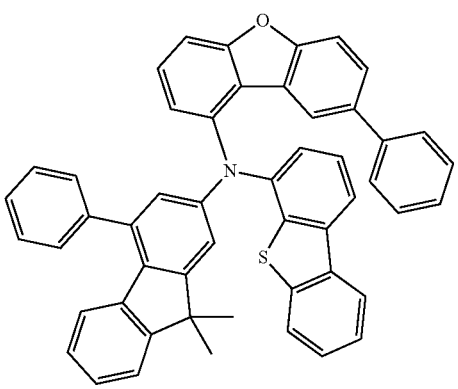

P2-5

P2-6
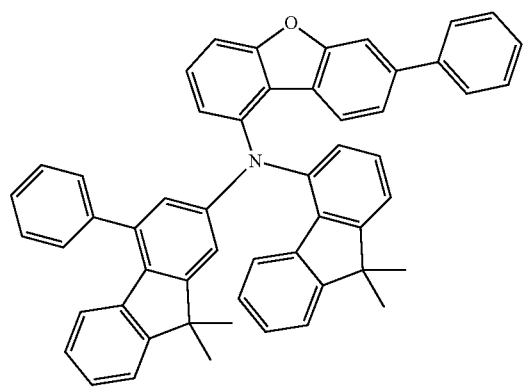
P2-7
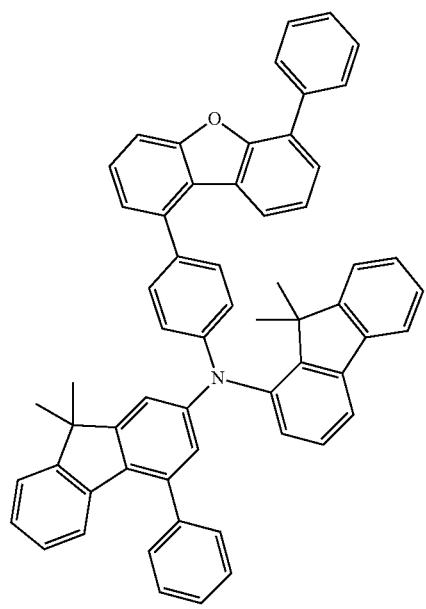
P2-8
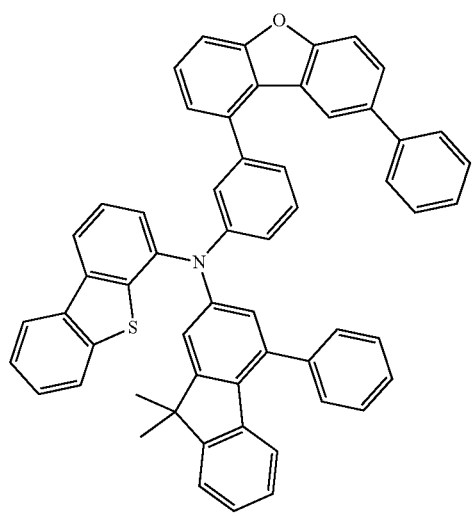
P2-9
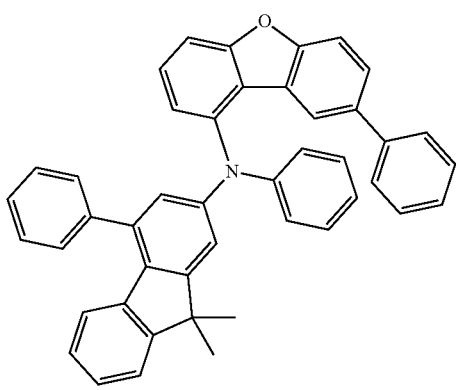
P2-10
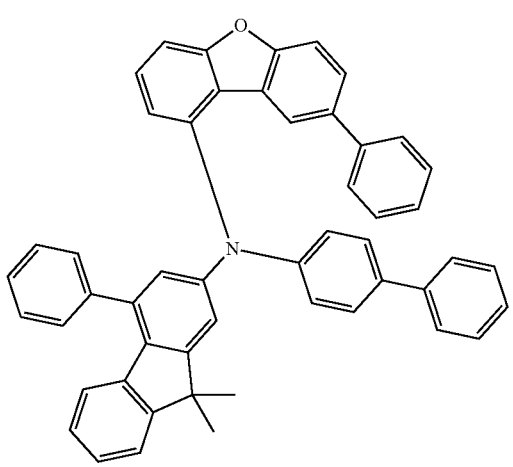
P2-11
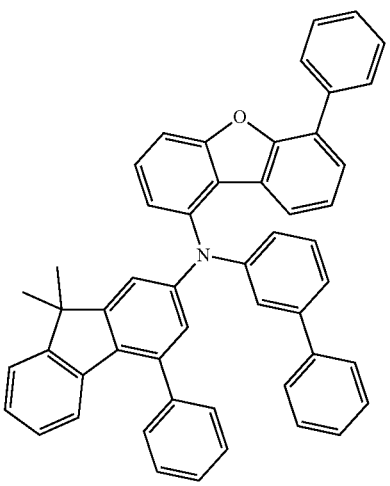

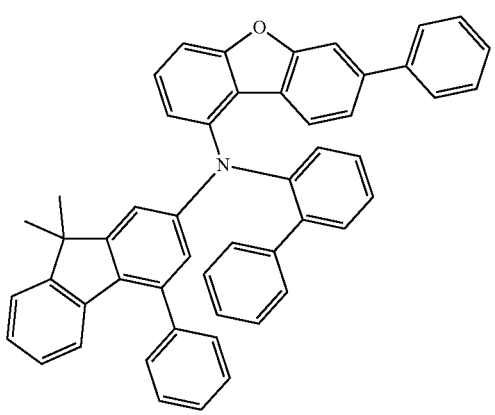
P2-12
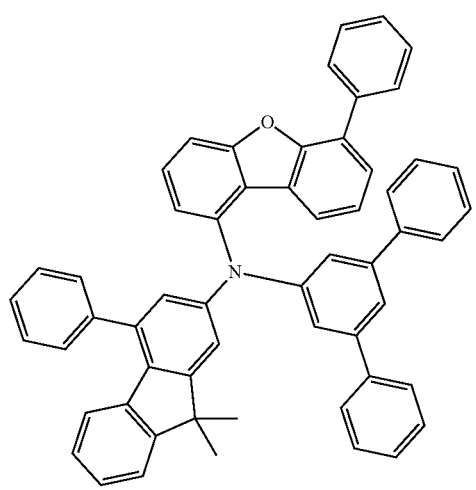
P2-13
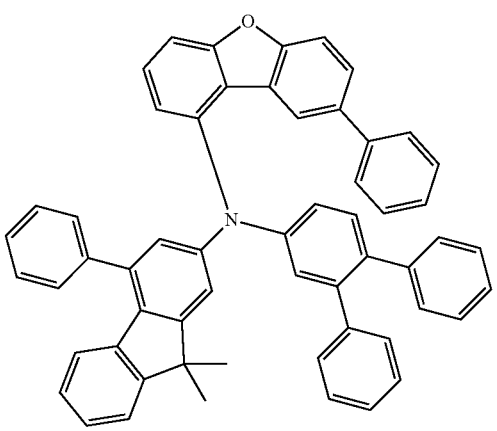
P2-14
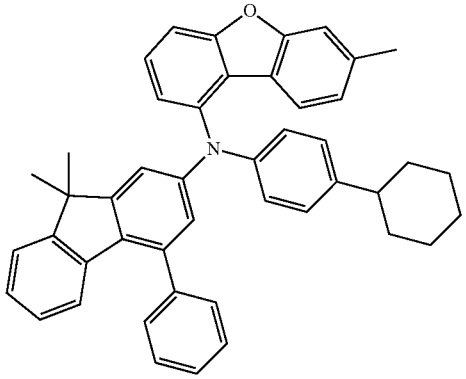
P2-15
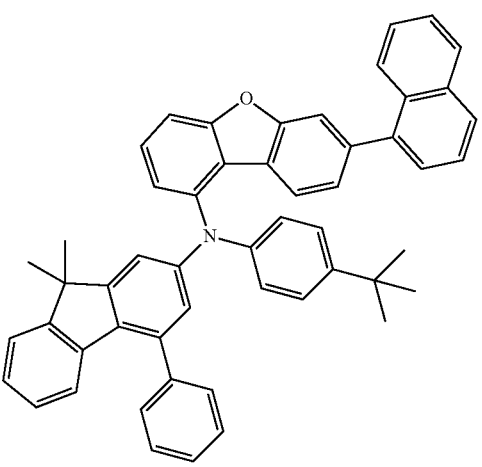
P2-16
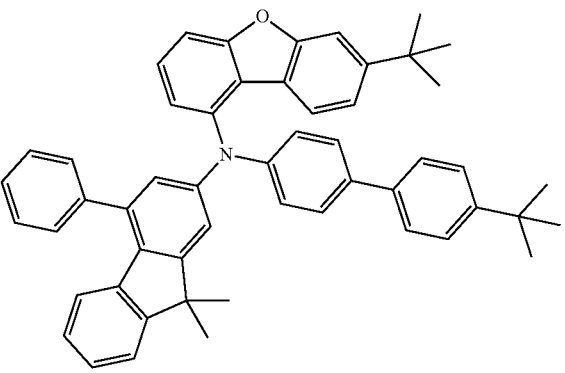
P2-17

P2-18
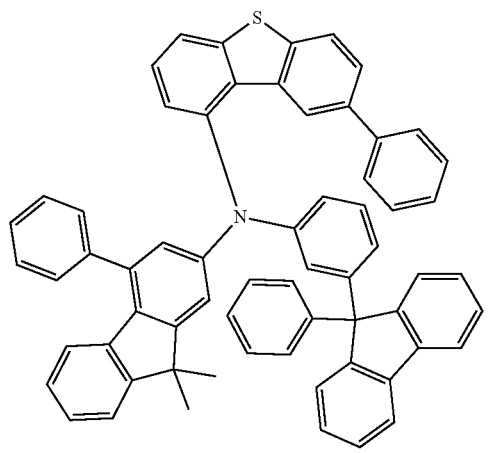
P2-19
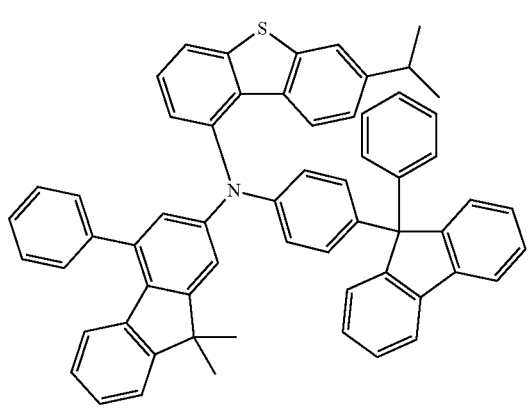
P2-20
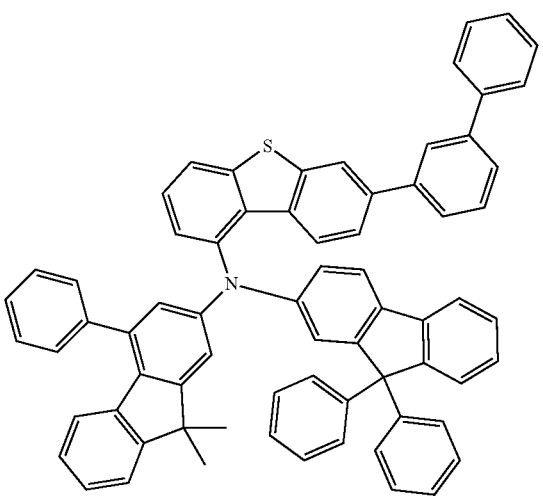
P2-21
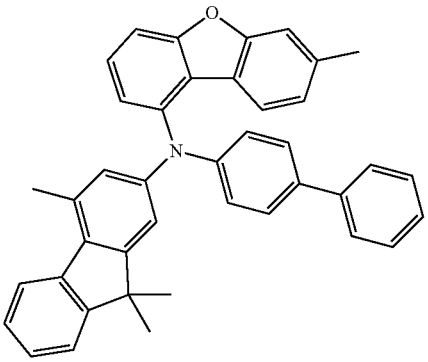
P2-22
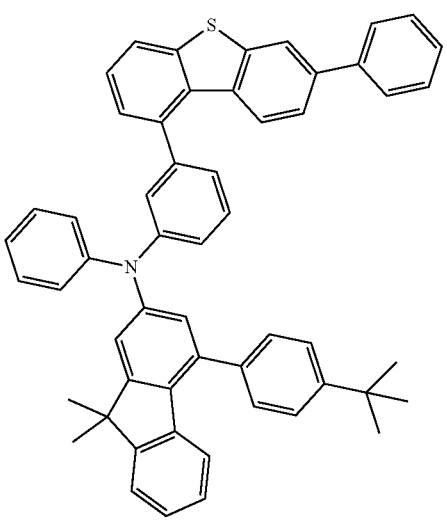
P2-23
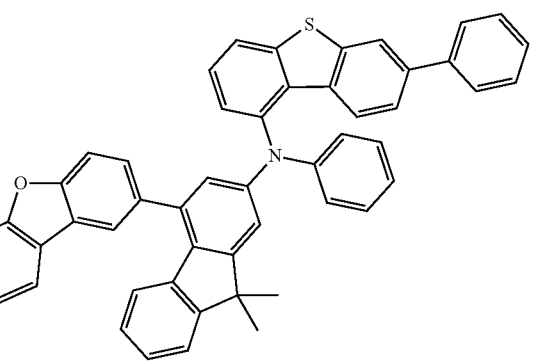
P2-24
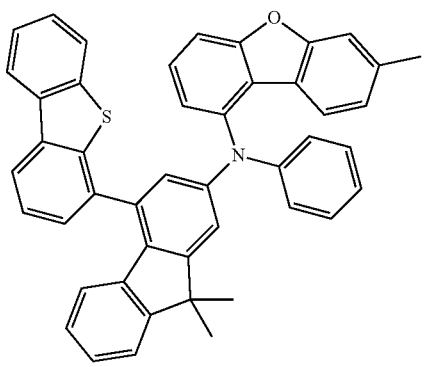

P2-25
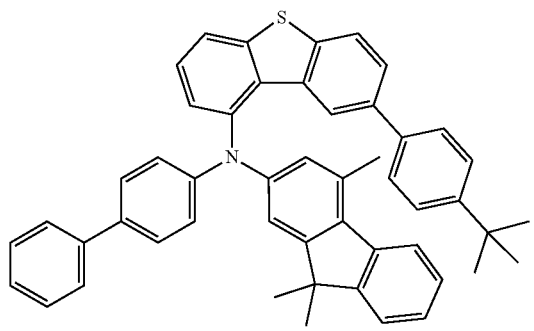
P2-26
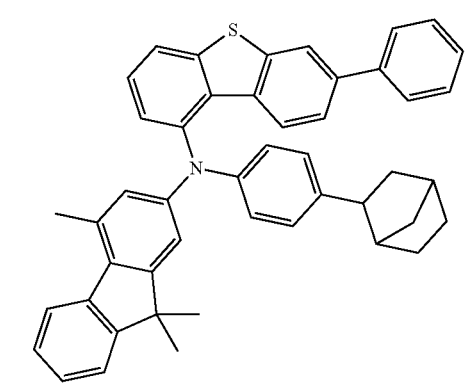
P2-27
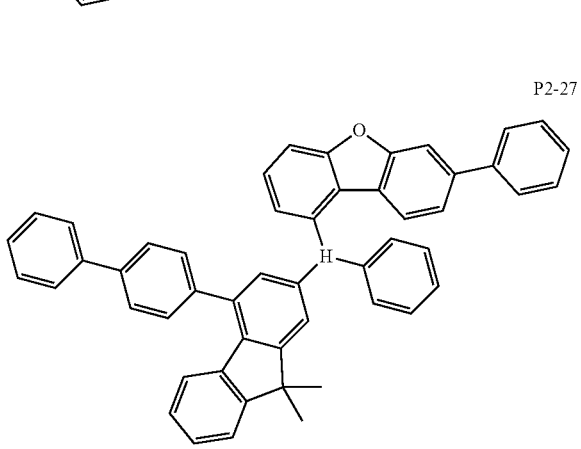
P2-28
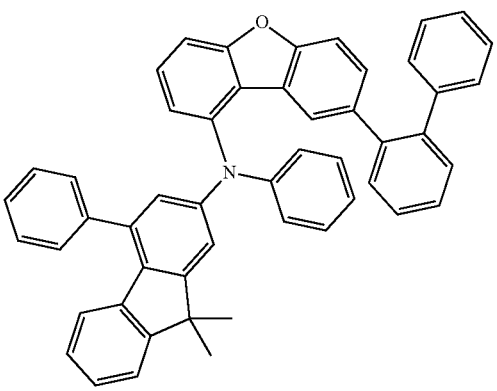
P2-29
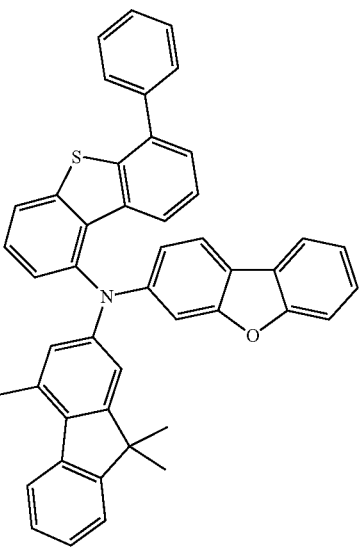
P2-30
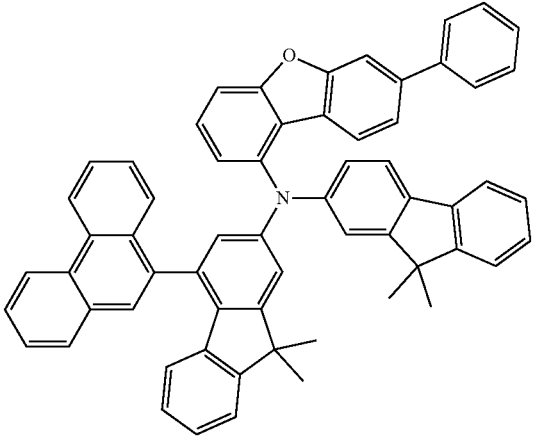
P2-31
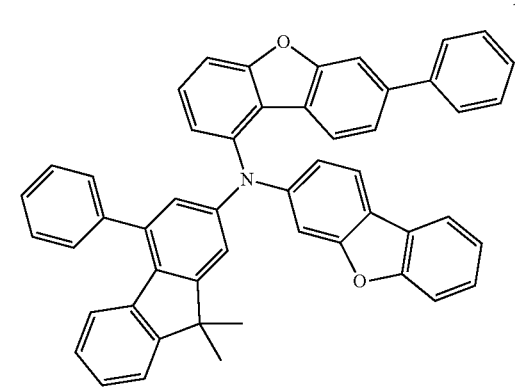

-continued
P2-32
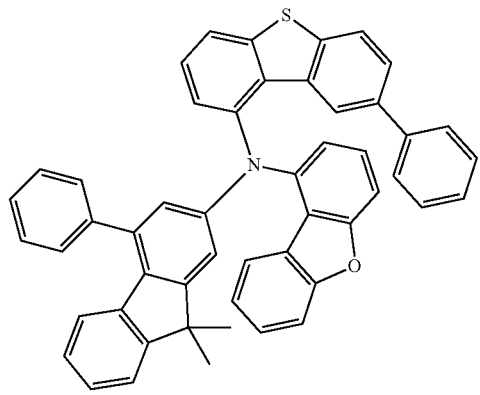
P2-33
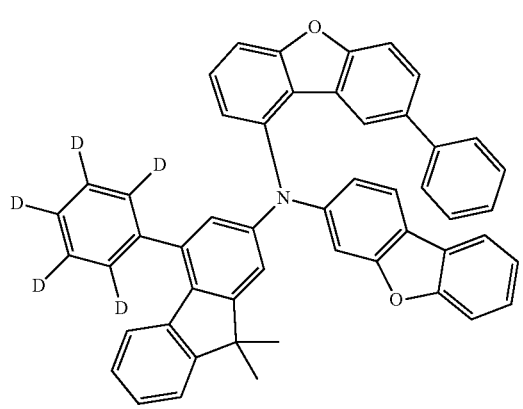
P2-34
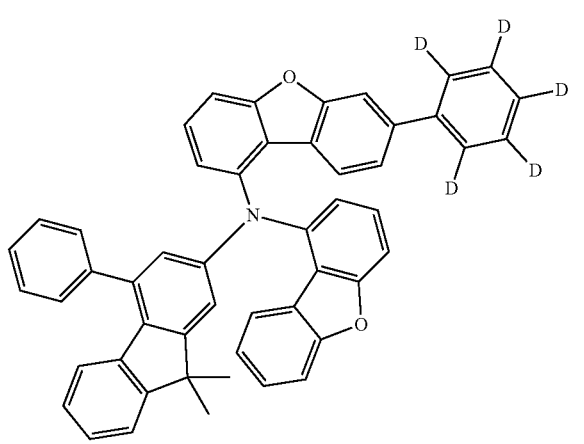
-continued
P2-35
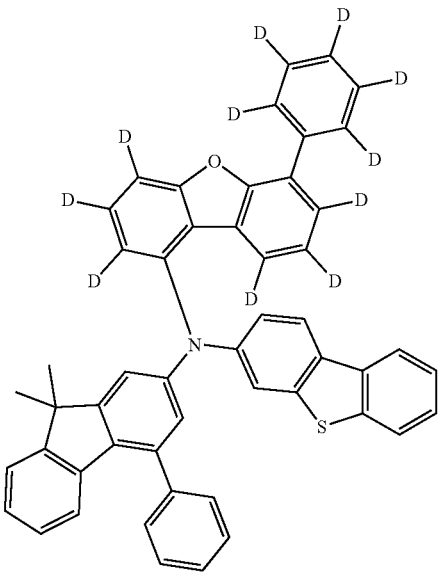
P2-36
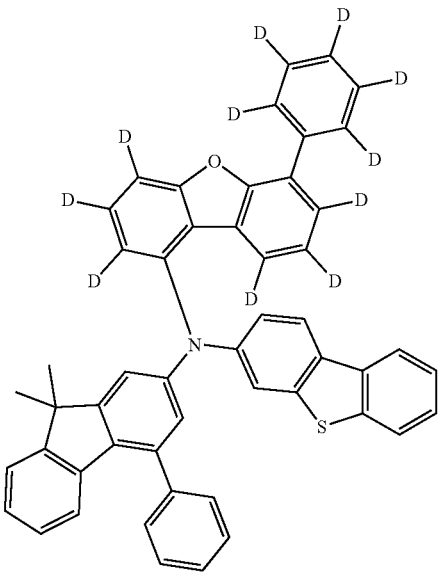
P2-37
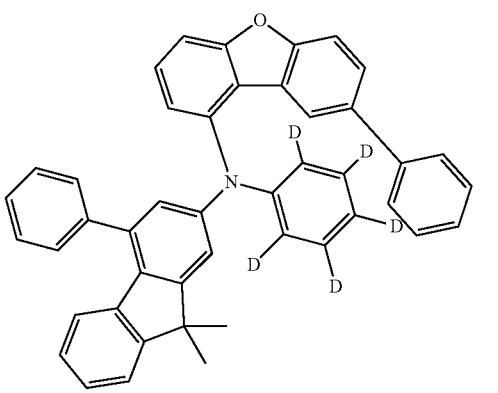

P2-38
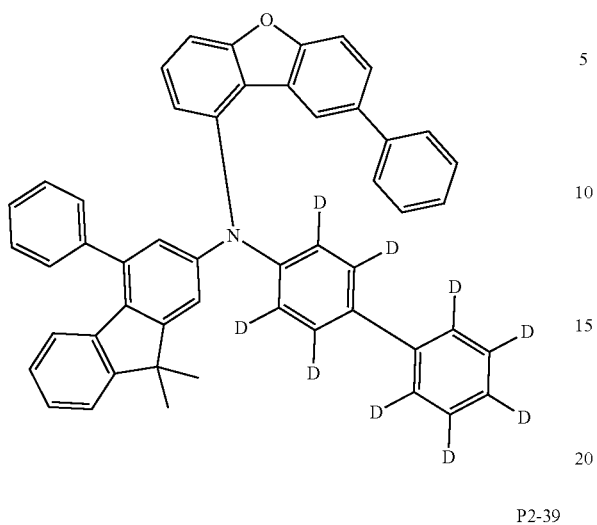
P2-41
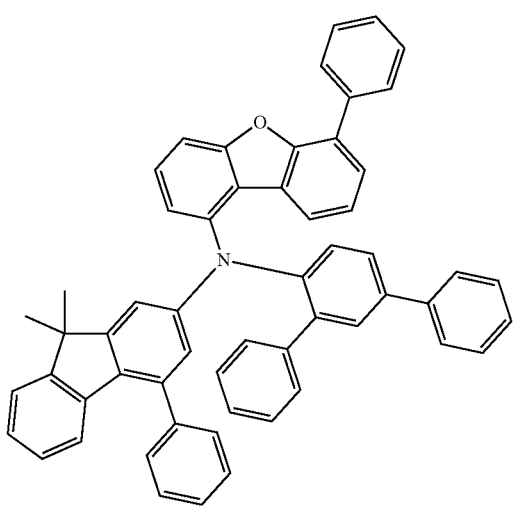
P2-39
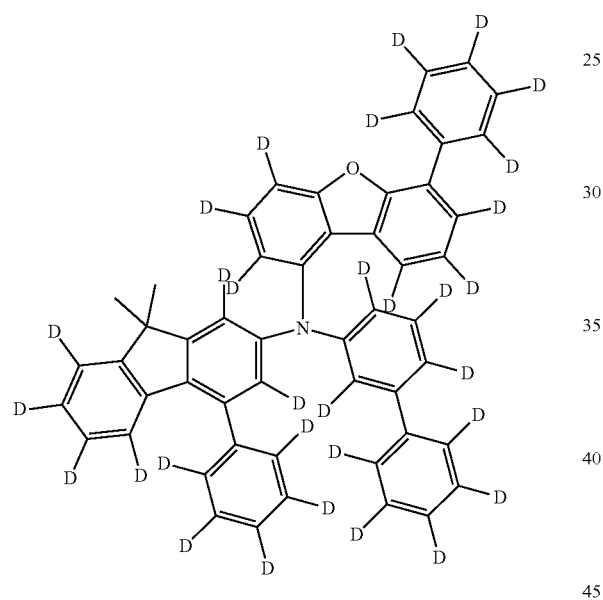
P2-42
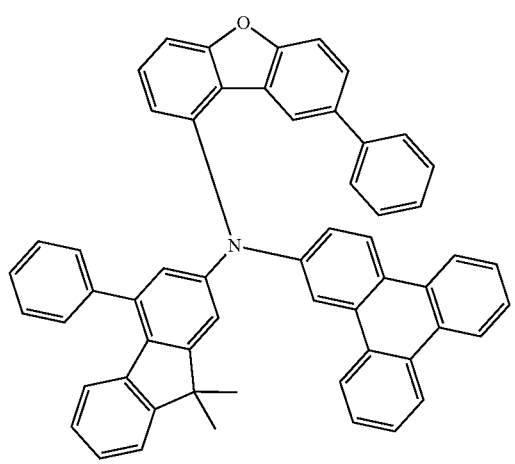
P2-40
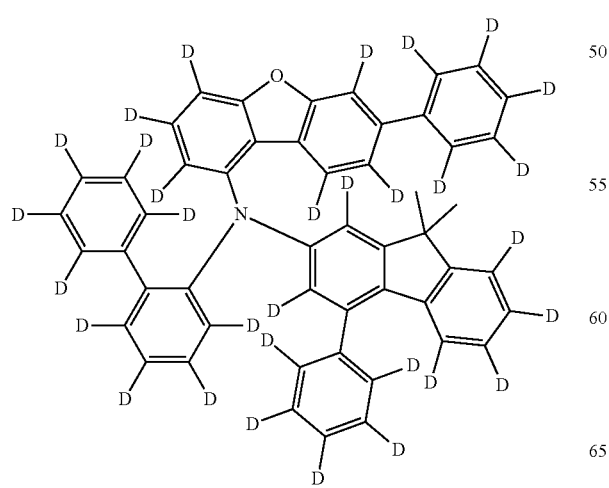
P2-43
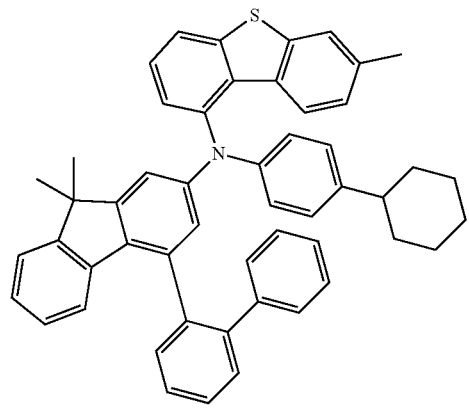

P2-44
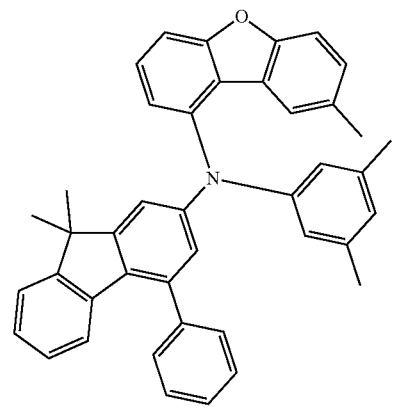
P2-45
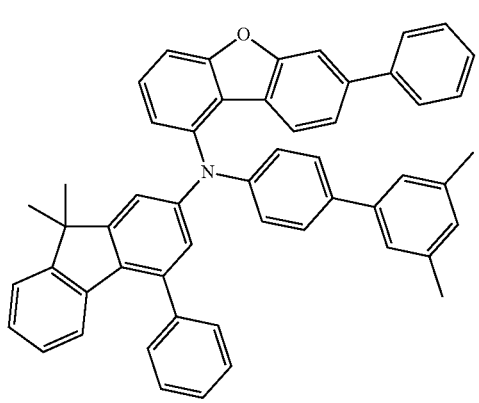
P2-46
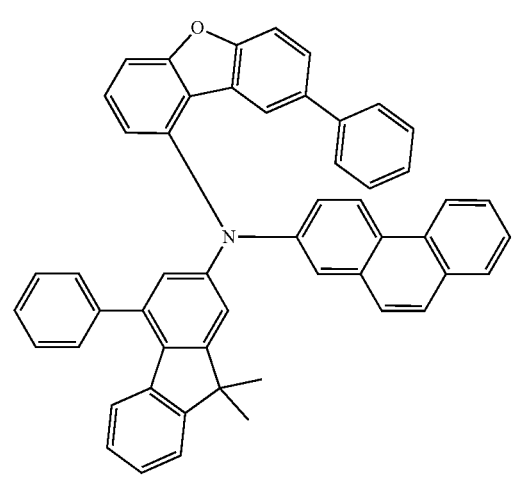
P2-47
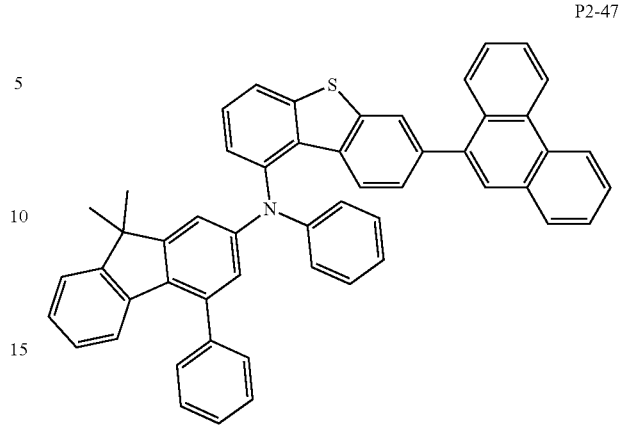
P2-48
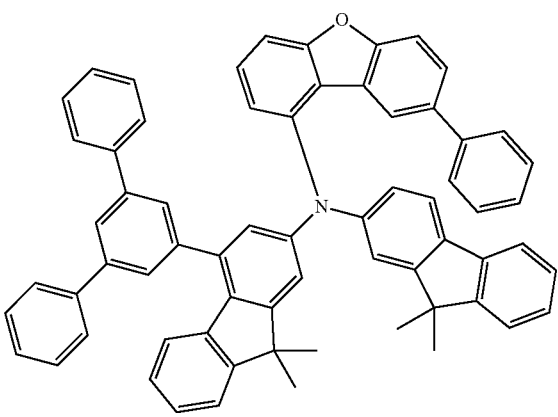
P2-49
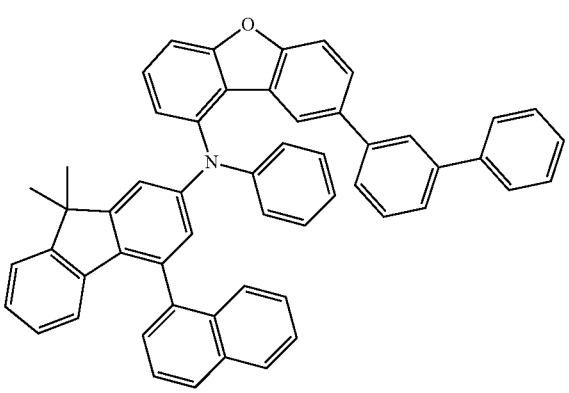
P2-50
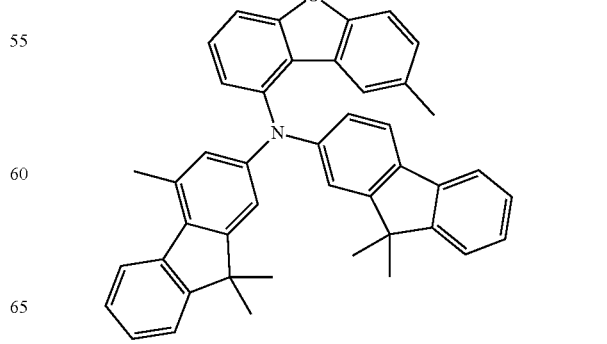

-continued

P2-51
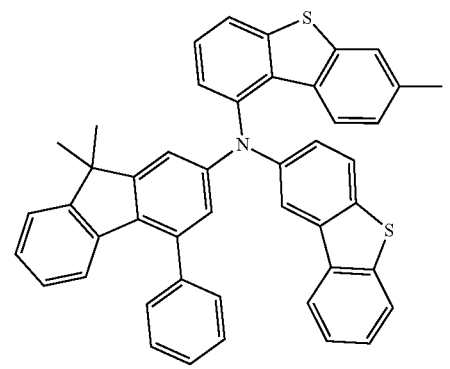

P2-52
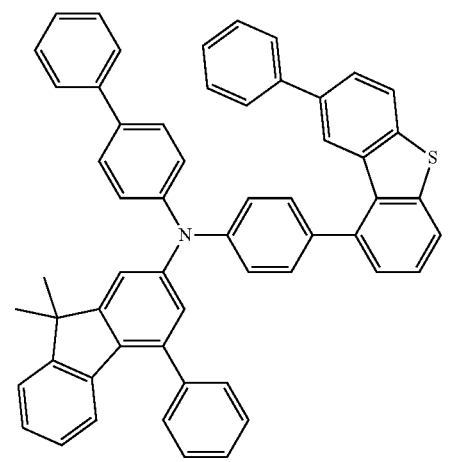

P2-53
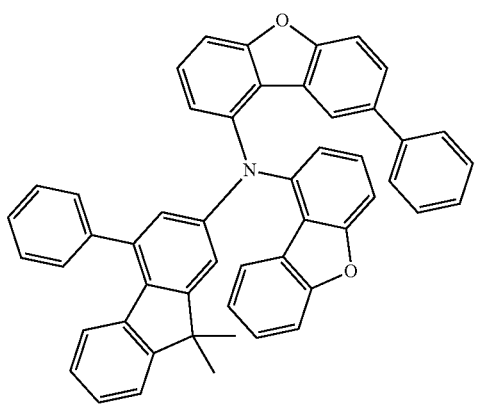

P2-54
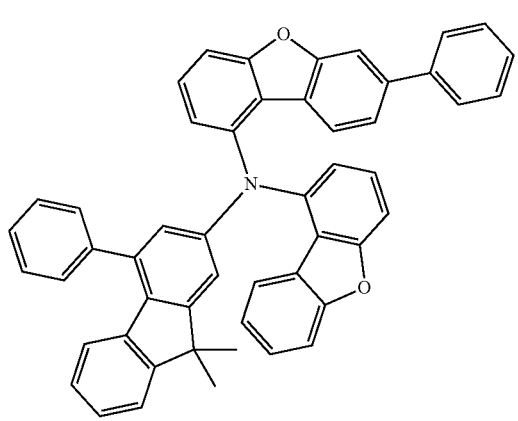

-continued

P2-55
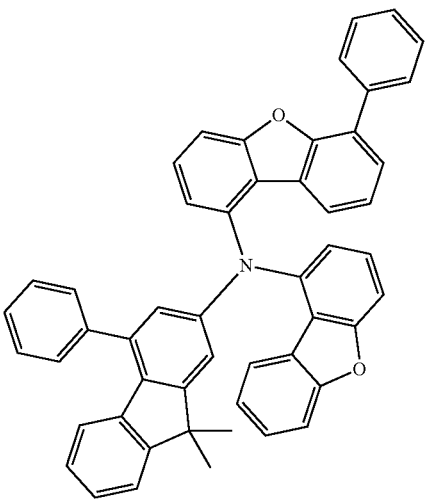

P2-56
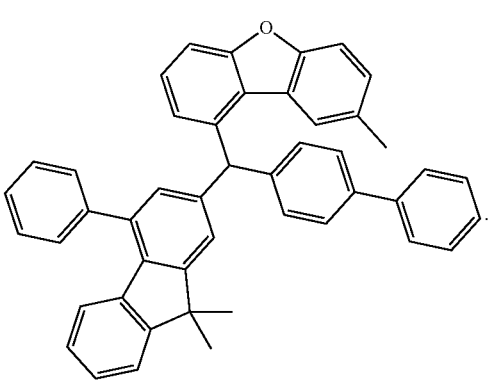

6. An organic electronic element comprising an anode; a cathode; and an organic material layer between the anode and the cathode, wherein the organic material layer comprises a single compound or 2 or more compounds represented by Formula (1-10) of claim 1.

7. The organic electronic element of claim 6, wherein the organic material layer comprises at least one of a hole injection layer, a hole transport layer, an emitting-auxiliary layer, an emitting layer, an electron transport auxiliary layer, an electron transport layer and an electron injection layer.

8. The organic electronic element of claim 6, wherein the organic material layer comprises an emitting-auxiliary layer.

9. The organic electronic element of claim 6, further comprising a light efficiency enhancing layer formed on at least one surface of the anode and the cathode, the surface being opposite to the organic material layer.

10. The organic electronic element of claim 6, wherein the organic material layer comprises 2 or more stacks comprising a hole transport layer, an emitting layer and an electron transport layer sequentially formed on the anode.

11. The organic electronic element of claim 10, wherein the organic material layer further comprises a charge generation layer formed between the 2 or more stacks.

12. An electronic device comprising a display device comprising the organic electronic element of claim 6; and a control unit for driving the display device.

13. The electronic device according to claim 12, wherein the organic electronic element is at least one of an OLED, an organic solar cell, an organic photo conductor (OPC), organic transistor (organic TFT) and an element for monochromic or white illumination.

14. A method for reusing a compound of Formula (1-10) of claim 1, comprising:
- recovering a crude organic light emitting material comprising the compound of Formula (1-10) from a deposition apparatus used in a process for depositing the organic emitting material to prepare an organic an organic light emitting device;
- removing impurities from the crude organic light emitting material;
- recovering the organic light emitting material after the impurities are removed; and
- purifying the recovered organic light emitting material to have a purity of 99.9% or higher.

* * * * *

UNITED STATES PATENT AND TRADEMARK OFFICE
CERTIFICATE OF CORRECTION

Page 1 of 2

PATENT NO. : 12,247,023 B2
APPLICATION NO. : 18/814915
DATED : March 11, 2025
INVENTOR(S) : Kim et al.

It is certified that error appears in the above-identified patent and that said Letters Patent is hereby corrected as shown below:

In the Claims

Column 73, Claim 2, Formula (1-12) should read:

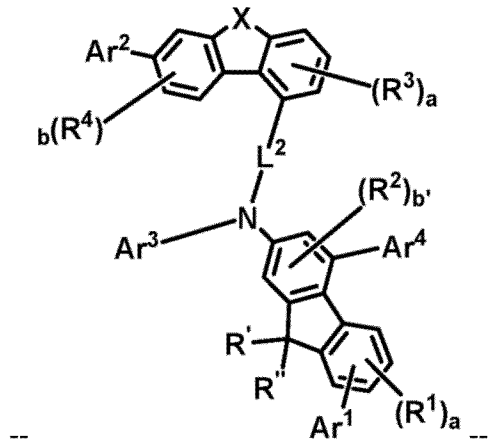

Column 73, Claim 2, Formula (1-13) should read:

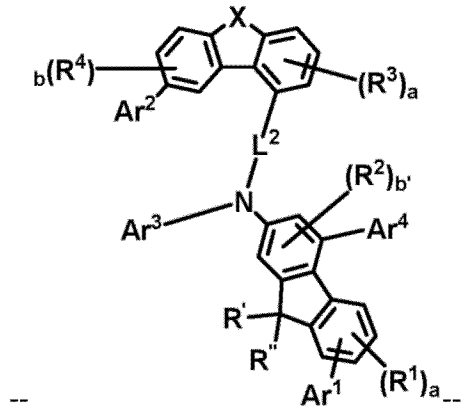

Signed and Sealed this
Twelfth Day of August, 2025

Coke Morgan Stewart
*Acting Director of the United States Patent and Trademark Office*

CERTIFICATE OF CORRECTION (continued)
U.S. Pat. No. 12,247,023 B2

Column 74, Claim 3, Line 42:
Please delete:
"a $C_2$-$C_{20}$ alkynyl group; a $C_2$-$C_{20}$ alkynyl group; a $C_6$-$C_{20}$ aryl group;"
And replace with:
-- a $C_2$-$C_{20}$ alkeynyl group; a $C_2$-$C_{20}$ alkynyl group; a $C_6$-$C_{20}$ aryl group; --